(12) United States Patent
Oborn et al.

(10) Patent No.: US 10,518,064 B2
(45) Date of Patent: *Dec. 31, 2019

(54) CATHETER ASSEMBLY INCLUDING A MULTI-LUMEN CONFIGURATION

(71) Applicant: C. R. Bard, Inc., Murray Hill, NJ (US)

(72) Inventors: Kelli D. Oborn, Erda, UT (US); Ryan T. Moehle, Salt Lake City, UT (US); William R Barron, Riverton, UT (US); Christian W. Crook, West Jordan, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 276 days.

This patent is subject to a terminal disclaimer.

(21) Appl. No.: 15/442,608

(22) Filed: Feb. 24, 2017

(65) Prior Publication Data

US 2017/0165453 A1 Jun. 15, 2017

Related U.S. Application Data

(60) Division of application No. 14/549,941, filed on Nov. 21, 2014, now Pat. No. 9,579,485, which is a
(Continued)

(51) Int. Cl.
*A61M 37/00* (2006.01)
*A61M 25/00* (2006.01)
(Continued)

(52) U.S. Cl.
CPC ........ *A61M 25/001* (2013.01); *A61M 1/3653* (2013.01); *A61M 1/3655* (2013.01);
(Continued)

(58) Field of Classification Search
CPC .............. A61M 25/007; A61M 1/3653; A61M 1/3661; A61M 2025/0031;
(Continued)

(56) References Cited

U.S. PATENT DOCUMENTS

| 701,075 A | 5/1902 | McCully |
|---|---|---|
| 1,696,018 A | 12/1928 | Scheliberg |

(Continued)

FOREIGN PATENT DOCUMENTS

| BE | 834211 | 2/1976 |
|---|---|---|
| CA | 1150122 | 7/1983 |

(Continued)

OTHER PUBLICATIONS

Arrow Cannon II Plus Brochure, 2006.
(Continued)

*Primary Examiner* — Leslie R Deak
(74) *Attorney, Agent, or Firm* — Rutan & Tucker LLP

(57) ABSTRACT

A catheter assembly for use in accessing a vasculature of a patient is disclosed. In one embodiment, the catheter assembly includes a catheter body that includes a flattened oval outer surface and defines first and second lumens. The catheter body defines a distal tip region that includes a venous lateral opening that is in fluid communication with the first lumen and includes a distal-facing portion. The distal tip region further includes an arterial lateral opening that is in fluid communication with the second lumen, includes a distal-facing portion, and is substantially unstaggered with respect to the venous lateral opening. A distal end opening is in fluid communication with a power injectable third lumen. In another embodiment, the first and second lumens each generally include a reniform cross-sectional shape. In yet another embodiment, a dual-lumen catheter includes first and second lumens that each define a modified ellipse cross-sectional shape.

13 Claims, 42 Drawing Sheets

Related U.S. Application Data continuation-in-part of application No. 13/329,156, filed on Dec. 16, 2011, now Pat. No. 8,894,601, which is a continuation of application No. 12/262,820, filed on Oct. 31, 2008, now Pat. No. 8,092,415.

(60) Provisional application No. 61/907,344, filed on Nov. 21, 2013, provisional application No. 60/984,661, filed on Nov. 1, 2007.

(51) Int. Cl.
  *A61M 1/36* (2006.01)
  *B29C 48/11* (2019.01)
  *B29C 48/12* (2019.01)
  *B29C 48/00* (2019.01)
  *A61M 5/00* (2006.01)
  *A61M 25/02* (2006.01)
  *A61M 25/09* (2006.01)
  *B29K 75/00* (2006.01)
  *B29L 31/00* (2006.01)

(52) U.S. Cl.
  CPC .......... *A61M 1/3661* (2014.02); *A61M 5/007* (2013.01); *A61M 25/003* (2013.01); *A61M 25/007* (2013.01); *A61M 25/0026* (2013.01); *A61M 25/0032* (2013.01); *A61M 25/0068* (2013.01); *A61M 25/0069* (2013.01); *A61M 25/0071* (2013.01); *A61M 25/0097* (2013.01); *A61M 25/02* (2013.01); *A61M 25/09* (2013.01); *B29C 48/0022* (2019.02); *B29C 48/11* (2019.02); *B29C 48/12* (2019.02); *A61M 2025/0008* (2013.01); *A61M 2025/0031* (2013.01); *A61M 2025/0037* (2013.01); *A61M 2025/0073* (2013.01); *A61M 2025/0081* (2013.01); *A61M 2025/0286* (2013.01); *A61M 2202/0021* (2013.01); *B29C 2793/009* (2013.01); *B29K 2075/00* (2013.01); *B29L 2031/7542* (2013.01)

(58) Field of Classification Search
  CPC .. A61M 2025/0037; A61M 2025/0073; A61M 2202/0021; A61M 25/0032; A61M 25/0068; A61M 25/0071; A61M 25/0009; A61M 25/0026
  See application file for complete search history.

(56) References Cited

U.S. PATENT DOCUMENTS

| | | |
|---|---|---|
| 1,856,811 A | 5/1932 | Inaki |
| 2,024,982 A | 12/1935 | Scott |
| 2,173,527 A | 9/1939 | Agayoff |
| 2,286,462 A | 6/1942 | Chaffin |
| 2,393,002 A | 1/1946 | Smith |
| 2,748,769 A | 6/1956 | Huber |
| 2,910,981 A | 11/1959 | Wilson et al. |
| 3,144,868 A | 8/1964 | Jascalevich |
| 3,176,690 A | 4/1965 | H'Doubler |
| 3,256,885 A | 6/1966 | Higgins et al. |
| 3,308,822 A | 3/1967 | De Luca |
| 3,416,532 A | 12/1968 | Grossman |
| 3,426,759 A | 2/1969 | Smith |
| 3,460,255 A | 8/1969 | Hutson |
| D217,795 S | 6/1970 | Spaven |
| 3,612,038 A | 10/1971 | Halligan |
| 3,736,939 A | 6/1973 | Taylor |
| 3,805,794 A | 4/1974 | Schlesinger |
| 3,812,851 A | 5/1974 | Rodriguez |
| 3,848,604 A | 11/1974 | Sackner |
| 3,890,977 A | 6/1975 | Wilson |
| 3,929,126 A | 12/1975 | Corsaut |
| 3,935,857 A | 2/1976 | Co |
| 3,995,623 A | 12/1976 | Blake et al. |
| 4,068,659 A | 1/1978 | Moorehead |
| 4,072,146 A | 2/1978 | Howes |
| 4,072,153 A | 2/1978 | Swartz |
| 4,098,275 A | 7/1978 | Consalvo |
| 4,114,625 A | 9/1978 | Onat |
| 4,117,836 A | 10/1978 | Erikson et al. |
| 4,129,129 A | 12/1978 | Amrine |
| 4,134,402 A | 1/1979 | Mahurkar |
| 4,149,535 A | 4/1979 | Volder |
| 4,180,068 A | 12/1979 | Jacobsen et al. |
| D254,444 S | 3/1980 | Levine |
| 4,248,224 A | 2/1981 | Jones |
| 4,276,880 A | 7/1981 | Malmin |
| 4,292,976 A | 10/1981 | Banka |
| 4,299,228 A | 11/1981 | Peters |
| 4,300,550 A | 11/1981 | Gandi et al. |
| 4,309,994 A | 1/1982 | Grunwald |
| 4,327,722 A | 5/1982 | Groshong et al. |
| 4,385,631 A | 5/1983 | Uthmann |
| 4,392,855 A | 7/1983 | Oreopoulos et al. |
| 4,403,983 A | 9/1983 | Edelman et al. |
| 4,405,313 A | 9/1983 | Sisley et al. |
| 4,406,656 A | 9/1983 | Hattler et al. |
| D272,651 S | 2/1984 | Mahurkar |
| 4,431,426 A | 2/1984 | Groshong et al. |
| 4,432,722 A | 2/1984 | Bohan, Jr. et al. |
| 4,432,752 A | 2/1984 | Marlon |
| 4,445,893 A | 5/1984 | Bodicky |
| 4,451,252 A | 5/1984 | Martin et al. |
| 4,453,928 A | 6/1984 | Steiger |
| 4,465,482 A | 8/1984 | Tittel et al. |
| 4,490,138 A | 12/1984 | Lipsky et al. |
| 4,493,696 A | 1/1985 | Uldall et al. |
| RE31,873 E | 4/1985 | Howes |
| 4,531,933 A | 7/1985 | Norton et al. |
| 4,543,087 A | 9/1985 | Sommercorn et al. |
| 4,545,373 A | 10/1985 | Christoudias |
| 4,549,879 A | 10/1985 | Groshong et al. |
| 4,557,261 A | 12/1985 | Rugheimer et al. |
| 4,568,329 A | 2/1986 | Mahurkar |
| 4,568,338 A | 2/1986 | Todd |
| 4,573,476 A | 3/1986 | Ruiz |
| 4,581,012 A | 4/1986 | Brown et al. |
| 4,583,968 A | 4/1986 | Mahurkar |
| 4,583,986 A | 4/1986 | Lapidus |
| 4,601,697 A | 7/1986 | Mammolenti et al. |
| 4,619,643 A | 10/1986 | Bai |
| 4,623,327 A | 11/1986 | Mahurkar |
| 4,626,240 A | 12/1986 | Edelman et al. |
| 4,642,101 A | 2/1987 | Krolikowski et al. |
| 4,643,711 A | 2/1987 | Bates |
| 4,666,426 A | 5/1987 | Aigner et al. |
| 4,668,221 A | 5/1987 | Luther |
| 4,670,009 A | 6/1987 | Bullock |
| 4,675,004 A | 6/1987 | Hadford et al. |
| 4,681,122 A | 7/1987 | Winters et al. |
| 4,681,564 A | 7/1987 | Landreneau |
| 4,681,570 A | 7/1987 | Dalton |
| 4,682,978 A | 7/1987 | Martin et al. |
| 4,687,471 A | 8/1987 | Twardowski et al. |
| 4,692,141 A | 9/1987 | Mahurkar |
| 4,694,838 A | 9/1987 | Wijayarthna et al. |
| 4,701,159 A | 10/1987 | Brown et al. |
| 4,702,917 A | 10/1987 | Schindler |
| 4,706,671 A | 11/1987 | Weinrib |
| 4,713,171 A | 12/1987 | Polaschegg |
| 4,717,379 A | 1/1988 | Ekholmer et al. |
| 4,735,620 A | 4/1988 | Ruiz |
| 4,737,141 A | 4/1988 | Spits et al. |
| 4,737,152 A | 4/1988 | Alchas |
| 4,738,667 A | 4/1988 | Galloway |
| 4,748,808 A | 6/1988 | Hill |
| 4,755,176 A | 7/1988 | Patel |
| 4,769,016 A | 9/1988 | Labianca |
| 4,770,652 A | 9/1988 | Mahurkar |
| 4,772,268 A | 9/1988 | Bates |
| 4,772,269 A | 9/1988 | Twardowski et al. |

(56) References Cited

U.S. PATENT DOCUMENTS

| | | |
|---|---|---|
| 4,776,841 A | 10/1988 | Catalano |
| 4,777,951 A | 10/1988 | Cribier et al. |
| 4,784,638 A | 11/1988 | Ghajar et al. |
| 4,790,809 A | 12/1988 | Kuntz |
| 4,795,439 A | 1/1989 | Guest |
| 4,801,297 A | 1/1989 | Mueller |
| D300,060 S | 2/1989 | Molgaard-Nielsen |
| 4,804,359 A | 2/1989 | Grunwald et al. |
| 4,808,155 A | 2/1989 | Mahurkar |
| 4,808,163 A | 2/1989 | Laub |
| 4,809,710 A | 3/1989 | Williamson |
| 4,820,265 A | 4/1989 | DeSatnick et al. |
| 4,832,687 A | 5/1989 | Smith, III |
| 4,834,709 A | 5/1989 | Banning et al. |
| 4,842,582 A | 6/1989 | Mahurkar |
| 4,842,592 A | 6/1989 | Caggiani et al. |
| 4,846,814 A | 7/1989 | Ruiz |
| 4,863,441 A | 9/1989 | Lindsay et al. |
| 4,867,742 A | 9/1989 | Calderon |
| 4,892,518 A | 1/1990 | Cupp et al. |
| 4,894,057 A | 1/1990 | Howes |
| 4,895,561 A | 1/1990 | Mahurkar |
| 4,898,591 A | 2/1990 | Jang et al. |
| 4,906,238 A | 3/1990 | Greenfeld et al. |
| 4,925,452 A | 5/1990 | Melinyshyn et al. |
| 4,927,418 A | 5/1990 | Dake et al. |
| 4,935,004 A | 6/1990 | Cruz |
| 4,935,010 A | 6/1990 | Cox et al. |
| 4,935,044 A | 6/1990 | Schoenpflug et al. |
| 4,936,826 A | 6/1990 | Amarasinghe |
| 4,950,232 A | 8/1990 | Ruzicka et al. |
| 4,950,259 A | 8/1990 | Geary et al. |
| 4,951,665 A | 8/1990 | Schneider |
| 4,961,729 A | 10/1990 | Vaillancourt |
| 4,961,731 A | 10/1990 | Bodicky et al. |
| 4,961,809 A | 10/1990 | Martin et al. |
| 4,968,307 A | 11/1990 | Dake et al. |
| 4,969,890 A | 11/1990 | Sugita et al. |
| 4,981,477 A | 1/1991 | Schon et al. |
| 4,985,014 A | 1/1991 | Orejola |
| 4,990,138 A | 2/1991 | Bacich et al. |
| 4,994,027 A | 2/1991 | Farrell |
| 4,995,865 A | 2/1991 | Gahara et al. |
| 5,009,636 A | 4/1991 | Wortley et al. |
| 5,015,230 A | 5/1991 | Martin et al. |
| 5,016,640 A | 5/1991 | Ruiz |
| 5,021,044 A | 6/1991 | Sharkawy |
| 5,041,101 A | 8/1991 | Seder et al. |
| 5,041,107 A | 8/1991 | Heil, Jr. |
| 5,049,138 A | 9/1991 | Chevalier et al. |
| 5,053,003 A | 10/1991 | Dadson et al. |
| 5,053,004 A | 10/1991 | Markel et al. |
| 5,053,023 A | 10/1991 | Martin |
| 5,057,073 A | 10/1991 | Martin |
| 5,059,170 A | 10/1991 | Cameron |
| 5,059,177 A | 10/1991 | Towne et al. |
| 5,069,673 A | 12/1991 | Shwab |
| 5,074,841 A | 12/1991 | Ademovic et al. |
| 5,084,013 A | 1/1992 | Takase et al. |
| 5,098,412 A | 3/1992 | Shiu et al. |
| 5,100,395 A | 3/1992 | Rosenberg et al. |
| 5,102,402 A | 4/1992 | Dror et al. |
| 5,106,368 A | 4/1992 | Uldall et al. |
| 5,106,376 A | 4/1992 | Mononen et al. |
| 5,111,829 A | 5/1992 | Alvarez de Toledo |
| 5,112,301 A | 5/1992 | Fenton, Jr. et al. |
| 5,114,423 A | 5/1992 | Kasprzyk et al. |
| 5,117,836 A | 6/1992 | Millar |
| 5,120,299 A | 6/1992 | Lombardi |
| 5,120,304 A | 6/1992 | Sasaki |
| 5,122,125 A | 6/1992 | Deuss et al. |
| 5,125,888 A | 6/1992 | Howard et al. |
| 5,125,904 A | 6/1992 | Lee |
| 5,129,891 A | 7/1992 | Young |
| 5,135,599 A | 8/1992 | Martin et al. |
| 5,139,486 A | 8/1992 | Moss |
| 5,156,592 A | 10/1992 | Martin et al. |
| 5,163,928 A | 11/1992 | Hobbs et al. |
| 5,167,623 A | 12/1992 | Cianci et al. |
| 5,171,216 A | 12/1992 | Dasse et al. |
| 5,171,227 A | 12/1992 | Twardowski et al. |
| 5,178,616 A | 1/1993 | Uemiya et al. |
| 5,188,592 A | 2/1993 | Hakki |
| 5,188,593 A | 2/1993 | Martin |
| 5,190,520 A | 3/1993 | Fenton, Jr. et al. |
| 5,190,529 A | 3/1993 | McCrory et al. |
| 5,191,898 A | 3/1993 | Millar |
| 5,195,962 A | 3/1993 | Martin et al. |
| 5,197,951 A | 3/1993 | Mahurkar |
| 5,197,973 A | 3/1993 | Pang et al. |
| 5,197,976 A | 3/1993 | Herweck et al. |
| 5,201,723 A | 4/1993 | Quinn |
| 5,207,648 A | 5/1993 | Gross |
| 5,207,650 A | 5/1993 | Martin |
| 5,209,723 A | 5/1993 | Twardowski et al. |
| 5,209,725 A | 5/1993 | Roth |
| 5,209,742 A | 5/1993 | Venema et al. |
| 5,215,527 A | 6/1993 | Beck et al. |
| 5,221,255 A | 6/1993 | Mahurkar et al. |
| 5,221,256 A | 6/1993 | Mahurkar |
| 5,222,949 A | 6/1993 | Kaldany |
| 5,226,880 A | 7/1993 | Martin et al. |
| 5,234,438 A | 8/1993 | Semrad |
| 5,236,016 A | 8/1993 | Vogelsang et al. |
| 5,242,398 A | 9/1993 | Knoll et al. |
| 5,246,430 A | 9/1993 | MacFarlane |
| 5,250,034 A | 10/1993 | Appling et al. |
| 5,254,084 A | 10/1993 | Geary |
| 5,273,527 A | 12/1993 | Schatz et al. |
| 5,273,534 A | 12/1993 | Knoepfler |
| 5,279,596 A | 1/1994 | Castaneda et al. |
| 5,279,599 A | 1/1994 | Wilk |
| 5,306,240 A | 4/1994 | Berry |
| 5,312,337 A | 5/1994 | Flaherty et al. |
| 5,312,357 A | 5/1994 | Buijs et al. |
| 5,318,517 A | 6/1994 | Reiman |
| 5,322,519 A | 6/1994 | Ash |
| 5,324,274 A | 6/1994 | Martin |
| 5,330,432 A | 7/1994 | Yoon |
| 5,338,308 A | 8/1994 | Wilk |
| 5,342,295 A | 8/1994 | Imran |
| 5,342,386 A | 8/1994 | Trotta |
| 5,346,471 A | 9/1994 | Raulerson |
| 5,348,536 A | 9/1994 | Young et al. |
| 5,350,358 A | 9/1994 | Martin |
| 5,360,397 A | 11/1994 | Pinchuk |
| 5,360,407 A | 11/1994 | Leonard et al. |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,380,290 A | 1/1995 | Makower et al. |
| 5,382,238 A | 1/1995 | Abrahamson et al. |
| 5,389,087 A | 2/1995 | Miraki |
| 5,389,090 A | 2/1995 | Fischell et al. |
| 5,395,316 A | 3/1995 | Martin et al. |
| 5,399,168 A | 3/1995 | Wadsworth, Jr. et al. |
| 5,403,291 A | 4/1995 | Abrahamson |
| 5,405,320 A | 4/1995 | Twardowski et al. |
| 5,405,341 A | 4/1995 | Martin |
| 5,409,463 A | 4/1995 | Thomas et al. |
| 5,417,668 A | 5/1995 | Setzer et al. |
| 5,423,768 A | 6/1995 | Folden et al. |
| 5,431,661 A | 7/1995 | Koch |
| 5,451,026 A | 9/1995 | Smith |
| 5,451,206 A | 9/1995 | Young |
| 5,451,233 A | 9/1995 | Yock |
| 5,458,570 A | 10/1995 | May, Jr. |
| 5,458,582 A | 10/1995 | Nakao |
| 5,462,533 A | 10/1995 | Daugherty |
| 5,472,417 A | 12/1995 | Martin et al. |
| 5,472,432 A | 12/1995 | Martin |
| 5,476,453 A | 12/1995 | Mehta |
| 5,480,380 A | 1/1996 | Martin |

(56) References Cited

U.S. PATENT DOCUMENTS

| | | |
|---|---|---|
| 5,486,159 A | 1/1996 | Mahurkar |
| 5,489,278 A | 2/1996 | Abrahamson |
| 5,496,292 A | 3/1996 | Burnham |
| 5,496,872 A | 3/1996 | Constancis et al. |
| 5,505,710 A | 4/1996 | Dorsey, III |
| 5,507,723 A | 4/1996 | Keshaviah |
| 5,509,897 A | 4/1996 | Twardowski et al. |
| 5,509,900 A | 4/1996 | Kirkman |
| 5,509,902 A | 4/1996 | Raulerson |
| 5,542,925 A | 8/1996 | Orth |
| 5,545,373 A | 8/1996 | Maziasz et al. |
| 5,556,390 A | 9/1996 | Hicks |
| 5,556,930 A | 9/1996 | Brehm et al. |
| 5,558,635 A | 9/1996 | Cannon |
| 5,562,609 A | 10/1996 | Brumbach |
| 5,562,696 A | 10/1996 | Nobles et al. |
| 5,569,182 A | 10/1996 | Twardowski et al. |
| 5,569,195 A | 10/1996 | Saab |
| 5,571,093 A | 11/1996 | Cruz et al. |
| 5,584,803 A | 12/1996 | Stevens et al. |
| 5,599,304 A | 2/1997 | Shaari |
| 5,599,328 A | 2/1997 | Stevens |
| 5,607,462 A | 3/1997 | Imran |
| 5,624,392 A | 4/1997 | Saab |
| 5,624,413 A | 4/1997 | Markel et al. |
| 5,632,729 A | 5/1997 | Cai et al. |
| 5,637,102 A | 6/1997 | Tolkoff et al. |
| 5,642,270 A | 6/1997 | Green et al. |
| 5,655,867 A | 8/1997 | Gysi et al. |
| 5,662,606 A | 9/1997 | Cimino et al. |
| 5,665,067 A | 9/1997 | Linder et al. |
| 5,674,237 A | 10/1997 | Ott |
| 5,685,867 A | 11/1997 | Twardowski et al. |
| 5,686,867 A | 11/1997 | Sutardja et al. |
| 5,693,030 A | 12/1997 | Lee et al. |
| 5,695,457 A | 12/1997 | St. Goar et al. |
| 5,704,915 A | 1/1998 | Melsky et al. |
| 5,713,849 A | 2/1998 | Bosma et al. |
| 5,713,853 A | 2/1998 | Clark et al. |
| 5,717,216 A | 2/1998 | McCoy et al. |
| 5,718,678 A | 2/1998 | Fleming, III |
| 5,718,692 A | 2/1998 | Schon et al. |
| 5,720,735 A | 2/1998 | Dorros |
| 5,738,649 A | 4/1998 | Macoviak |
| 5,741,329 A | 4/1998 | Agrawal et al. |
| 5,743,873 A | 4/1998 | Cai et al. |
| 5,752,939 A | 5/1998 | Makoto et al. |
| 5,769,796 A | 6/1998 | Palermo et al. |
| 5,772,643 A | 6/1998 | Howell et al. |
| 5,776,096 A | 7/1998 | Fields |
| 5,776,111 A | 7/1998 | Tesio |
| 5,785,686 A | 7/1998 | Runge |
| 5,792,094 A | 8/1998 | Stevens et al. |
| 5,792,123 A | 8/1998 | Ensminger |
| 5,797,869 A | 8/1998 | Martin et al. |
| 5,800,384 A | 9/1998 | Russell et al. |
| 5,800,414 A | 9/1998 | Cazal et al. |
| 5,800,516 A | 9/1998 | Fine et al. |
| 5,807,311 A | 9/1998 | Palestrant |
| 5,807,318 A | 9/1998 | St. Goar et al. |
| 5,807,329 A | 9/1998 | Gelman |
| 5,809,897 A | 9/1998 | Powell et al. |
| 5,810,789 A | 9/1998 | Powers et al. |
| 5,814,016 A | 9/1998 | Valley et al. |
| 5,830,184 A | 11/1998 | Basta |
| 5,830,196 A | 11/1998 | Hicks |
| 5,833,671 A | 11/1998 | Macoviak et al. |
| 5,843,048 A | 12/1998 | Gross |
| 5,858,009 A | 1/1999 | Jonkman |
| 5,861,010 A | 1/1999 | Boussignac et al. |
| 5,868,717 A | 2/1999 | Prosl |
| 5,873,865 A | 2/1999 | Horzewski et al. |
| 5,876,366 A | 3/1999 | Dykstra et al. |
| 5,876,426 A | 3/1999 | Kume et al. |
| 5,882,347 A | 3/1999 | Mouris-Laan et al. |
| 5,891,111 A | 4/1999 | Ismael et al. |
| 5,904,670 A | 5/1999 | Schreiner |
| 5,911,715 A | 6/1999 | Berg et al. |
| 5,913,848 A | 6/1999 | Luther et al. |
| 5,916,208 A | 6/1999 | Luther et al. |
| 5,919,160 A | 7/1999 | Sanfilippo, II |
| 5,944,732 A | 8/1999 | Raulerson et al. |
| 5,947,937 A | 9/1999 | Urrutia et al. |
| 5,947,953 A | 9/1999 | Ash et al. |
| 5,957,879 A | 9/1999 | Roberts et al. |
| 5,957,893 A | 9/1999 | Luther et al. |
| 5,957,912 A | 9/1999 | Heitzmann |
| 5,961,486 A | 10/1999 | Twardowski et al. |
| 5,964,796 A | 10/1999 | Imran |
| 5,976,103 A | 11/1999 | Martin |
| 5,976,120 A | 11/1999 | Chow et al. |
| 5,980,551 A | 11/1999 | Summers et al. |
| 5,984,908 A | 11/1999 | Davis et al. |
| 5,989,206 A | 11/1999 | Prosl et al. |
| 5,989,213 A | 11/1999 | Maginot |
| 6,001,079 A | 12/1999 | Pourchez |
| 6,033,382 A | 3/2000 | Basta |
| 6,036,654 A | 3/2000 | Quinn et al. |
| 6,059,771 A | 5/2000 | Balbierz et al. |
| 6,074,374 A | 6/2000 | Fulton |
| 6,086,555 A | 7/2000 | Eliasen et al. |
| 6,086,557 A | 7/2000 | Morejohn et al. |
| 6,090,096 A | 7/2000 | St. Goar et al. |
| 6,099,513 A | 8/2000 | Spehalski |
| 6,103,778 A | 8/2000 | Hyon et al. |
| 6,106,540 A | 8/2000 | White et al. |
| 6,113,572 A | 9/2000 | Gailey et al. |
| 6,117,117 A | 9/2000 | Mauch |
| 6,120,494 A | 9/2000 | Jonkman |
| 6,126,631 A | 10/2000 | Loggie |
| 6,132,425 A | 10/2000 | Gough |
| 6,143,013 A | 11/2000 | Samson et al. |
| 6,146,354 A | 11/2000 | Beil |
| 6,146,373 A | 11/2000 | Cragg et al. |
| 6,152,909 A | 11/2000 | Bagaoisan et al. |
| 6,156,016 A | 12/2000 | Maginot |
| 6,161,547 A | 12/2000 | Barbut |
| 6,178,356 B1 | 1/2001 | Chastain et al. |
| 6,180,059 B1 | 1/2001 | Divino, Jr. et al. |
| 6,190,349 B1 | 2/2001 | Ash et al. |
| 6,190,371 B1 | 2/2001 | Maginot et al. |
| 6,193,685 B1 | 2/2001 | Goodin |
| 6,196,996 B1 | 3/2001 | Teirstein |
| 6,206,849 B1 | 3/2001 | Martin et al. |
| 6,210,365 B1 | 4/2001 | Afzal |
| 6,210,380 B1 | 4/2001 | Mauch |
| 6,217,527 B1 | 4/2001 | Selmon et al. |
| 6,224,622 B1 | 5/2001 | Kotzev |
| 6,238,406 B1 | 5/2001 | Ellis et al. |
| 6,264,627 B1 | 7/2001 | Liska et al. |
| 6,273,879 B1 | 8/2001 | Keith et al. |
| 6,280,413 B1 | 8/2001 | Clark et al. |
| 6,280,423 B1 | 8/2001 | Davey et al. |
| 6,287,326 B1 | 9/2001 | Pecor |
| 6,293,927 B1 | 9/2001 | McGuckin, Jr. |
| 6,293,958 B1 | 9/2001 | Berry et al. |
| 6,296,631 B2 | 10/2001 | Chow |
| 6,299,631 B1 | 10/2001 | Shalaby |
| 6,322,551 B1 | 11/2001 | Brugger |
| 6,328,730 B1 | 12/2001 | Harkrider, Jr. |
| 6,342,120 B1 | 1/2002 | Basta |
| 6,361,529 B1 | 3/2002 | Goodin et al. |
| 6,383,172 B1 | 5/2002 | Barbut |
| 6,394,141 B2 | 5/2002 | Wages et al. |
| 6,394,142 B1 | 5/2002 | Woelfel et al. |
| 6,409,700 B1 | 6/2002 | Siegel, Jr. et al. |
| 6,413,228 B1 | 7/2002 | Hung et al. |
| 6,428,513 B1 | 8/2002 | Abrahamson |
| 6,443,922 B1 | 9/2002 | Roberts et al. |
| 6,450,988 B1 | 9/2002 | Bradshaw |
| 6,453,185 B1 | 9/2002 | O'Keefe |
| 6,454,997 B1 | 9/2002 | Divino, Jr. et al. |
| 6,455,608 B1 | 9/2002 | Jia et al. |
| 6,463,335 B1 | 10/2002 | Munch et al. |

(56) References Cited

U.S. PATENT DOCUMENTS

| | | |
|---|---|---|
| 6,468,287 B1 | 10/2002 | Baugh |
| 6,473,633 B1 | 10/2002 | Heil, Jr. et al. |
| 6,475,207 B1 | 11/2002 | Maginot et al. |
| 6,475,209 B1 | 11/2002 | Larson et al. |
| 6,478,789 B1 | 11/2002 | Spehalski et al. |
| 6,482,169 B1 | 11/2002 | Kuhle |
| 6,533,763 B1 | 3/2003 | Schneiter |
| 6,565,594 B1 | 5/2003 | Herweck et al. |
| 6,576,001 B2 | 6/2003 | Werneth et al. |
| 6,582,459 B1 | 6/2003 | Lau et al. |
| 6,585,705 B1 | 7/2003 | Maginot et al. |
| 6,592,565 B2 | 7/2003 | Twardowski |
| 6,595,966 B2 | 7/2003 | Davey et al. |
| 6,620,118 B1 | 9/2003 | Prosl et al. |
| 6,638,242 B2 | 10/2003 | Wilson et al. |
| 6,659,134 B2 | 12/2003 | Navis |
| 6,682,498 B2 | 1/2004 | Ross |
| 6,682,519 B1 | 1/2004 | Schon |
| 6,691,625 B2 | 2/2004 | Duncan |
| 6,695,832 B2 | 2/2004 | Schon et al. |
| 6,702,776 B2 | 3/2004 | Quinn |
| 6,712,797 B1 | 3/2004 | Southern, Jr. |
| 6,712,798 B2 | 3/2004 | Constantz |
| 6,719,717 B1 | 4/2004 | Johnson et al. |
| 6,719,749 B1 | 4/2004 | Schweikert et al. |
| 6,723,084 B1 | 4/2004 | Maginot et al. |
| 6,723,114 B2 | 4/2004 | Shalaby |
| 6,730,299 B1 | 5/2004 | Tayot et al. |
| 6,752,827 B2 | 6/2004 | Ross et al. |
| 6,755,851 B2 | 6/2004 | Noda et al. |
| 6,758,836 B2 | 7/2004 | Zawacki |
| 6,786,664 B2 | 9/2004 | Claramunt et al. |
| 6,786,884 B1 | 9/2004 | DeCant, Jr. et al. |
| 6,796,991 B2 | 9/2004 | Nardeo |
| 6,797,107 B1 | 9/2004 | Kotzey |
| 6,808,510 B1 | 10/2004 | DiFiore |
| 6,814,718 B2 | 11/2004 | McGuckin, Jr. et al. |
| 6,819,951 B2 | 11/2004 | Patel et al. |
| 6,821,287 B1 | 11/2004 | Jang |
| 6,824,554 B1 | 11/2004 | Jang |
| 6,835,452 B1 | 12/2004 | Hamerski |
| 6,837,864 B1 | 1/2005 | Bertolero et al. |
| 6,852,079 B2 | 2/2005 | Miyano |
| 6,852,097 B1 | 2/2005 | Fulton, III |
| 6,858,019 B2 | 2/2005 | McGuckin, Jr. et al. |
| 6,872,198 B1 | 3/2005 | Wilson et al. |
| 6,878,143 B2 | 4/2005 | Andersen |
| 6,881,211 B2 | 4/2005 | Schweikert et al. |
| 6,884,253 B1 | 4/2005 | McFarlane |
| 6,911,014 B2 | 6/2005 | Wentling et al. |
| 6,913,601 B2 | 7/2005 | St Goar et al. |
| 6,916,313 B2 | 7/2005 | Cunningham |
| 6,921,396 B1 | 7/2005 | Wilson et al. |
| 6,921,411 B2 | 7/2005 | Yock |
| 6,934,142 B2 | 8/2005 | Grosse et al. |
| 6,966,886 B2 | 11/2005 | Appling |
| 6,969,381 B2 | 11/2005 | Voorhees |
| 6,979,318 B1 | 12/2005 | McDonald et al. |
| 6,991,625 B1 | 1/2006 | Gately et al. |
| D515,211 S | 2/2006 | Chesnin |
| 6,997,894 B2 | 2/2006 | Caresio |
| 7,008,395 B1 | 3/2006 | Loggie |
| 7,011,645 B2 | 3/2006 | McGuckin, Jr. et al. |
| 7,018,384 B2 | 3/2006 | Skakoon |
| 7,029,467 B2 | 4/2006 | Currier et al. |
| 7,066,914 B2 | 6/2006 | Andersen |
| 7,066,925 B2 | 6/2006 | Gately et al. |
| 7,074,213 B2 | 7/2006 | McGuckin, Jr. et al. |
| 7,077,829 B2 | 7/2006 | McGuckin, Jr. et al. |
| 7,087,053 B2 | 8/2006 | Vanney |
| 7,090,654 B2 | 8/2006 | Lotito et al. |
| 7,108,674 B2 | 9/2006 | Quinn |
| D530,420 S | 10/2006 | Chesnin |
| 7,128,734 B1 | 10/2006 | Wilson et al. |
| 7,130,700 B2 | 10/2006 | Gardeski et al. |
| 7,141,035 B2 | 11/2006 | Haggstrom |
| RE39,451 E | 12/2006 | Kuhle |
| 7,182,746 B2 | 2/2007 | Haarala et al. |
| 7,300,430 B2 | 11/2007 | Wilson et al. |
| 7,322,953 B2 | 1/2008 | Redinger |
| 7,347,852 B2 | 3/2008 | Hobbs et al. |
| 7,381,204 B2 | 6/2008 | Wilson et al. |
| 7,393,339 B2 | 7/2008 | Zawacki et al. |
| 7,422,571 B2 | 9/2008 | Schweikert et al. |
| 7,465,286 B2 | 12/2008 | Patterson et al. |
| 7,485,107 B2 | 2/2009 | DiFiore et al. |
| 7,569,029 B2 | 8/2009 | Clark |
| 7,575,563 B2 | 8/2009 | Appling |
| 7,651,482 B2 | 1/2010 | Harris |
| 7,686,823 B2 | 3/2010 | Pingleton et al. |
| 7,798,999 B2 | 9/2010 | Bailey et al. |
| 7,972,465 B2 | 7/2011 | Patterson et al. |
| 8,021,321 B2 | 9/2011 | Zawacki |
| 8,066,660 B2 | 11/2011 | Gregersen et al. |
| 8,092,415 B2 | 1/2012 | Moehle |
| 8,100,863 B2 | 1/2012 | Moehle et al. |
| 8,152,951 B2 | 4/2012 | Zawacki et al. |
| 8,206,371 B2 | 6/2012 | Nimkar et al. |
| 8,292,841 B2 | 10/2012 | Gregersen |
| 8,500,939 B2 | 8/2013 | Nimkar et al. |
| 8,540,661 B2 | 9/2013 | Gregersen |
| 8,597,275 B2 | 12/2013 | Nimkar et al. |
| 8,696,614 B2 | 4/2014 | Gregersen et al. |
| 8,808,227 B2 | 8/2014 | Zawacki et al. |
| 8,894,601 B2 | 11/2014 | Moehle et al. |
| 8,992,454 B2 | 3/2015 | Anand |
| 9,174,019 B2 | 11/2015 | Gregersen |
| 9,233,200 B2 | 1/2016 | Gregersen et al. |
| 9,572,956 B2 | 2/2017 | Nimkar et al. |
| 9,579,485 B2 * | 2/2017 | Obom ............ A61M 25/0068 |
| 9,610,422 B2 | 4/2017 | Moehle et al. |
| 9,669,149 B2 | 6/2017 | Anand |
| 9,782,535 B2 | 10/2017 | Anand |
| 10,105,514 B2 | 10/2018 | Nimkar et al. |
| 10,207,043 B2 | 2/2019 | Gregersen |
| 10,258,732 B2 | 4/2019 | Gregersen et al. |
| 10,258,768 B2 | 4/2019 | Loesener et al. |
| 2001/0041857 A1 | 11/2001 | Sansoucy |
| 2001/0041873 A1 | 11/2001 | Dopper et al. |
| 2002/0013569 A1 | 1/2002 | Sterman et al. |
| 2002/0026156 A1 | 2/2002 | Quinn |
| 2002/0055724 A1 | 5/2002 | Hughes |
| 2002/0086047 A1 | 7/2002 | Mueller et al. |
| 2002/0087108 A1 | 7/2002 | Maginot et al. |
| 2002/0087145 A1 | 7/2002 | Ehwald et al. |
| 2002/0091362 A1 | 7/2002 | Maginot et al. |
| 2002/0091430 A1 | 7/2002 | Dobak et al. |
| 2002/0099326 A1 | 7/2002 | Wilson et al. |
| 2002/0099327 A1 | 7/2002 | Wilson et al. |
| 2002/0107506 A1 | 8/2002 | McGuckin et al. |
| 2002/0138031 A1 | 9/2002 | Ross |
| 2002/0169490 A1 | 11/2002 | Noda et al. |
| 2002/0173770 A1 | 11/2002 | Flory et al. |
| 2002/0177904 A1 | 11/2002 | Huxel et al. |
| 2003/0023198 A1 | 1/2003 | Twardowski |
| 2003/0032734 A1 | 2/2003 | Roby |
| 2003/0088213 A1 | 5/2003 | Schweikert et al. |
| 2003/0093027 A1 | 5/2003 | McGuckin et al. |
| 2003/0097091 A1 | 5/2003 | Hobbs et al. |
| 2003/0135147 A1 | 7/2003 | Rosenberg et al. |
| 2003/0144623 A1 | 7/2003 | Heath et al. |
| 2003/0149395 A1 | 8/2003 | Zawacki |
| 2003/0153898 A1 | 8/2003 | Schon et al. |
| 2003/0163145 A1 | 8/2003 | Raulerson |
| 2003/0187411 A1 | 10/2003 | Constantz |
| 2003/0204179 A1 | 10/2003 | Davey et al. |
| 2004/0039350 A1 | 2/2004 | McKittrick |
| 2004/0054321 A1 | 3/2004 | Schon et al. |
| 2004/0059314 A1 | 3/2004 | Schon et al. |
| 2004/0064086 A1 | 4/2004 | Gottlieb et al. |
| 2004/0065333 A1 | 4/2004 | Wilson et al. |
| 2004/0075198 A1 | 4/2004 | Schweikert et al. |
| 2004/0087892 A1 | 5/2004 | Cunningham |
| 2004/0092863 A1 | 5/2004 | Raulerson et al. |

(56) References Cited

U.S. PATENT DOCUMENTS

| | | |
|---|---|---|
| 2004/0097863 A1 | 5/2004 | Appling |
| 2004/0097903 A1 | 5/2004 | Raulerson |
| 2004/0122418 A1 | 6/2004 | Voorhees |
| 2004/0147903 A1 | 7/2004 | Latini |
| 2004/0167463 A1 | 8/2004 | Zawacki et al. |
| 2004/0171997 A1 | 9/2004 | Wilson et al. |
| 2004/0172003 A1 | 9/2004 | Wilson et al. |
| 2004/0176739 A1 | 9/2004 | Stephens et al. |
| 2004/0193102 A1 | 9/2004 | Haggstrom |
| 2004/0197301 A1 | 10/2004 | Zhao et al. |
| 2004/0210180 A1 | 10/2004 | Altman |
| 2004/0210187 A1 | 10/2004 | Zawacki |
| 2004/0210237 A1 | 10/2004 | Ross et al. |
| 2004/0220550 A1 | 11/2004 | Schryver |
| 2004/0230204 A1 | 11/2004 | Wortley et al. |
| 2004/0243095 A1 | 12/2004 | Nimkar et al. |
| 2004/0249337 A1 | 12/2004 | DiFiore |
| 2005/0003322 A1 | 1/2005 | Logan et al. |
| 2005/0004504 A1 | 1/2005 | Frye et al. |
| 2005/0013341 A1 | 1/2005 | Baghai |
| 2005/0019382 A1 | 1/2005 | Kummer et al. |
| 2005/0025641 A1 | 2/2005 | Shibata et al. |
| 2005/0027282 A1 | 2/2005 | Schweikert et al. |
| 2005/0027289 A1 | 2/2005 | Castellano et al. |
| 2005/0033222 A1 | 2/2005 | Haggstrom et al. |
| 2005/0033264 A1 | 2/2005 | Redinger |
| 2005/0054989 A1 | 3/2005 | McGuckin et al. |
| 2005/0055012 A1 | 3/2005 | Trerotola |
| 2005/0059925 A1 | 3/2005 | Maginot et al. |
| 2005/0070842 A1 | 3/2005 | Lotito et al. |
| 2005/0080398 A1 | 4/2005 | Markel et al. |
| 2005/0085765 A1 | 4/2005 | Voorhees |
| 2005/0096585 A1 | 5/2005 | Schon et al. |
| 2005/0113904 A1 | 5/2005 | Shank et al. |
| 2005/0131341 A1 | 6/2005 | McGuckin et al. |
| 2005/0171469 A1 | 8/2005 | Cunningham |
| 2005/0187535 A1 | 8/2005 | Wilson et al. |
| 2005/0209582 A1 | 9/2005 | Quinn et al. |
| 2005/0215977 A1 | 9/2005 | Uschold |
| 2005/0228339 A1 | 10/2005 | Clark |
| 2005/0245900 A1 | 11/2005 | Ash |
| 2005/0251190 A1 | 11/2005 | McFarlane |
| 2005/0256461 A1 | 11/2005 | DiFiore et al. |
| 2005/0261663 A1 | 11/2005 | Patterson et al. |
| 2005/0267400 A1 | 12/2005 | Haarala et al. |
| 2005/0277862 A1 | 12/2005 | Anand |
| 2005/0283111 A1 | 12/2005 | Maurice |
| 2005/0288623 A1 | 12/2005 | Hjalmarsson |
| 2005/0288706 A1 | 12/2005 | Widomski et al. |
| 2006/0004316 A1 | 1/2006 | Difiore et al. |
| 2006/0004325 A1 | 1/2006 | Hamatake et al. |
| 2006/0009783 A1 | 1/2006 | Rome et al. |
| 2006/0015072 A1 | 1/2006 | Raulerson |
| 2006/0015130 A1 | 1/2006 | Voorhees et al. |
| 2006/0030827 A1 | 2/2006 | Raulerson et al. |
| 2006/0047267 A1 | 3/2006 | Gately et al. |
| 2006/0047268 A1 | 3/2006 | Stephens |
| 2006/0058775 A1 | 3/2006 | Stevens et al. |
| 2006/0064072 A1 | 3/2006 | Gately et al. |
| 2006/0095062 A1 | 5/2006 | Stephens |
| 2006/0100572 A1 | 5/2006 | DiMatteo et al. |
| 2006/0111537 A1 | 5/2006 | Roby |
| 2006/0116629 A1 | 6/2006 | Tal et al. |
| 2006/0161100 A1 | 7/2006 | Hamboly |
| 2006/0184142 A1 | 8/2006 | Schon et al. |
| 2006/0189922 A1 | 8/2006 | Amarasinghe et al. |
| 2006/0200111 A1 | 9/2006 | Moehle et al. |
| 2006/0206094 A1 | 9/2006 | Chesnin et al. |
| 2006/0251612 A1 | 11/2006 | Kotzev et al. |
| 2006/0253063 A1 | 11/2006 | Schweikert |
| 2006/0271012 A1 | 11/2006 | Canaud et al. |
| 2007/0005003 A1 | 1/2007 | Patterson et al. |
| 2007/0019181 A1 | 1/2007 | Sinclair et al. |
| 2007/0066964 A1 | 3/2007 | Atkins |
| 2007/0078478 A1 | 4/2007 | Atkins et al. |
| 2007/0106206 A1 | 5/2007 | Appling |
| 2007/0129704 A1 | 6/2007 | O'Mahony et al. |
| 2007/0167925 A1 | 7/2007 | Jacqmein |
| 2007/0191810 A1 | 8/2007 | Kennedy |
| 2007/0225661 A1 | 9/2007 | Ash et al. |
| 2007/0225682 A1 | 9/2007 | Ash et al. |
| 2007/0282274 A1 | 12/2007 | Chesnin |
| 2008/0021417 A1 | 1/2008 | Zawacki et al. |
| 2008/0039774 A1 | 2/2008 | Zawacki et al. |
| 2008/0065029 A1 | 3/2008 | Racz |
| 2008/0082079 A1 | 4/2008 | Braga et al. |
| 2008/0082080 A1 | 4/2008 | Braga |
| 2008/0097409 A1 | 4/2008 | Stephens |
| 2008/0172012 A1 | 7/2008 | Hiniduma-Lokuge et al. |
| 2008/0214980 A1 | 9/2008 | Anand |
| 2008/0214992 A1 | 9/2008 | Haarala et al. |
| 2009/0112153 A1 | 4/2009 | Gregersen et al. |
| 2009/0118661 A1 | 5/2009 | Moehle et al. |
| 2009/0118701 A1 | 5/2009 | Nimkar et al. |
| 2009/0118707 A1 | 5/2009 | Schweikert et al. |
| 2009/0118755 A1 | 5/2009 | Maliglowka et al. |
| 2009/0138034 A1 | 5/2009 | Maliglowka et al. |
| 2009/0157051 A1 | 6/2009 | Appling et al. |
| 2009/0187141 A1 | 7/2009 | Lareau et al. |
| 2009/0192435 A1 | 7/2009 | Gregersen |
| 2009/0204052 A1 | 8/2009 | Nimkar et al. |
| 2009/0204079 A1 | 8/2009 | Nimkar et al. |
| 2009/0204083 A1 | 8/2009 | O'Donnell et al. |
| 2009/0205189 A1 | 8/2009 | Nimkar et al. |
| 2009/0209940 A1 | 8/2009 | Nimkar et al. |
| 2009/0292248 A1 | 11/2009 | Schon et al. |
| 2009/0312687 A1 | 12/2009 | DeFonzo et al. |
| 2010/0081986 A1 | 4/2010 | Matson et al. |
| 2010/0331780 A1 | 12/2010 | Bellisario et al. |
| 2011/0020418 A1 | 1/2011 | Bosley, Jr. et al. |
| 2011/0301522 A1 | 12/2011 | DeFonzo |
| 2012/0059304 A1 | 3/2012 | Gregersen et al. |
| 2012/0089070 A1 | 4/2012 | Moehle et al. |
| 2013/0018405 A1 | 1/2013 | Onishi et al. |
| 2013/0079752 A1 | 3/2013 | Gregersen |
| 2013/0253445 A1 | 9/2013 | Nimkar et al. |
| 2013/0261605 A1 | 10/2013 | Gregersen et al. |
| 2014/0018772 A1 | 1/2014 | Ash |
| 2014/0025042 A1 | 1/2014 | Gregersen |
| 2014/0088510 A1 | 3/2014 | Nimkar et al. |
| 2014/0228742 A1 | 8/2014 | Gregersen et al. |
| 2014/0276472 A1 | 9/2014 | VanderStek et al. |
| 2014/0276493 A1 | 9/2014 | Leung et al. |
| 2014/0277052 A1 | 9/2014 | Haselby et al. |
| 2014/0330220 A1 | 11/2014 | Zawacki et al. |
| 2014/0336687 A1 | 11/2014 | Iwase et al. |
| 2015/0073336 A1 | 3/2015 | Moehle et al. |
| 2015/0088100 A1 | 3/2015 | Oborn et al. |
| 2015/0335810 A1 | 11/2015 | Anand |
| 2017/0151418 A1 | 6/2017 | Nimkar et al. |
| 2019/0167888 A1 | 6/2019 | Gregersen |
| 2019/0240393 A1 | 8/2019 | Gregersen et al. |
| 2019/0240453 A1 | 8/2019 | Loesener et al. |

FOREIGN PATENT DOCUMENTS

| | | |
|---|---|---|
| CA | 2474351 A1 | 8/2003 |
| CN | 2788836 Y | 6/2006 |
| CN | 101918067 A | 12/2010 |
| CN | 103170050 A | 6/2013 |
| CN | 101918066 B | 7/2013 |
| DE | 8815869 U1 | 2/1989 |
| DE | 9108132 U1 | 9/1991 |
| DE | 102005051211 A1 | 5/2007 |
| EP | 0030854 A2 | 6/1981 |
| EP | 0132344 A2 | 1/1985 |
| EP | 0301854 | 2/1989 |
| EP | 0332366 A2 | 9/1989 |
| EP | 0386408 A1 | 9/1990 |
| EP | 0453234 A1 | 10/1991 |
| EP | 0476796 A1 | 3/1992 |
| EP | 0495263 A1 | 7/1992 |
| EP | 0650740 A1 | 5/1995 |
| EP | 0711574 A1 | 5/1996 |

(56) References Cited

FOREIGN PATENT DOCUMENTS

| | | |
|---|---|---|
| EP | 1471966 A1 | 11/2004 |
| EP | 1599247 A2 | 11/2005 |
| EP | 2305337 A2 | 4/2011 |
| GB | 1503469 | 3/1978 |
| JP | 56-136569 A | 10/1981 |
| JP | 8-510935 T | 11/1996 |
| JP | 2001137350 | 5/2001 |
| JP | 2008500081 A | 1/2008 |
| JP | 2011-502583 A | 1/2011 |
| JP | 4827377 B2 | 11/2011 |
| RU | 45923 A | 11/2004 |
| SU | 459237 A1 | 2/1975 |
| WO | 1991008132 A | 6/1991 |
| WO | 1993016741 A1 | 9/1993 |
| WO | 1993016752 A1 | 9/1993 |
| WO | 1997009086 A1 | 3/1997 |
| WO | 1997017102 | 5/1997 |
| WO | 1997022374 A1 | 6/1997 |
| WO | 1997037699 | 10/1997 |
| WO | 1999004844 A1 | 2/1999 |
| WO | 2000023137 A1 | 4/2000 |
| WO | 2002018004 A2 | 3/2002 |
| WO | 2002058776 A2 | 8/2002 |
| WO | 2002083223 A1 | 10/2002 |
| WO | 2003030960 A2 | 4/2003 |
| WO | 2003033049 A2 | 4/2003 |
| WO | 2003066148 A1 | 8/2003 |
| WO | 2004075962 A2 | 9/2004 |
| WO | 2004096334 | 11/2004 |
| WO | 2004112876 | 12/2004 |
| WO | 2005018712 A2 | 3/2005 |
| WO | 2005023336 A2 | 3/2005 |
| WO | 2005077449 | 8/2005 |
| WO | 2005084741 A1 | 9/2005 |
| WO | 2005118039 A1 | 12/2005 |
| WO | 2006034877 | 4/2006 |
| WO | 2008048183 A1 | 4/2008 |
| WO | WO-2008048183 A1 * | 4/2008 ........... A61B 5/0215 |
| WO | 2009051967 A1 | 4/2009 |
| WO | 2009055332 A1 | 4/2009 |
| WO | 2009059220 A1 | 5/2009 |
| WO | 2015077560 A1 | 5/2015 |
| WO | 2016/011091 A1 | 1/2016 |

OTHER PUBLICATIONS

*Arrow International, Inc. et al v. Spire Biomedical, Inc.*, U.S. Dist Ct Dist MA CA No. 06-CV-11564-DPW, Declaration of Dr. Karim Valji (Jul. 17, 2008).
*Arrow International, Inc. et al v. Spire Biomedical, Inc.*, U.S. Dist Ct Dist MA CA No. 06-CV-11564-DPW, Declaration of Kenneth Todd Cassidy (Jul. 16, 2008).
*Arrow International, Inc. et al v. Spire Biomedical, Inc.*, U.S. Dist Ct Dist MA CA No. 06-CV-11564-DPW, Declaration of Rebecca R. Eisenberg in Opposition to Defendant's Motion for Partial Summary Judgment of Invalidity (Jun. 8, 2009).
*Arrow International, Inc. et al v. Spire Biomedical, Inc.*, U.S. Dist Ct Dist MA CA No. 06-CV-11564-DPW, Memorandum of Law in Support of Defendant's Motion for Summary Judgment on Invalidity [Redacted Pursuant to Jun. 10, 2008 Order on Motion to Seal].
*Arrow International, Inc. et al v. Spire Biomedical, Inc.*, U.S. Dist Ct Dist MA CA No. 06-CV-11564-DPW, Memorandum of Law in Support of Defendants Motion for Summary Judgment on Invalidity Exhibit A (Jul. 10, 2009).
*Arrow International, Inc. et al v. Spire Biomedical, Inc.*, U.S. Dist Ct Dist MA CA No. 06-CV-11564-DPW, Plaintiff's Memorandum in Opposition to Defendants Motion for Summary Judgement on Non-Infringement (Jul. 17, 2008).
*Arrow International, Inc. et al. v. Spire Biomedical, Inc.*, U.S. Dist. Ct. Dist. MA CA No. 06-CV-11564-DPW, Defendant's Omnibus Statement of Material Facts in Support of its Motions for Summary Judgment (Jun. 10, 2008) [Redacted Pursuant to Jun. 10, 2008 Order on Motion to Seal].

Bander, et al., Central Venous Angioaccess for Hemodialysis and Its Complications, Seminars in Dialysis, 1992, vol. 5, No. 2, pp. 121-128.
Baranowski, L., Central Venous Access Devices, Journal of Intravenous Nursing, 1993, vol. 16, No. 3, pp. 167-194.
BARD Access Systems Hickman®, Leonard®, and Broviac® Central Venous Catheters (Long Term), Instructions for Use, 31 pages, 1999.
BARD Access Systems Hickman®, Leonard®, and Broviac® Central Venous Catheters, Nursing Procedural Manual, 52 pages, Jun. 1994.
BARD Davol® Hickman® Round Dual Lumen Catheters for Central Venous Access Informational Brochure, 4 pages, 1994.
BARD Hickman® Catheters Informational Brochure, 3 pages, 1994.
Believed to be an unpublished sketch of a conception by Dr. John Frusha; date of sketch believed to be Jun. 24, 1997.
Berkoben, et al., Maintenance of Permanent Hemodialysis Vascular Access Patency, ANNA Journal, 1995, vol. 22, No. 1, pp. 17-24.
Bolz, et al., Catheter Malfunction and Thrombus Formation on Double-Lumen Hemodialysis Catheters: An Intravascular Ultrasonographic Study, American Journal of Kidney Diseases, 1995, vol. 25, No. 4, pp. 597-602.
Bour, et al., Experience With the Double Lumen Silastic® Catheter for Hemoaccess, Surgery, Gynecology & Obstetrics, 1990, vol. 171, pp. 33-39.
Camp, "Care of the Groshong Catheter", Oncol Nurs Forum, vol. 15, No. 6, 1988.
Campbell, et al., Radiological Insertion of Long-term Venous Access Devices, Seminars in Interventional Radiology, 1994, vol. II, No. 4, pp. 366-375.
Cannaud, B et al, Permenant Twin Catheter: A Vascular Access Option of Choice for Haemodialysis in Elderly Patients, pp. 82-88, vol. 17 No. 7, 1994.
Claim Construction Order of Federal District Court dated May 9, 2003 in *Thierry Pourchez and Bard Access Systems, Inc. v. Diatek, Inc. and Arrow International, Inc.* litigation (S.D. N.Y. 03 Civ. 0972).
Claim Construction Order of Federal District Court dated Oct. 31, 2006 in *Arrow Int'l. Inc.and Arrow Int'l. Investment Corp. v. Spire Biomedical, Inc.* litigation (D. Mass. Civil Action No. 06-CV-11564).
CN 200880121182.0 filed Oct. 20, 2008 First Office Action dated May 2, 2012.
CN 200880121183.5 filed Oct. 2, 2008 First Office Action dated Mar. 28, 2012.
CN 200880121183.5 filed Oct. 2, 2008 Second Office Action dated Aug. 17, 2012.
CN 200880121183.5 filed Oct. 2, 2008 Third Office Action dated Dec. 11, 2012.
CN 200880123095.9 filed Oct. 20, 2008 First Office Action dated Feb. 13, 2012.
CB 200880123095.9 filed Oct. 20, 2008 Second Office Action dated Dec. 18, 2012.
CB 200880123533.1 filed Jun. 30, 2008 First Office Action dated May 28, 2012.
CB 200880123533.1 filed Jun. 30, 2008 Notice of Grant dated Dec. 24, 2012.
CB 201310073124.8 filed Mar. 7, 2013 First Office Action dated May 5, 2014.
Decision of Federal District Court dated Jul. 7, 2009 granting Summary Judgement of Invalidity in *Arrow Int'l. Inc. and Arrow Int'l Investment Corp. v. Spire Biomedical, Inc.* litigation (D. Mass. Civil Action No. 06-CV-11564).
Declaration of Gregory S. Haas (Plaintiff's Exhibit 88 in Haas Deposition), Mar. 13, 2003, *Thierry Pourchez and Bard Access Systems, Inc. v. Diatek, Inc. and Arrow International, Inc.*, Civil Action No. 03-CV-0972 (S.D.N.Y.).
Defendant's Exhibits DX78-DX114, *Thierry Pourchez and Bard Access Systems, Inc. v. Diatek, Inc. And Arrow International, Inc.*, Civil Action No. 03-CV-0972 (S.D.N.Y.), 2003.
Defendants' Reponses and Objections to Plaintiffs' Second Set of Interrogatories (Excerpt), *Thierry Pourchez and Bard Access Sys-*

(56) References Cited

OTHER PUBLICATIONS

*tems, Inc.* v. *Diatek, Inc. and Arrow International, Inc.*, Civil Action No. 03-CV-0972 (S.D.N.Y.) (Oct. 8, 2003).
Delmore et al., "Experience with the Groshong Long-Term Central Venous Catheter", Gynecologic Oncology 34, 216-218 (1989).
Dialysis Vascular Access, SchonXL® Temporary Dialysis (AngioDynamics Inc.) brochure, Nov. 1998.
Dialysis Vascular Access, Technological Innovations Improving Flow (AngioDynamics Inc.) Brochure, 4 pages, Nov. 1998.
Difiore, "Central Venous Dialysis Catheter Evaluatio in Swine", Journal of Vascular Access Devices, Fall 2000.
Donaldson, et al., Peripherally Inserted Central Venous Catheters: US-guided Vascular Access in Pediatric Patients1, Radiology, 1995, vol. 197, pp. 542-544.
Dunea, et. al., A Survey of Permanent Double Lumen Catheters in Hemodialysis Patients. ASAIO Transac. 1991; 37: M276-7.
Dupont et al, Long-term development of Permacath Quinton catheters used as a vascular access route for extra-renal detoxification; Néphrologie, vol. 15, pp. 105-110, 1994.
EP 04712925.9 filed Feb. 19, 2004 Office Action dated Nov. 7, 2008.
EP 08839196.6 filed Oct. 2, 2008 Examination Report dated Jan. 16, 2013.
EP 08839196.6 filed Oct. 2, 2008 Search Opinion dated Jul. 12, 2011.
EP 08839196.6 filed Oct. 2, 2008 Search Report dated Jul. 12, 2011.
EP 08872340.8 filed Oct. 2, 2008 Extended European Search Report and an Opinion dated Apr. 19, 2012.
Gallichio, et al., Placement of a Double Lumen Silastic Catheter for Hemodialysis Access Through the Cephalic Vein, Journal of the American College of Surgeons, 1994, vol. 179, pp. 171-172.
Gravenstein, et al., In Vitro Evaluation of Relative Perforating Potential of Central Venous Catheters: Comparison of Materials, Selected Models, Number of Lumens, and Angles of Incidence to Simulated Membrane, Journal of Clinical Monitoring, 1991, vol. 7, pp. 1-6.
PCT/US2008/078551 filed Oct. 2, 2008 Search Report dated Mar. 13, 2009.
PCT/US2008/078551 filed Oct. 2, 2008 Written Opinion dated Mar. 13, 2009.
PCT/US2008/078560 filed Oct. 2, 2008 Preliminary Report on Patentability dated Aug. 26, 2010.
PCT/US2008/078560 filed Oct. 2, 2008 Search Report dated Mar. 16, 2009.
PCT/US2008/078560 filed Oct. 2, 2008 Written Opinion dated Mar. 16, 2009.
PCT/US2008/078566 filed Oct. 2, 2008 International Preliminary Report on Patentability dated Apr. 20, 2010.
PCT/US2008/078566 filed Oct. 2, 2008 Search Report dated Mar. 19, 2009.
PCT/US2008/078566 filed Oct. 2, 2008 Written Opinion dated Mar. 19, 2009.
PCT/US2008/078571 filed Oct. 2, 2008 Preliminary Report on Patentability dated Aug. 26, 2010.
PCT/US2008/078571 filed Oct. 2, 2008 Search Report dated Mar. 20, 2009.
PCT/US2008/078571 filed Oct. 2, 2008 Written Opinion dated Mar. 20, 2009.
PCT/US2008/080463 filed Oct. 20, 2008 Preliminary Report on Patentability dated Apr. 27, 2010.
PCT/US2008/080463 filed Oct. 20, 2008 Search Report dated Mar. 16, 2009.
PCT/US2008/080463 filed Oct. 20, 2008 Written Opinion dated Apr. 16, 2009.
PCT/US2008/082106 filed Oct. 31, 2008 International Preliminary Report on Patentability dated May 4, 2010.
PCT/US2008/082106 filed Oct. 31, 2008 Search Report dated Jan. 12, 2009.
PCT/US2008/082106 filed Oct. 31, 2008 Written Opinion dated Jan. 12, 2009.
PCT/US2014/066811 filed Nov. 21, 2014 International Search Report and Written Opinion dated Apr. 15, 2015.
Picture of Device believed to be partial sample of a product believed to have been sold in the United States with Polycath and/or Infuse-a-Cath Instructions for Use, 1 page, 2011.
QUINTON® Catheter Products (1993).
Raaf Dual Lumen Right Atrial Catheters Brochure—Quinton Instrument Co., 6 pages, 1993.
Raaf, et al., Open Insertion of Right Atrial Catheters Through the Jugular Veins, Surgery, Gynecology & Obstetrics, 1993, vol. 177, pp. 295-298.
Rawn, et al., The Hemodialysis Access, Chapter 9, pp. 9.1-9.11, available at <<http://msl1.mit.edu/ESD10/kidneys/HndbkPDF/Chap09.pdf>>, last accessed Jun. 4, 2012.
Schwab, et al., Prospective Evaluation of a Dacron Cuffed Hemodialysis Catheter for Prolonged Use, American Journal of Kidney Diseases, 1988, vol. XI, No. 2, pp. 166-169.
Schwab, et al., Vascular Access: Case Oriented Discussions of Selected Critical Issues: Hemodialysis Catheters for Permanent Use, 1999.
Septum, Wikipedia, The Free Encyclopedia, hhttp://en.wikipedia.org/wiki/Septum (last visited Dec. 18, 2012) (defining "septum" as "a wall, dividing a cavity or structure into smaller ones").
Shaffer, D., Catheter-Related Sepsis Complicating Long-Term Tunnelled Central Venous Dialysis Catheters: Management by Guidewire Exchange, American Journal of Kidney Diseases, 1995, vol. 25, No. 4, pp. 593-596.
Shaffer, D., Lessons From Vascular Access Procedures for Hemodialysis, Surgical Oncology Clinics of North America, 1995, vol. 4, No. 3, pp. 537-549.
Sioshansi, P., New Processes for Surface Treatment of Catheters, Artificial Organs, 1994, 18(4):266-271.
Swartz, et al., Successful Use of Cuffed Centrol Venous Hemodialysis Catheters Inserted Percutaneously, J. Am. Soc. Nephrol., 1994, 4:1719-1725.
Taber's Cyclopedic Medical Dictionary 1662 (16th ed. 1989) (defining "septum" as a "wall dividing two cavities").
Tal, Michael G, Comparison of Recirculation Percentage of the Palindrome Catheter and Standard Hemodialysis Catheters in a Swine Model, J Vasc Interv Radiol, pp. 1237-1240, vol. 16, No. 9, 2005.
Tesio, et al., Double Catheterization of the Internal Jugular Vein for Hemodialysis: Indications, Techniques, and Clinical Results, Artificial Organs, 1994, vol. 18, No. 4, pp. 301-304.
The Groshong™ Peripherally Inserted Central Venous Catheter Brochure—Cath-tech®, 4 pages, 1988.
Transcript of Videotaped Deposition of Gregory Haas (Excerpt), Sep. 23, 2003, *Thierry Pourchez and Bard Access Systems, Inc.* v. *Diatek, Inc. and Arrow International, Inc.*, Civil Action No. 03-CV-0972 (S.D.N.Y.).
Transcript of Videotaped Deposition of Thierry Pourchez, vol. 1, Oct. 16, 2003, *Thierry Pourchez and Bard Access Systems, Inc.* v. *Diatek, Inc. and Arrow International, Inc.*, Civil Action No. 03-CV-0972 (S.D.N.Y.).
Transcript of Videotaped Deposition of Thierry Pourchez, vol. 2, Oct. 17, 2003, *Thierry Pourchez and Bard Access Systems, Inc.* v. *Diatek, Inc. and Arrow International, Inc.*, Civil Action No. 03-CV-0972 (S.D.N.Y.).
Treiman, et al., Chronic Venous Access in Patients with Cancer, Cancer, 1993, vol. 72, No. 3, pp. 760-765.
Twardowski et al. "Side Holes at the Tip of Chronic Hemodialysis Catehters are Harmful," The Journal of Vascular Access 2001; 2:8-16.
Twardowski et al., "Blood Recirculation in Intravenous Catheters for Hemodialysis" J. Am. Soc. Nephrol. 3:1978-81 (1993).
TYCO Healthcare, Mahurkar Dual Lumen Catheters, Informational Brochure, 2 pages, 2004.
TYCO Healthcare, Mahurkar QPlus High Flow Acute Care Catheter, Informational Brochure, 2 pages, 2004.
TYCO Healthcare, Tal Palindrome™ Dual Lumen Catheters Order Information, Features and Benefits, Frequently Asked Questions, printed from http://www.kendallvasculartherapy.com/VascularTherapy, 6 pages, on Mar. 1, 2007.

(56) References Cited

OTHER PUBLICATIONS

Uldall, P., Subclavian Cannulation is no Longer Necessary or Justified in Patients with End-Stage Renal Failure, Seminars in Dialysis, 1994, vol. 7, No. 3, pp. 161-164.
U.S. Appl. No. 10/371,774, filed Feb. 21, 2003 Final Office Action dated Jan. 19, 2007.
U.S. Appl. No. 10/371,774, filed Feb. 21, 2003 Final Office Action dated Mar. 7, 2007.
U.S. Appl. No. 10/371,774, filed Feb. 21, 2003 Non-Final Office Action dated Jul. 17, 2006.
U.S. Appl. No. 10/371,774, filed Feb. 21, 2003 Notice of Allowance dated Jun. 1, 2007.
U.S. Appl. No. 10/445,731, filed May 27, 2003 Non-Final Office Action dated Apr. 13, 2007.
U.S. Appl. No. 10/445,731, filed May 27, 2003 Non-Final Office Action dated Dec. 12, 2008.
EP 14864273.9 filed May 20, 2016 Extended European Search Report dated Jun. 9, 2017.
EP 14864273.9 filed May 20, 2016 Partial European Search Report dated Jun. 9, 2017.
U.S. Appl. No. 13/897,292, filed May 17, 2013 Decision on Appeal dated Jun. 8, 2017.
U.S. Appl. No. 13/897,292, filed May 17, 2013 Notice of Allowance dated Aug. 23, 2017.
U.S. Appl. No. 14/675,236, filed Mar. 31, 2015 Notice of Allowance dated May 16, 2017.
U.S. Appl. No. 12/244,514, filed Oct. 2, 2008 Non-Final Office Action dated Jan. 19, 2011.
U.S. Appl. No. 12/244,544, filed Oct. 2, 2008 Final Office Action dated Jul. 11, 2011.
U.S. Appl. No. 12/244,544, filed Oct. 2, 2008 Non-Final Office Action dated Dec. 22, 2010.
U.S. Appl. No. 12/244,554, filed Oct. 2, 2008 Final Office Action dated Dec. 27, 2010.
U.S. Appl. No. 12/244,554, filed Oct. 2, 2008 Non-Final Office Action dated Jul. 6, 2010.
U.S. Appl. No. 12/253,870, filed Oct. 17, 2008 Non-Final Office Action dated Jan. 21, 2011.
U.S. Appl. No. 12/253,870, filed Oct. 17, 2008 Notice of Allowance dated Aug. 19, 2011.
U.S. Appl. No. 12/262,820, filed Oct. 31, 2008 Non-Final Office Action dated Feb. 18, 2011.
U.S. Appl. No. 12/262,820, filed Oct. 31, 2008 Notice of Allowance dated Sep. 28, 2011.
U.S. Appl. No. 12/263,141, filed Oct. 31, 2008 Advisory Action dated Aug. 17, 2011.
U.S. Appl. No. 12/263,141, filed Oct. 31, 2008 Final Office Action dated May 26, 2011.
U.S. Appl. No. 12/263,141, filed Oct. 31, 2008 Non-Final Office Action dated Jan. 5, 2011.
U.S. Appl. No. 12/414,467, filed Mar. 30, 2009 Final Office Action dated Feb. 7, 2012.
U.S. Appl. No. 12/414,467, filed Mar. 30, 2009 Notice of Allowance dated May 31, 2012.
U.S. Appl. No. 12/414,467, filed Mar. 30, 2009 Non-Final Office Action dated Aug. 11, 2011.
U.S. Appl. No. 13/294,941, filed Nov. 11, 2011 Non-Final Office Action dated May 27, 2016.
U.S. Appl. No. 13/294,941, filed Nov. 11, 2011 Non-Final Office Action dated May 31, 2013.
U.S. Appl. No. 13/294,941, filed Nov. 11, 2011 Notice of Allowance dated Nov. 27, 2013.
U.S. Appl. No. 13/329,156, filed Dec. 16, 2011 Non-Final Office Action dated May 16, 2014.
U.S. Appl. No. 13/445,713, filed Apr. 12, 2012 Advisory Action dated Aug. 8, 2013.
U.S. Appl. No. 13/445,713, filed Apr. 12, 2012 Final Office Action dated May 30, 2013.
U.S. Appl. No. 13/445,713, filed Apr. 12, 2012 Non-Final Office Action dated Jan. 2, 2013.
U.S. Appl. No. 13/445,713, filed Apr. 12, 2012 Notice of Allowance dated Oct. 18, 2013.
U.S. Appl. No. 13/897,292, filed May 17, 2013 Final Office Action dated Apr. 9, 2015.
U.S. Appl. No. 13/897,292, filed May 17, 2013 Non-Final Office Action dated Nov. 20, 2014.
U.S. Appl. No. 14/032,858, filed Sep. 20, 2013 Final Office Action dated Mar. 31, 2015.
U.S. Appl. No. 14/032,858, filed Sep. 20, 2013 Non-Final Office Action dated Nov. 4, 2014.
U.S. Appl. No. 14/032,858, filed Sep. 20, 2013, Notice of Allowance dated Jun. 26, 2015.
U.S. Appl. No. 14/094,534, filed Dec. 2, 2013 Final Office Action dated Jul. 20, 2016.
U.S. Appl. No. 14/094,534, filed Dec. 2, 2013 Non-Final Office Action dated Feb. 24, 2016.
U.S. Appl. No. 14/094,534, filed Dec. 2, 2013 Notice of Allowance dated Sep. 30, 2016.
U.S. Appl. No. 14/252,567, filed Apr. 14, 2014 Non-Final Office Action dated Mar. 31, 2015.
U.S. Appl. No. 14/252,567, filed Apr. 14, 2014 Notice of Allowance dated Sep. 3, 2015.
U.S. Appl. No. 14/328,541, filed Jul. 10, 2014 Final Office Action dated Oct. 22, 2015.
U.S. Appl. No. 14/328,541, filed Jul. 10, 2014 Non-Final Office Action dated Apr. 9, 2015.
U.S. Appl. No. 14/542,495, filed Nov. 14, 2014 Final Office Action dated Aug. 31, 2016.
U.S. Appl. No. 14/542,495, filed Nov. 14, 2014 Non-Final Office Action dated May 10, 2016.
U.S. Appl. No. 14/542,495, filed Nov. 14, 2014 Notice of Allowance dated Nov. 15, 2016.
U.S. Appl. No. 14/675,236, filed Mar. 31, 2015 Non-Final Office Action dated Feb. 2, 2017.
US Patent File History U.S. Pat. No. 5,403,291 (Abrahamson), issued Apr. 4, 1995.
US Patent File History U.S. Pat. No. 5,489,278 (Abrahamson), issued Feb. 6, 1996.
US Patent File History U.S. Pat. No. 5,685,867 (Twardowski et al.), issued Nov. 11, 1997.
Wechsler, et al., Thrombosis and Infection Caused by Thoracic Venous Catheters: Pathogenesis and Imagings Findings, AJR, 1993; 160:467-471.
Weitzel, et al., Successful Use of Indwelling Cuffed Femoral Vein Catheters in Ambulatory Hemodialysis Patients, American Journal of Kidney Diseases, 1993, vol. 22, No. 3, pp. 426-429.
JP 2016-533038 filed May 20, 2016 Office Action dated Oct. 11, 2018.
U.S. Appl. No. 14/799,547, filed Jul. 14, 2015 Non-Final Office Action dated Mar. 16, 2018.
U.S. Appl. No. 14/799,547, filed Jul. 14, 2015 Restriction Requirement dated Nov. 30, 2017.
U.S. Appl. No. 14/930,526, filed Nov. 2, 2015 Final Office Action dated Jun. 7, 2018.
U.S. Appl. No. 14/930,526, filed Nov. 2, 2015 Non-Final Office Action dated Feb. 23, 2016.
U.S. Appl. No. 14/930,526, filed Nov. 2, 2015 Notice of Allowance dated Oct. 2, 2018.
U.S. Appl. No. 14/991,858, filed Jan. 8, 2016 Non-Final Office Action dated May 17, 2018.
U.S. Appl. No. 14/991,858, filed Jan. 8, 2016 Notice of Allowance dated Nov. 26, 2018.
U.S. Appl. No. 15/429,049, filed Feb. 9, 2017 Non-Final Office Action dated Mar. 20, 2018.
U.S. Appl. No. 15/429,049, filed Feb. 9, 2017 Notice of Allowance dated May 31, 2018.
U.S. Appl. No. 10/445,731, filed May 27, 2003 Non-Final Office Action dated May 30, 2008.
U.S. Appl. No. 10/842,586, filed May 10, 2004 Advisory Action dated Oct. 9, 2008.
U.S. Appl. No. 10/842,586, filed May 10, 2004 Final Office Action dated Jul. 29, 2008.

(56) References Cited

OTHER PUBLICATIONS

U.S. Appl. No. 10/842,586, filed May 10, 2004 Final Office Action dated May 25, 2010.
U.S. Appl. No. 10/842,586, filed May 10, 2004 Non-Final Office Action dated Jan. 7, 2008.
U.S. Appl. No. 10/842,586, filed May 10, 2004 Non-Final Office Action dated Jun. 16, 2009.
U.S. Appl. No. 10/842,586, filed May 10, 2004 Non-Final Office Action dated Nov. 13, 2008.
U.S. Appl. No. 10/842,586, filed May 10, 2004 Non-Final Office Action dated Nov. 23, 2009.
U.S. Appl. No. 10/874,298, filed Jun. 9, 2004 Advisory Action dated Feb. 19, 2009.
U.S. Appl. No. 10/874,298, filed Jun. 9, 2004 Final Office Action dated Jul. 15, 2008.
U.S. Appl. No. 10/874,298, filed Jun. 9, 2004 Final Office Action dated Jul. 7, 2010.
U.S. Appl. No. 10/874,298 filed Jun. 9, 2004 Final Office Action dated Mar. 18, 2014.
U.S. Appl. No. 10/874,298, filed Jun. 9, 2004 Non-Final Office Action dated Aug. 1, 2013.
U.S. Appl. No. 10/874,298, filed Jun. 9, 2004 Non-Final Office Action dated Aug. 18, 2011.
U.S. Appl. No. 10/874,298, filed Jun. 9, 2004 Non-Final Office Action dated Dec. 30, 2009.
U.S. Appl. No. 10/874,298, filed Jun. 9, 2004 Non-Final Office Action dated Feb. 2, 2011.
U.S. Appl. No. 10/874,298, filed Jun. 9, 2004 Non-Final Office Action dated Jul. 23, 2009.
U.S. Appl. No. 10/874,298, filed Jun. 9, 2004 Non-Final Office Action dated Jul. 9, 2014.
U.S. Appl. No. 10/874,298, filed Jun. 9, 2004 Non-Final Office Action dated May 23, 2006.
U.S. Appl. No. 10/874,298, filed Jun. 9, 2004 Non-Final Office Action dated May 24, 2007.
U.S. Appl. No. 11/859,106, filed Sep. 21, 2007 Final Office Action dated Sep. 1, 2009.
U.S. Appl. No. 11/859,106, filed Sep. 21, 2007 Non-Final Office Action dated Feb. 5, 2009.
U.S. Appl. No. 11/859,106, filed Sep. 21, 2007 Non-Final Office Action dated Mar. 30, 2011.
U.S. Appl. No. 11/859,106, filed Sep. 21, 2007 Non-Final Office Action dated Jun. 25, 2008.
U.S. Appl. No. 11/874,447, filed Oct. 18, 2007 Decision on Appeal dated Dec. 26, 2012.
U.S. Appl. No. 11/874,447, filed Oct. 18, 2007 Examiner's Answer dated Apr. 28, 2010.
U.S. Appl. No. 11/874,447, filed Oct. 18, 2007 Final Office Action dated Jul. 22, 2009.
U.S. Appl. No. 11/874,447, filed Oct. 18, 2007 Non-Final Office Action dated Jan. 6, 2009.
U.S. Appl. No. 11/874,447, filed Oct. 18, 2007 Non-Final Office Action dated Jul. 12, 2013.
U.S. Appl. No. 11/874,447, filed Oct. 18, 2007 Non-Final Office Action dated Jul. 9, 2008.
U.S. Appl. No. 11/874,447, filed Oct. 18, 2007 Notice of Allowance dated Apr. 18, 2014.
U.S. Appl. No. 12/048,871, filed Mar. 14, 2008 Decision on Appeal dated Feb. 2, 2015.
U.S. Appl. No. 12/048,871, filed Mar. 14, 2008 Examiner's Answer dated Feb. 9, 2012.
U.S. Appl. No. 12/048,871, filed Mar. 14, 2008 Final Office Action dated Jan. 20, 2011.
U.S. Appl. No. 12/048,871, filed Mar. 14, 2008 Final Office Action dated Jan. 4, 2016.
U.S. Appl. No. 12/048,871, filed Mar. 14, 2008 Non-Final Office Action dated Aug. 31, 2016.
U.S. Appl. No. 12/048,871, filed Mar. 14, 2008 Non-Final Office Action dated Jan. 7, 2010.
U.S. Appl. No. 12/048,871, filed Mar. 14, 2008 Non-Final Office Action dated Jul. 16, 2015.
U.S. Appl. No. 12/048,871, filed Mar. 14, 2008 Non-Final Office Action dated Jul. 7, 2010.
U.S. Appl. No. 12/048,871, filed Mar. 14, 2008 Non-Final Office Action dated May 12, 2009.
U.S. Appl. No. 12/048,871, filed Mar. 14, 2008 Notice of Allowance dated Feb. 10, 2017.
U.S. Appl. No. 12/244,514, filed Oct. 2, 2008 Final Office Action dated Jun. 19, 2012.
U.S. Appl. No. 12/244,514, filed Oct. 2, 2008 Non-Final Office Action dated Jan. 17, 2012.
U.S. Appl. No. 12/244,559, filed Oct. 2, 2008 Decision on Appeal dated Aug. 31, 2015.
U.S. Appl. No. 12/244,559, filed Oct. 2, 2008 Examinees Answer dated Mar. 27, 2013.
U.S. Appl. No. 12/244,559, filed Oct. 2, 2009 Final Office Action dated Jul. 3, 2012.
U.S. Appl. No. 12/244,559, filed Oct. 2, 2009 Non-Final Office Action dated Mar. 14, 2012.
U.S. Appl. No. 12/244,514, filed Oct. 2, 2008 Advisory Action dated Sep. 5, 2012.
U.S. Appl. No. 12/244,514, filed Oct. 2, 2008 Final Office Action dated Jul. 11, 2011.
Haindl, H., Technical complications of port-catheter systems, Reg. Cancer Treat, 1989, 2:238-242.
Haire, et al., Thrombotic Complications of Subclavian Apheresis catheters in Cancer Patients: Prevention With Heparin Infusion, Journal of Clinical Apheresis, 1990, vol. 5, pp. 188-191.
Hull, et al., The Groshong Catheter: Initial Experience and Early Results of Imaging-guided Placement1, Radiology, 1992, vol. 185, pp. 803-807.
Ignotus, et al., Review of Radiological Insertion of Indwelling Central Venous Catheters, Minimally Invasive Therapy, 1992, 1:373-388.
Instructions for Use (Copyright Dated 1990) for Polycath Polyurethance Central Venous Catheter; believed to have been packaged with product and sold in the United States before Jan. 4, 2000 and with related marketing materials.
Instructions for Use (Copyright Dated 1992) for FloLock Single Lumen Bi-directional Valved Catheter; believed to have been packaged with product and sold in the United States before Jan. 2000.
Instructions for Use (not dated) for Infuse-a-Cath Polyurethance Central Venous Catheter; believed to have been packaged with product and sold in the United States before Jan. 2000.
Instructions for Use for Diatek Cannon Catheter Product First Sold in the United States in Sep. 2001.
Jones, et al., Efficacy of the Supraclavicular Route for Temporary Hemodialysis Access, Southern Medical Journal, 1992, vol. 85, No. 7, pp. 725-726.
JP 2010-532299 filed Apr. 30, 2010 Final Notice of Reason for Rejection dated Feb. 8, 2013.
JP 2010-532299 filed Apr. 30, 2010 Official Action dated Apr. 23, 2012.
JP App. No. 2003-565569 filed Feb. 7, 2003, Translated Decision of Refusal dated Dec. 24, 2009.
JP App. No. 2003-565569 filed Feb. 7, 2003, Translated Official Action dated May 28, 2009.
JP App. No. 2003-565569 filed Feb. 7, 2003, Translated Official Action dated Nov. 7, 2008.
Kapoian et al. Dialysis as Treatment of End-Stage Renal Disease, Chapter 5: Dialysis Access and Recirculation, © 1999.
Kaupke, et al., Perforation of the Superior Vena Cava by a Subclavian Hemodialysis Catheter: early detection by angiography, The International Journal of Artificial Organs, 1992, vol. 15, No. 11, pp. 666-668.
Kelber, et al., Factors Affecting Delivery of High-Efficiency Dialysis Using Temporary Vascular Access, American Journal of Kidney Diseases, 1993, vol. 22, No. 1, pp. 24-29.
Lubrizol, "Lubrizol's Family of TPUs" Brochure (2005), 9 pages.
Lumsden, et al., Hemodialysis Access in the Pediatric Patient Population, The American Journal of Surgery, 1994, vol. 168, pp. 197.

(56) References Cited

OTHER PUBLICATIONS

Lund, "Percutaneous Translumbar Inferior Vena Cava Cannulation and other Alternative Vascular Access Techniques" in Venous Interventional Radiology with Clinical Perspectives, Savader et al, eds. pp. 251-261, Apr. 10, 2000.
Lund, et al., Percutaneous Translumbar Inferior Vena Cava Cannulation for Hemodialysis, American Journal of Kidney Diseases, 1995, vol. 25, No. 5, pp. 732-737.
Maki, D., Pathogenesis, Prevention, and Management of Infections Due to Intravascular Devices Used for Infusion Therapy, in Infections Associated with Indwelling Medical Devices, Bisno et al, eds, American Society for Microbiology, 1989, pp. 161-177.
Malviya et al., "Vascular Access in Gynecological Cancer Using the Groshong Right Atrial Catheter", Gynecological Oncology 33, 313-316 (1989).
Mauro, et al., Radiologic Placement of Long-term Central Venous Catheters: A Review, JVIR, 1993, vol. 4, No. 1, pp. 127-137.
Mcgee, et al., Accurate placement of central venous catheters: A prospective, randomized, multicenter trial, Critical Care Medicine, 1993, vol. 21, No. 8, pp. 1118-1123.
Medcomp, For Access via the Internal Jugular Vein . . . The Medcomp TESIO Catheter is the Solution: The Short and Long Term Solution to Subclavian Venin Stenosis and Difficult Access Problems, Brochure, 4 pages, 1991.
Medcomp® Brochure , "Ash Split Cath™ XL", Dec. 2001, PN 2291.
Medcomp® Brochure , "Ash Split Cath™", Guidewire Weave Insertion Technique, Jan. 2002, PN 2296.
Medcomp® Brochure , "Ash Split Cath™", Jul. 2001, PN 2114.
Medcomp® Brochure , "Ash Split Cath™", Nov. 1997, PN 2050.
Medcomp® Brochure , "Ash Split Cath® II", Aug. 2002, PN 2334.
Medcomp® Brochure , "Magna™ High Flow Catheter", Mar. 2002, PN 2321.
Moss et al, Use of Silicone Dual-Lumen Catheter with a Dacron Cuff as a Long Term Vascular Access for Hemodialysis Patients, Amer J Kidney Diseases, vol. XVI, No. 3, pp. 211-215, Sep. 1990.
Moss, et al., Use of a Silicone Catheter With a Dacron Cuff for Dialysis Short-Term Vascular Access, American Journal of Kidney Diseases, 1988, vol. XII, No. 6, pp. 492-498.
Myers, R.D. et al, New Double-lumen Polyethylene Cannula for Push-pull Perfusion of Brain Tissue in Vivo, Journal of Neuroscience Methods, pp. 205-218, vol. 12, 1985.
Northsea, C., Using Urokinase to Restore Patency in Double Lumen Catheters, ANNA Journal 1994, vol. 21, No. 5, pp. 261-273.
OriGen, OriGen Biomedical Dual Lumen Catheter, from <http://origen.net/catheter.html>, downloaded May 13, 2009, 4 pages (reprinted for submission on Jul. 21, 2011).
Parsa, et al., Establishment of Intravenous Lines for Long-term Intravenous Therapy and Monitoring, Surgical Clinics of N. Am. 1985, vol. 65, No. 4, pp. 835-865.
Parsa, et al., Vascular Access Techniques, Textbook of Critical Care, W.B. Saunders, Philadelphia, PA (1989), pp. 122-127.
Pasquale, et al., Groshong® Versus Hickman® Catheters, Surgery, Gynecology & Obstetrics, 1992, vol. 174, pp. 408-410.
Passaro, et al., Long-term Silastic Catheters and Chest Pain, Journal of Parenteral and Enteral Nutrition, 1994, vol. 18, No. 3, pp. 240-242.
Patel et al., "Sheathless Technique of Ash Split-Cath Insertion", 12 JVIR 376-78 (Mar. 2001).
Paulsen, et al., Use of Tissue Plasminogen Activator for Reopening of Clotted Dialysis Catheters, Nephron, 1993, vol. 64, pp. 468-470.
PCT/US15/40463 filed Jul. 14, 2015 International Search Report and Written Opinion dated Dec. 18, 2015.
PCT/US2003/003751 filed Feb. 7, 2003 Preliminary Examination Report dated May 5, 2004.
PCT/US2003/003751 filed Feb. 7, 2003 Search Report dated Jul. 3, 2003.
PCT/US2004/005102 filed Feb. 19, 2004 Preliminary Report Patenability dated Aug. 29, 2005.
PCT/US2004/005102 filed Feb. 19, 2004 Search Report dated Dec. 27, 2004.
PCT/US2004/005102 filed Feb. 29, 2004 Written Opinion dated Aug. 21, 2005.
PCT/US2008/078551 filed Oct. 2, 2008 International Preliminary Report on Patentability dated Apr. 20, 2010.

* cited by examiner

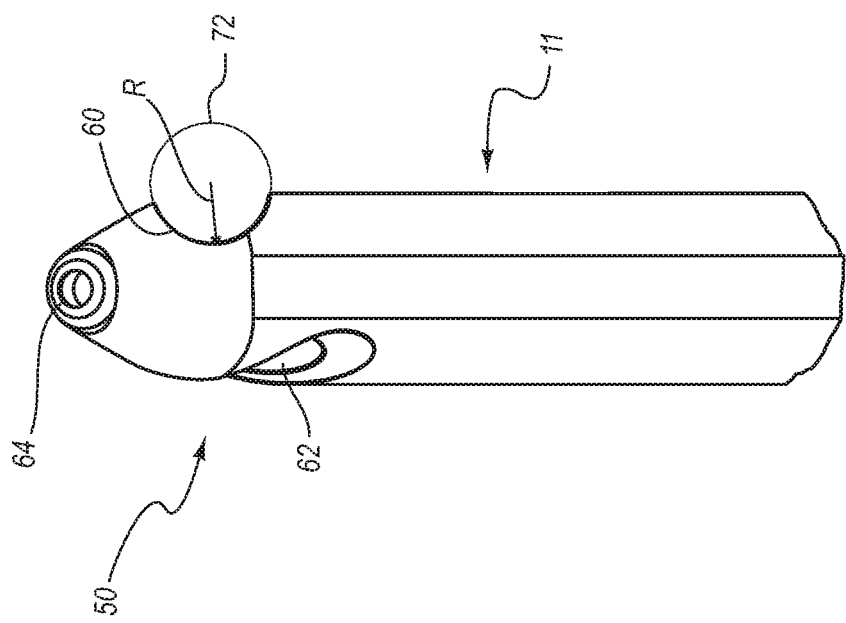
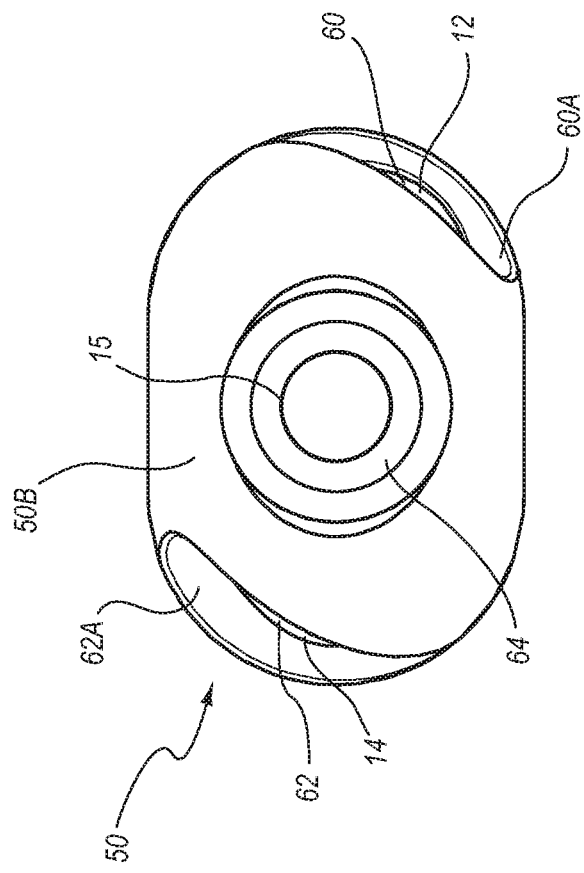

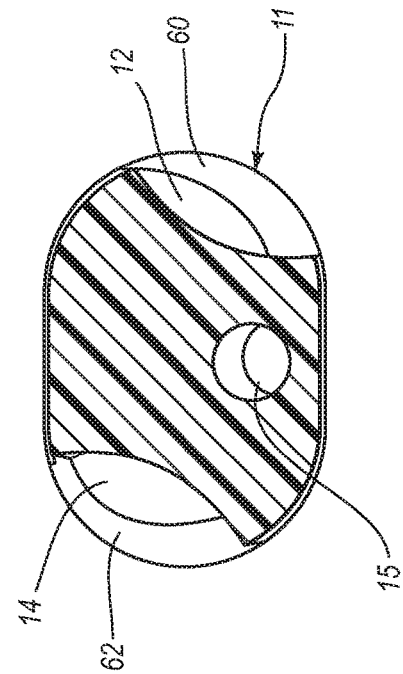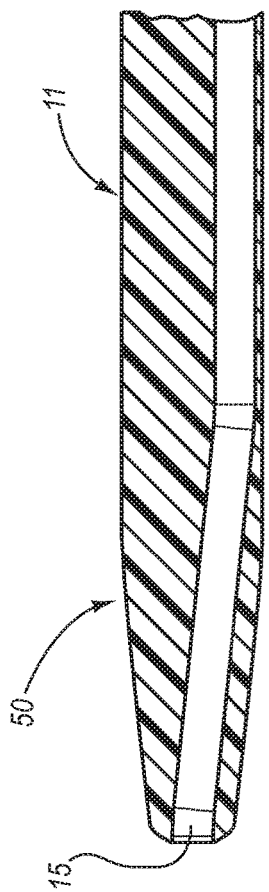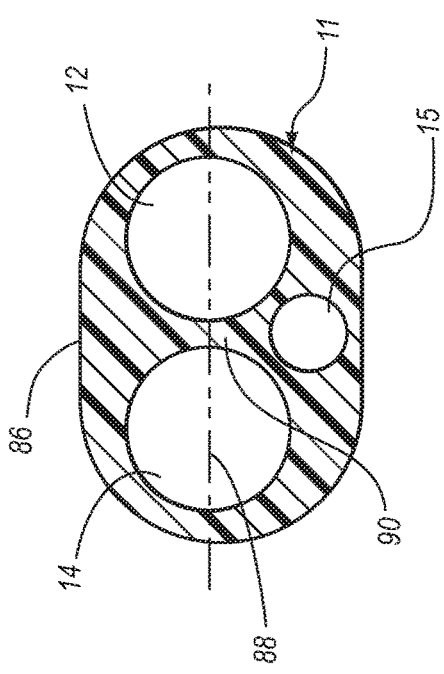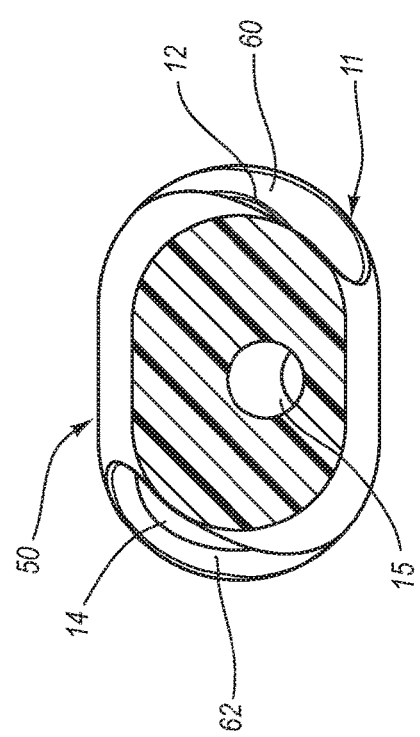
FIG. 8A
FIG. 8B
FIG. 8C
FIG. 8D

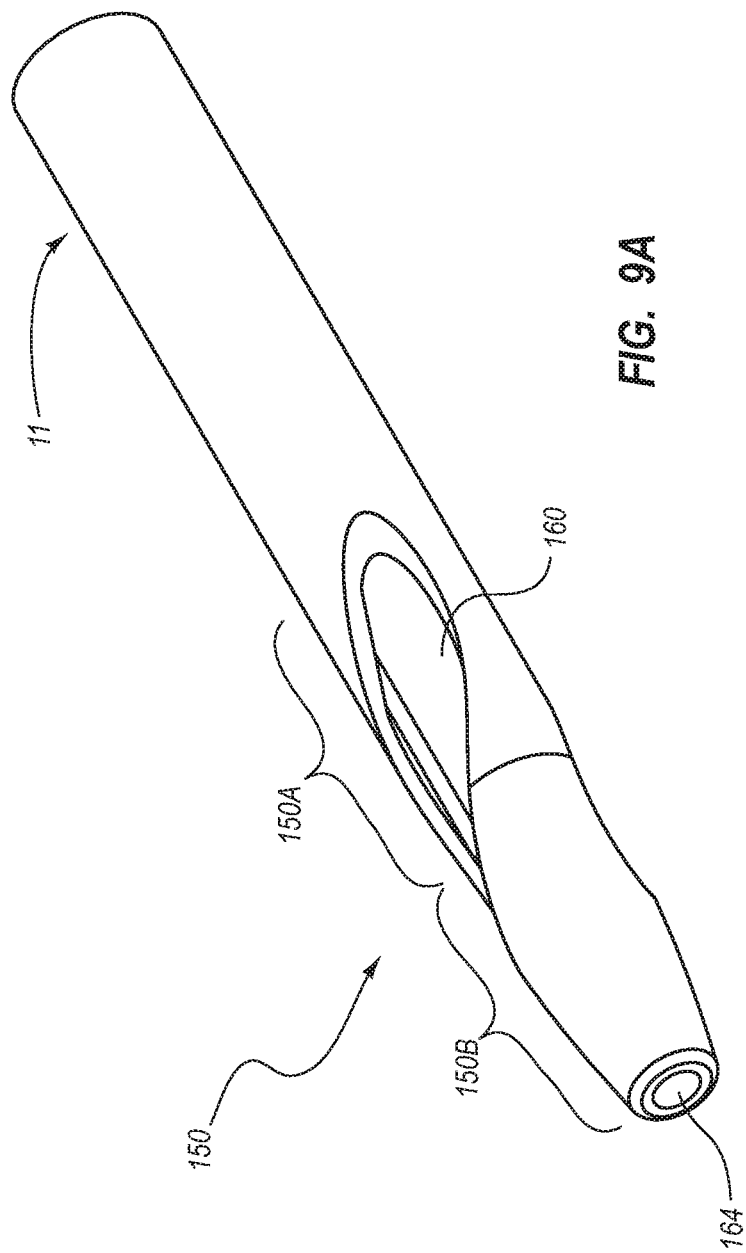

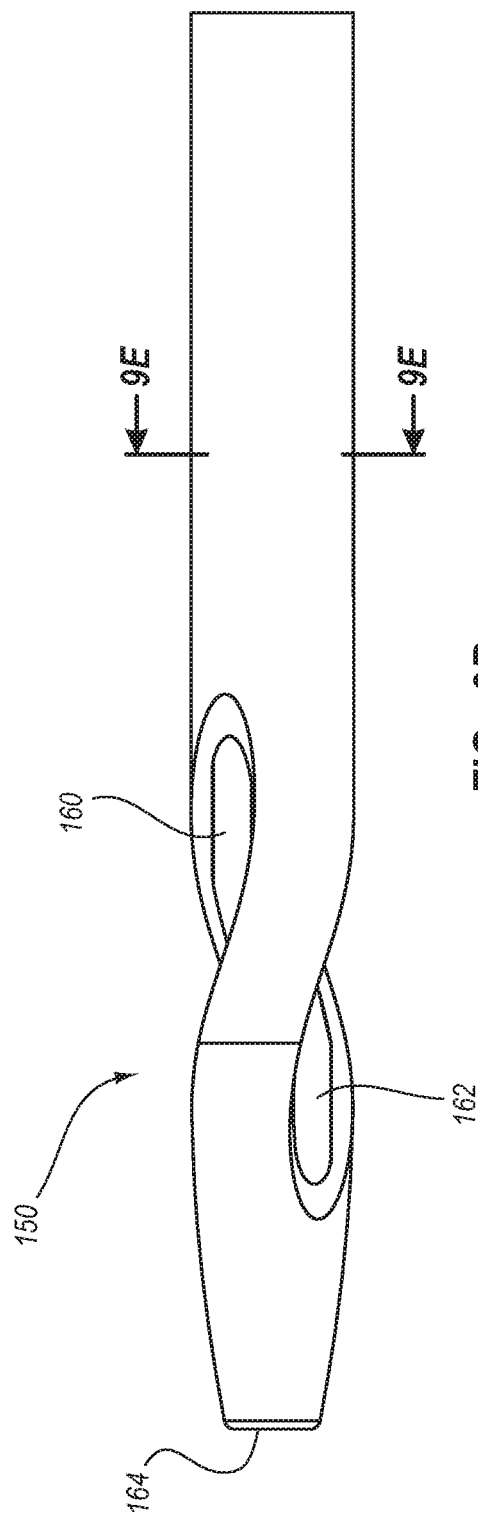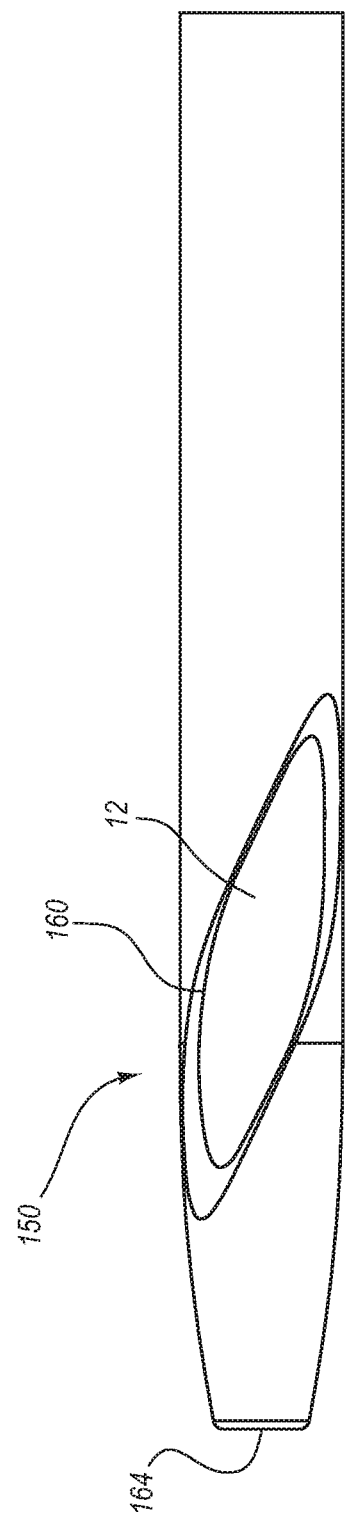

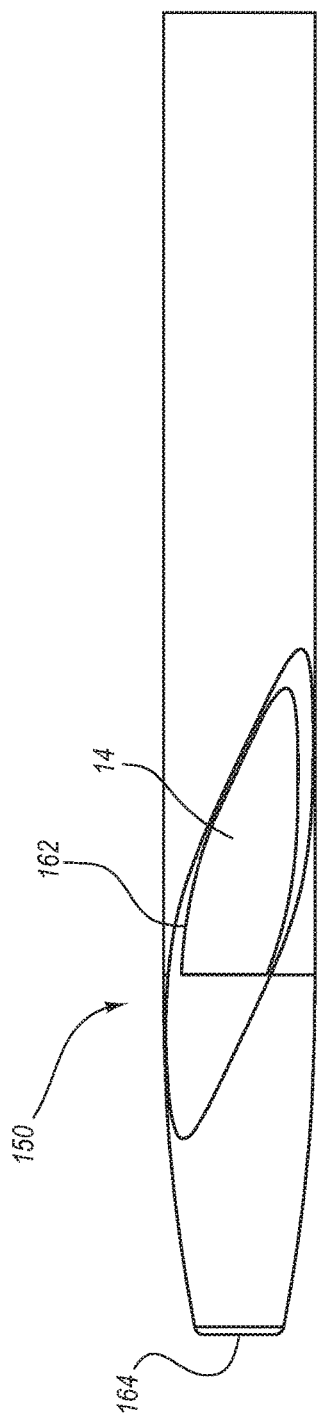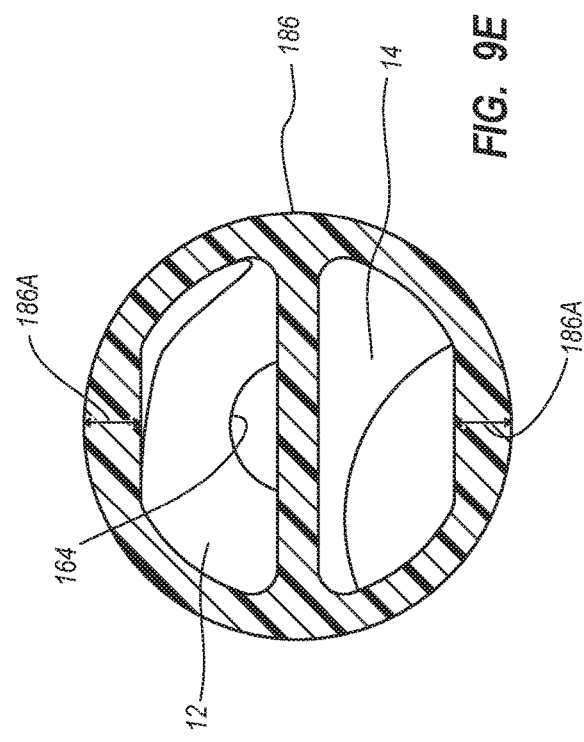

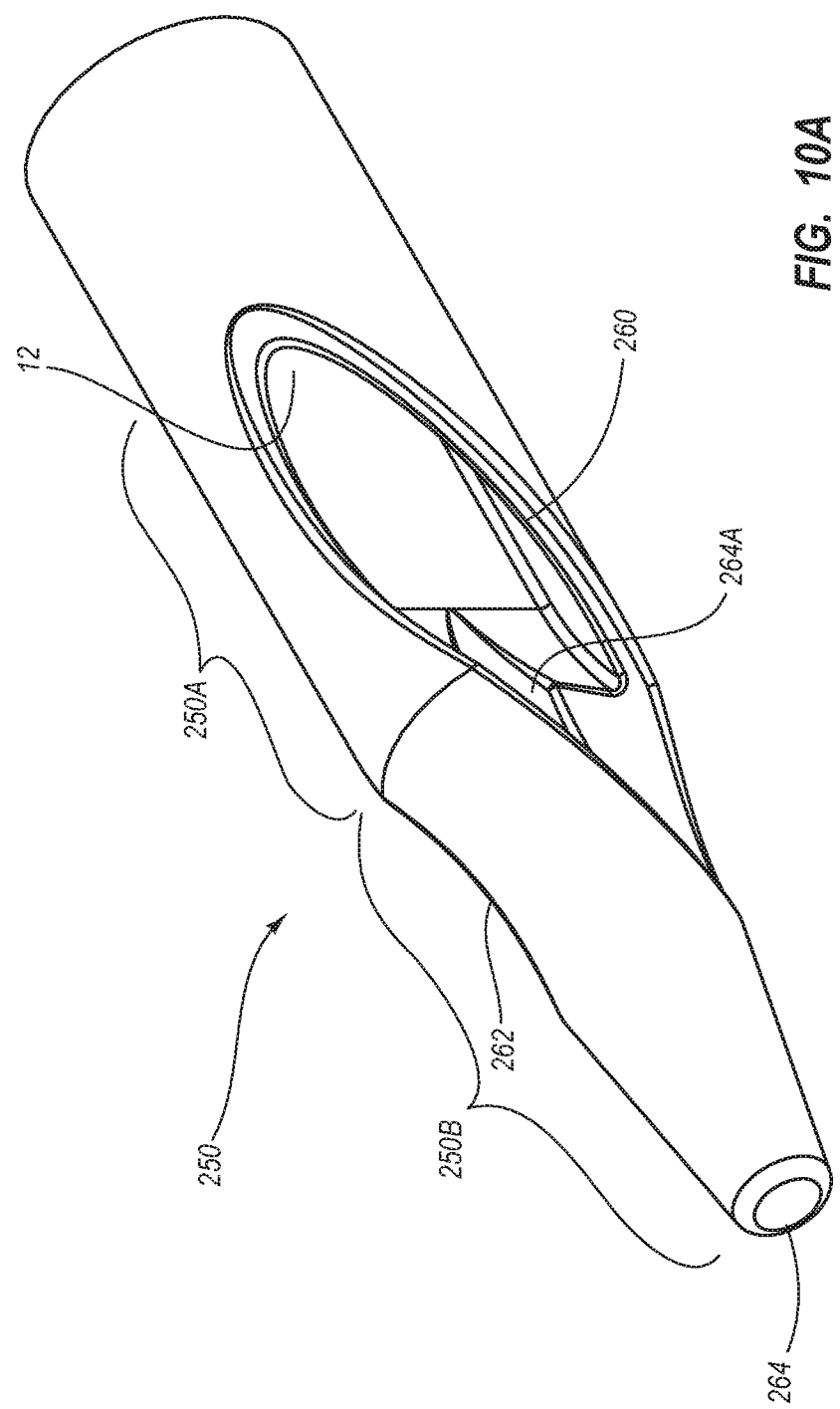

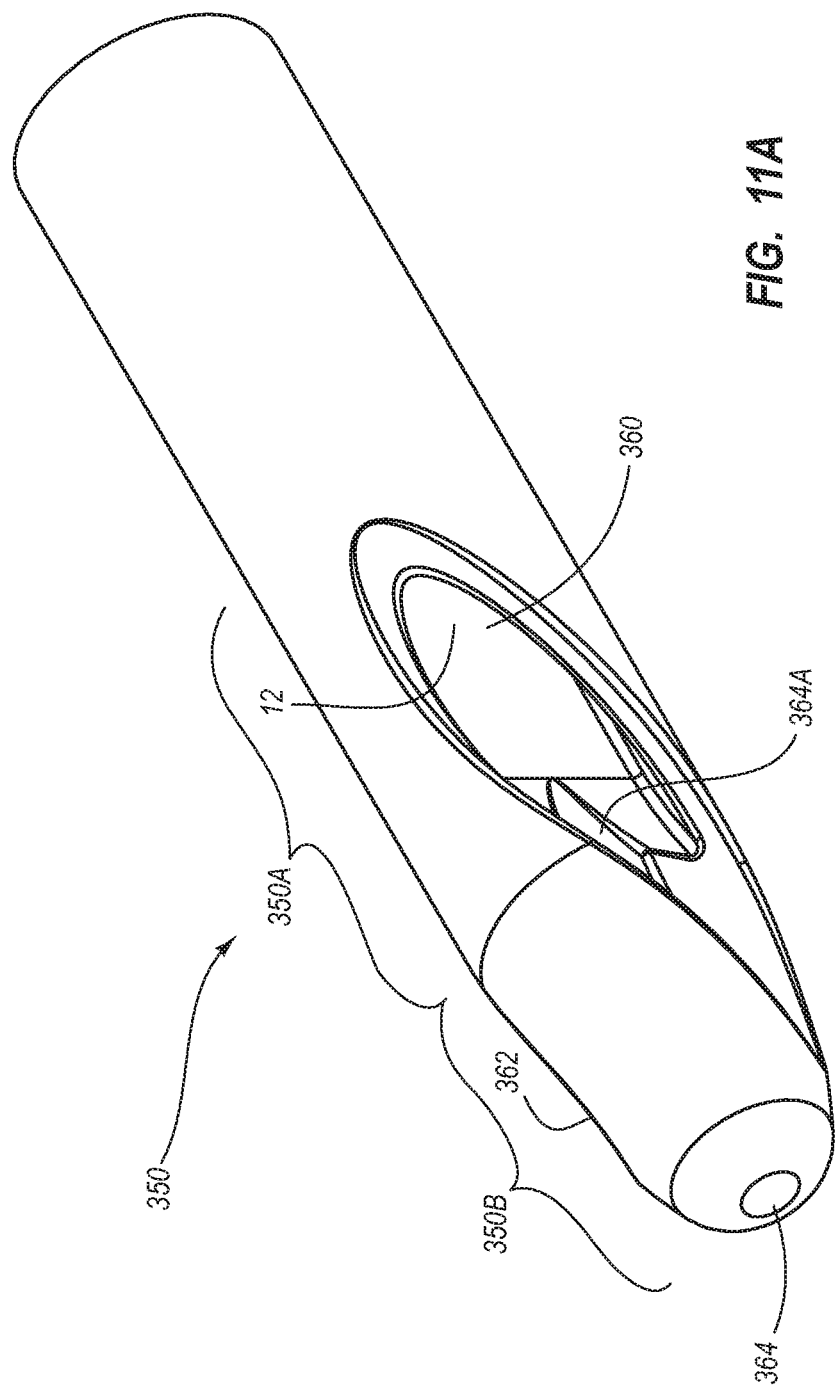

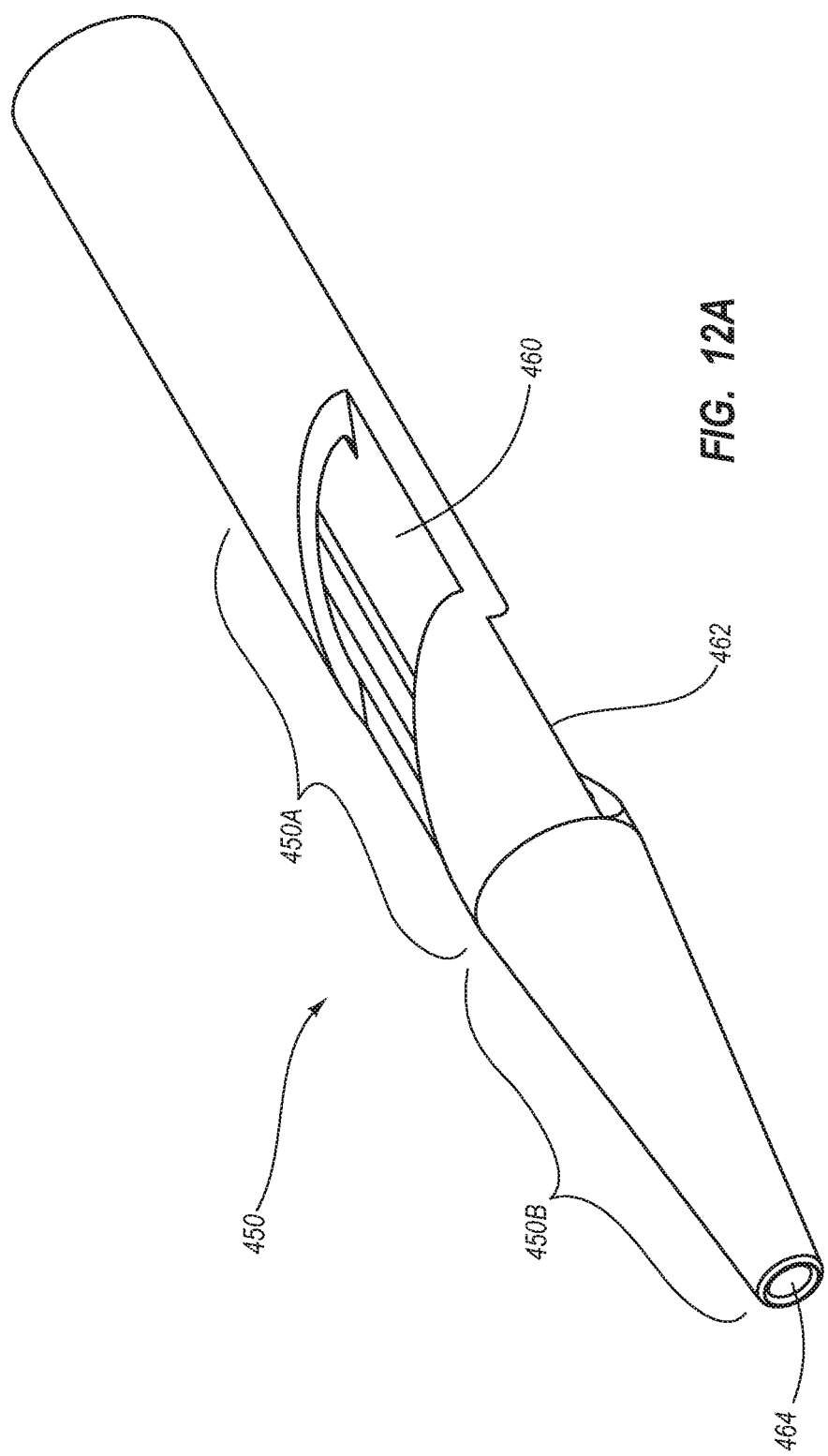

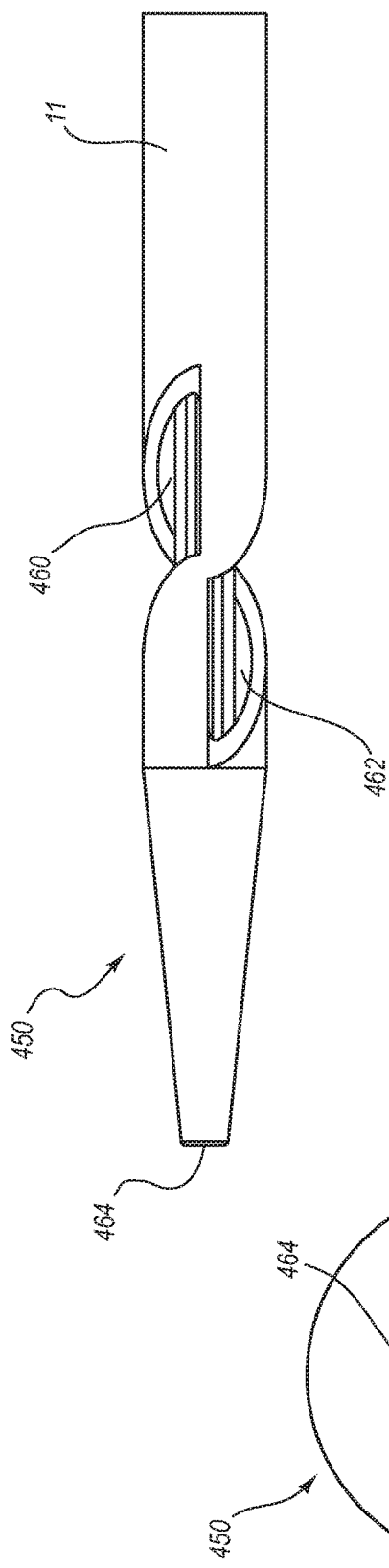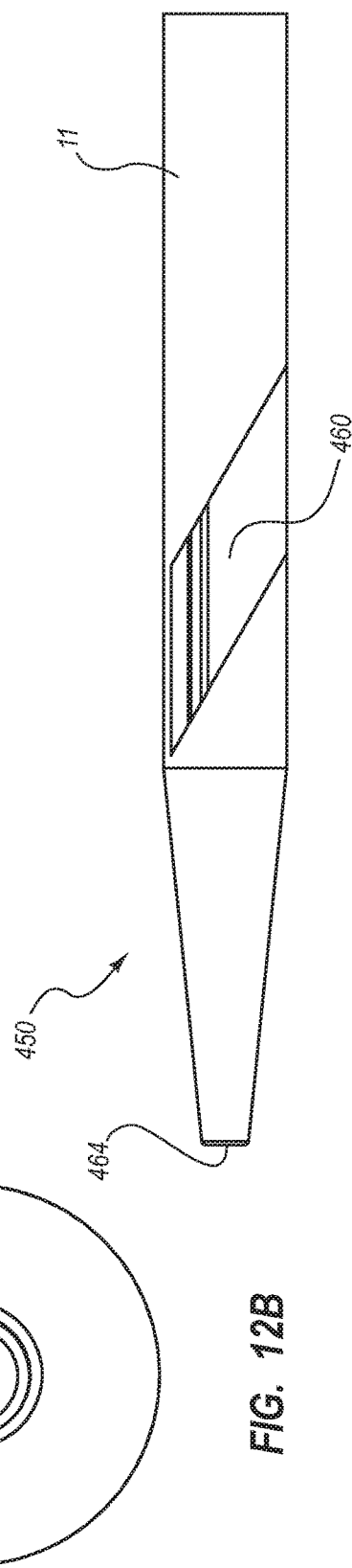

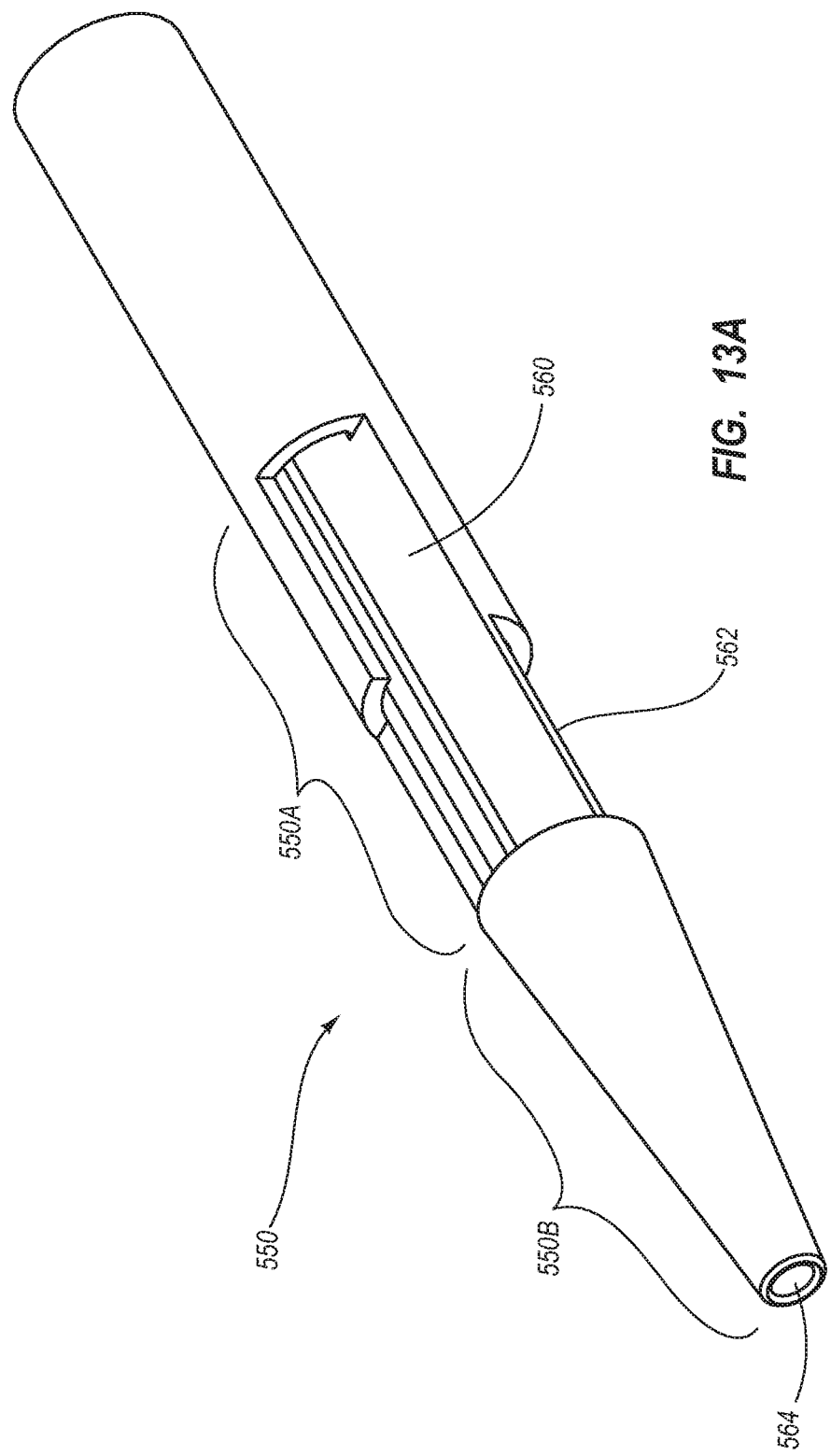

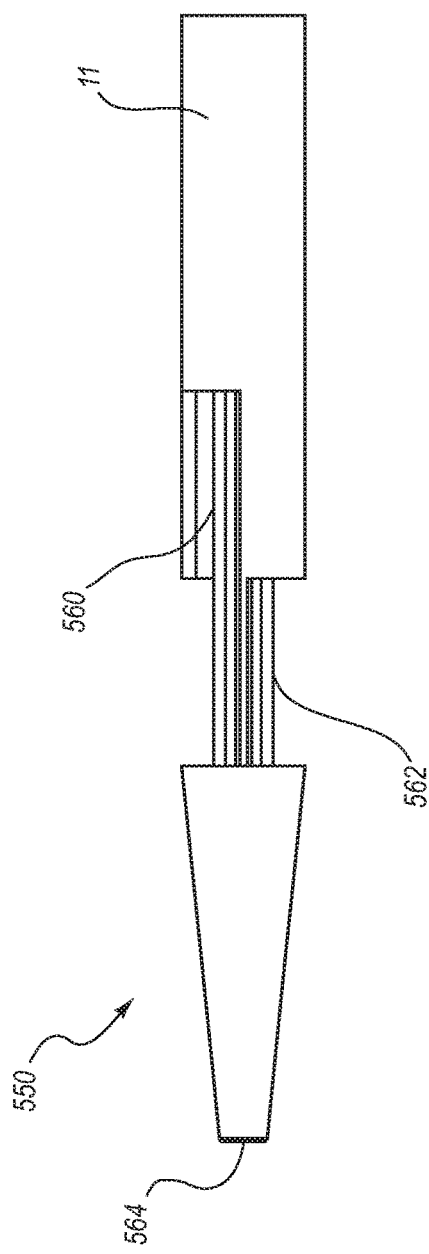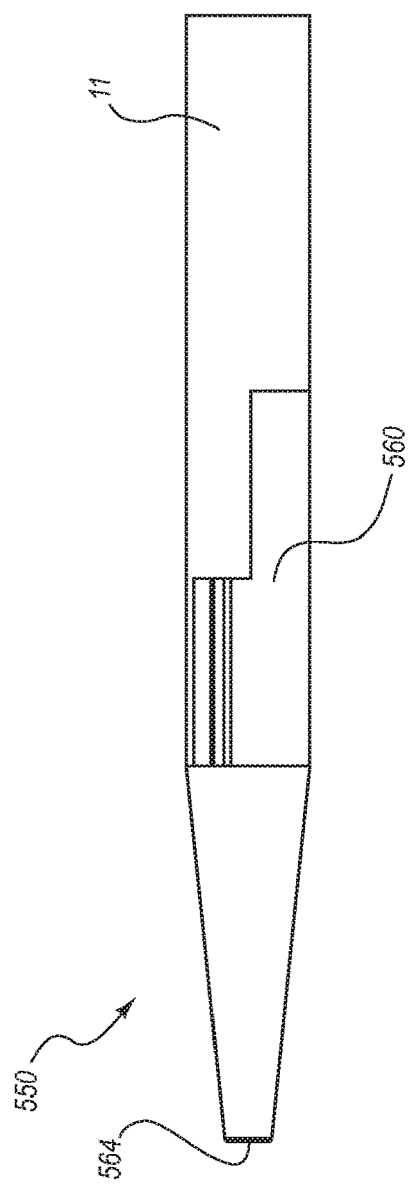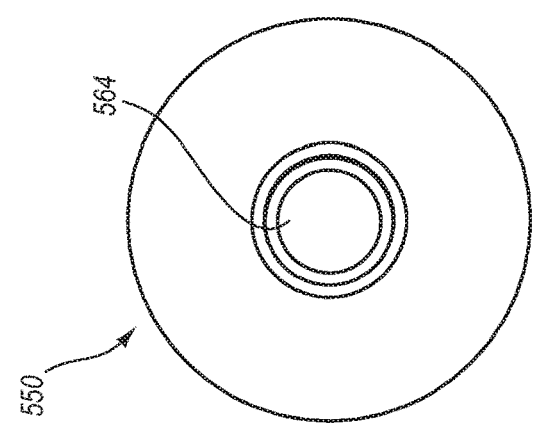

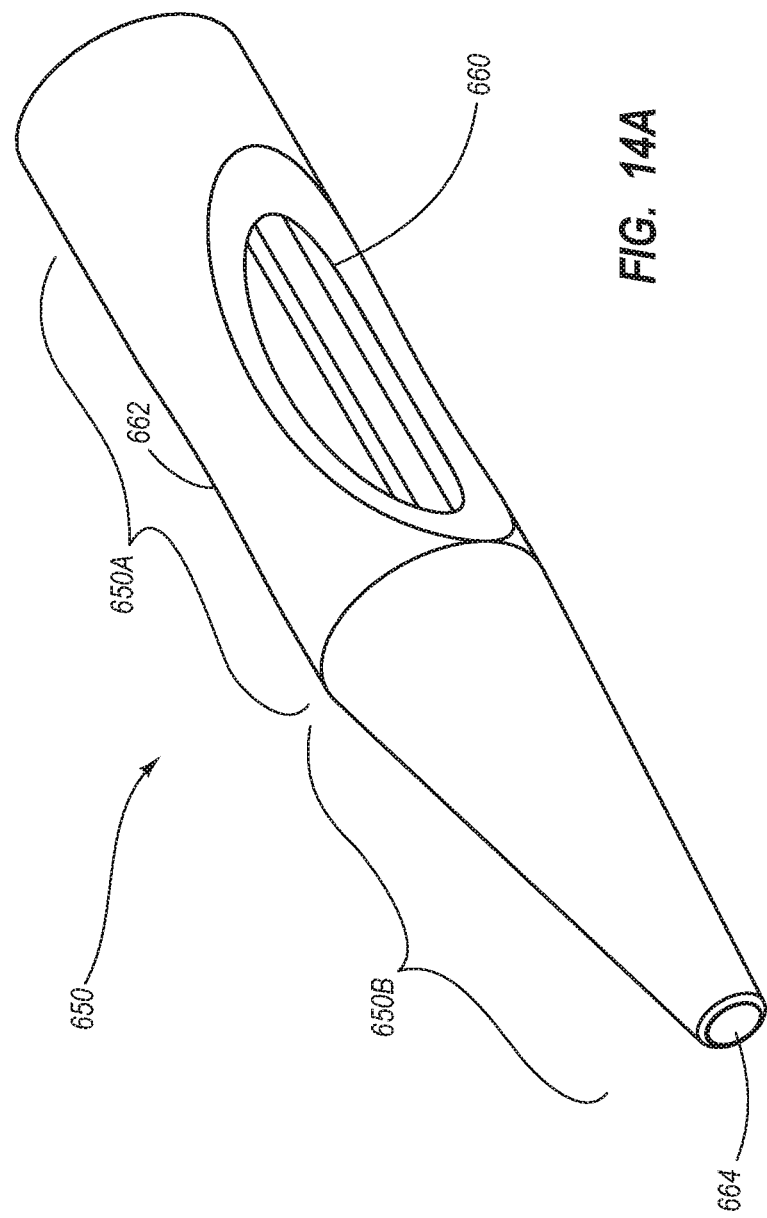

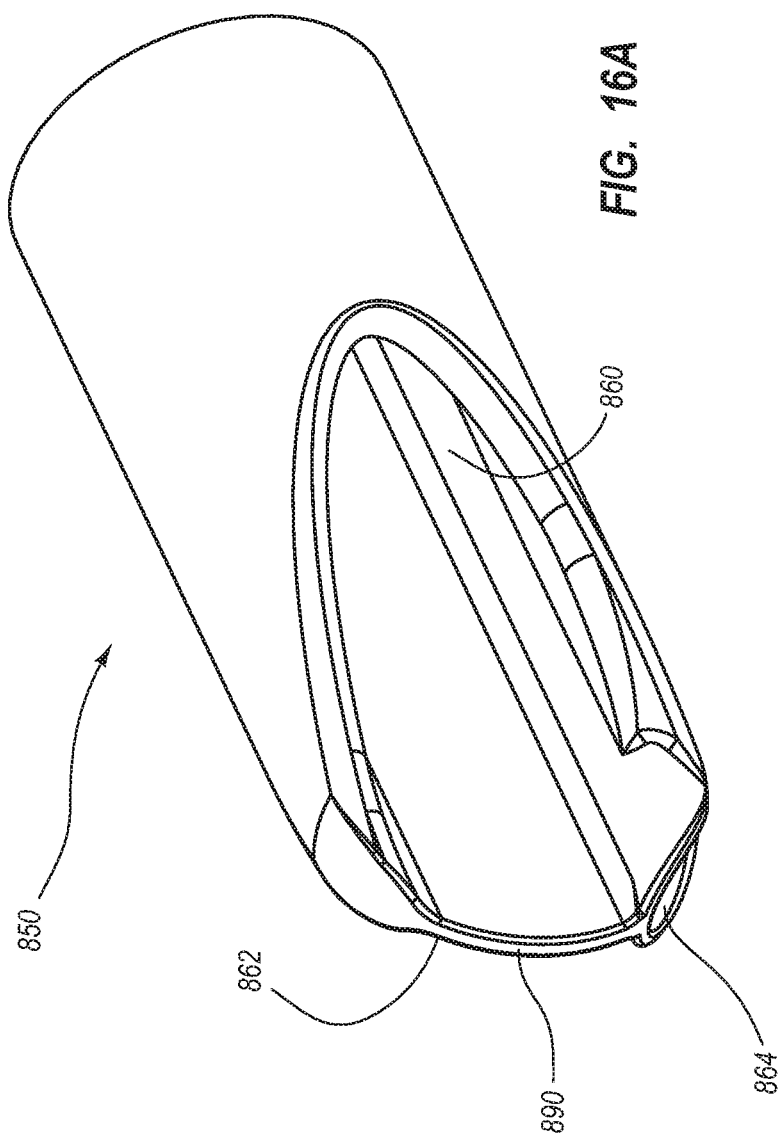

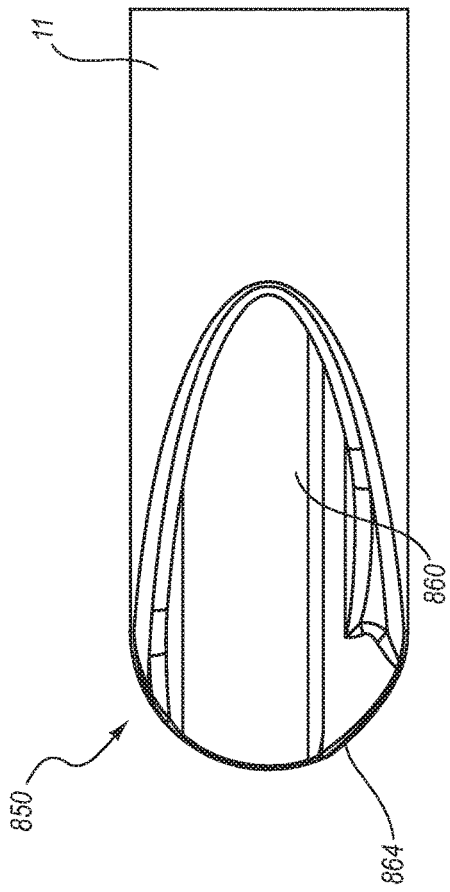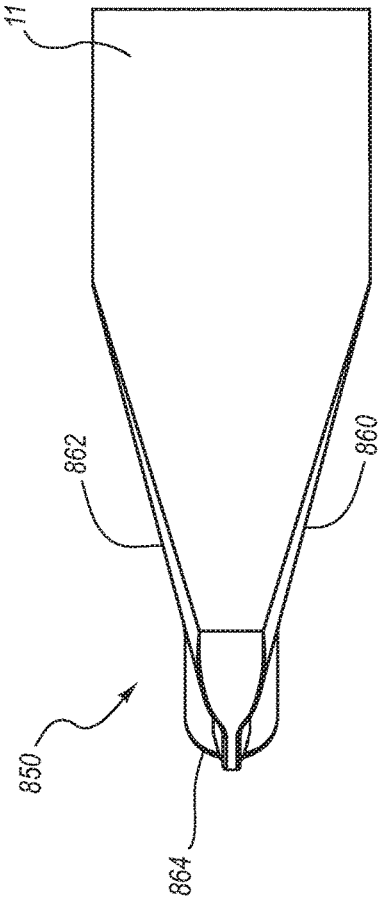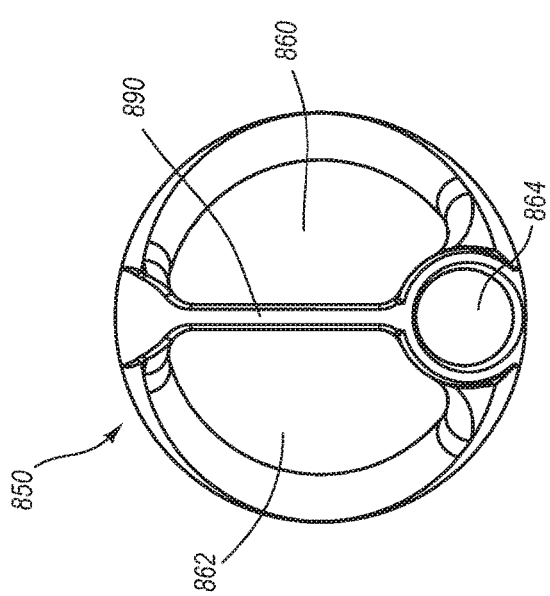

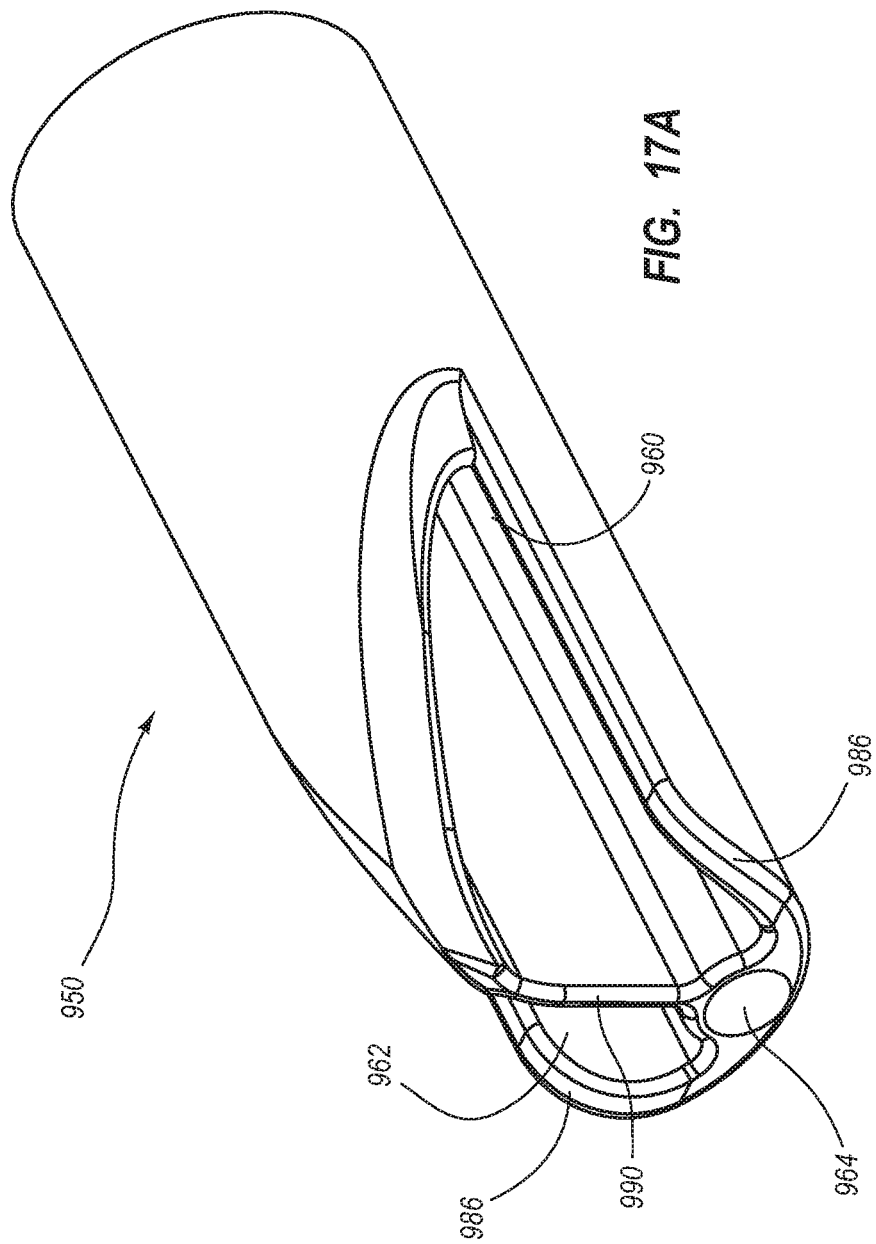

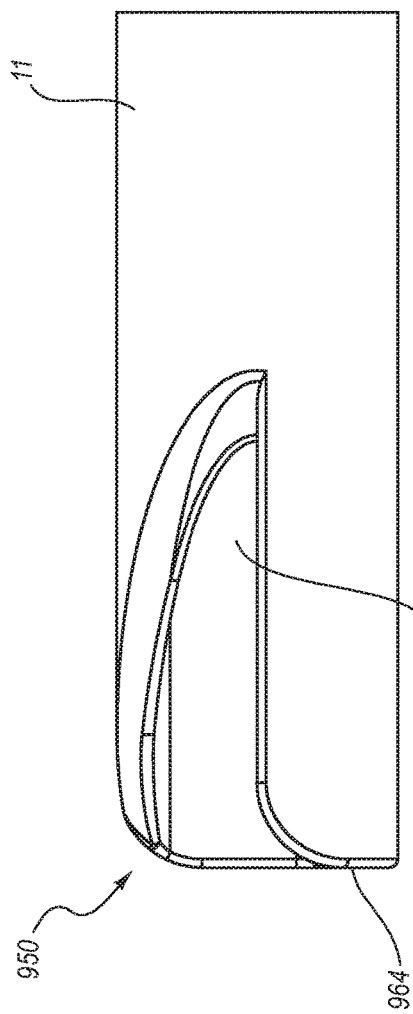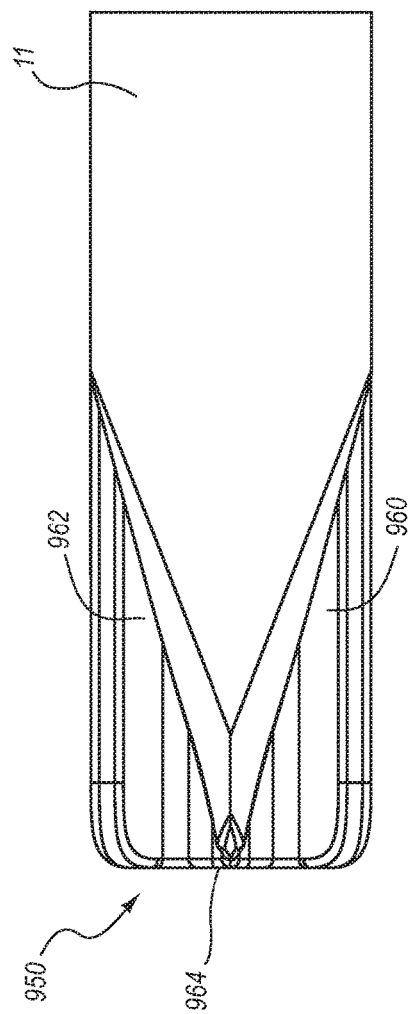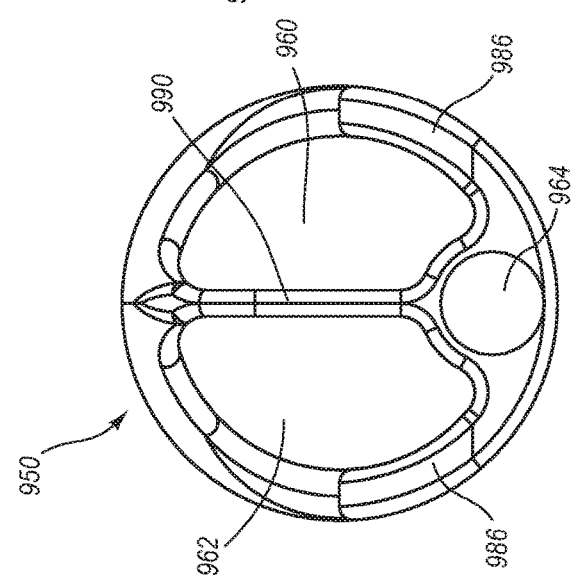

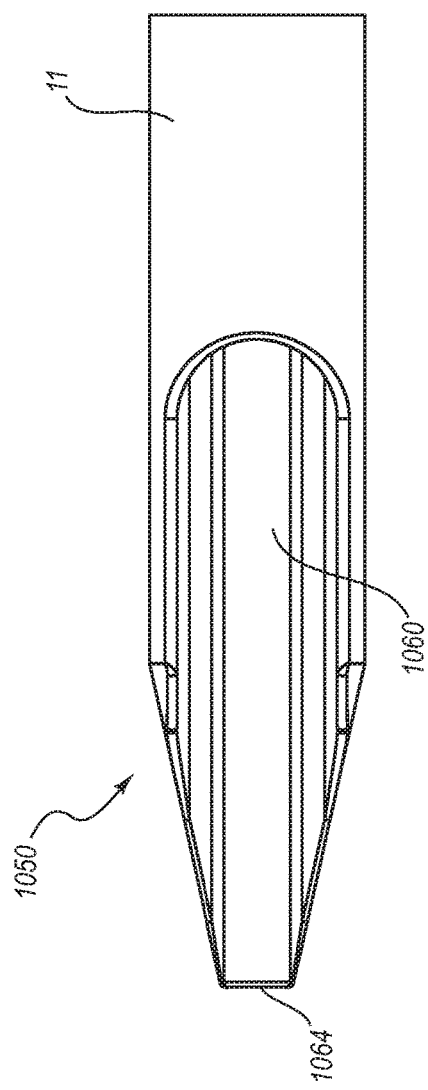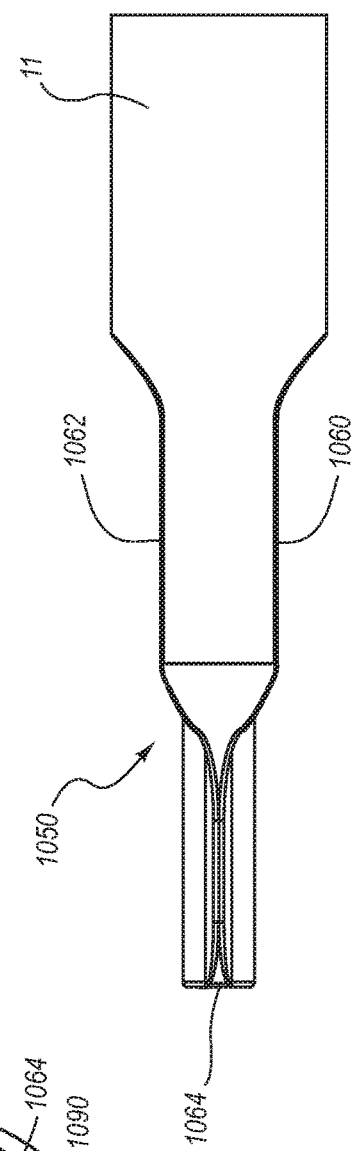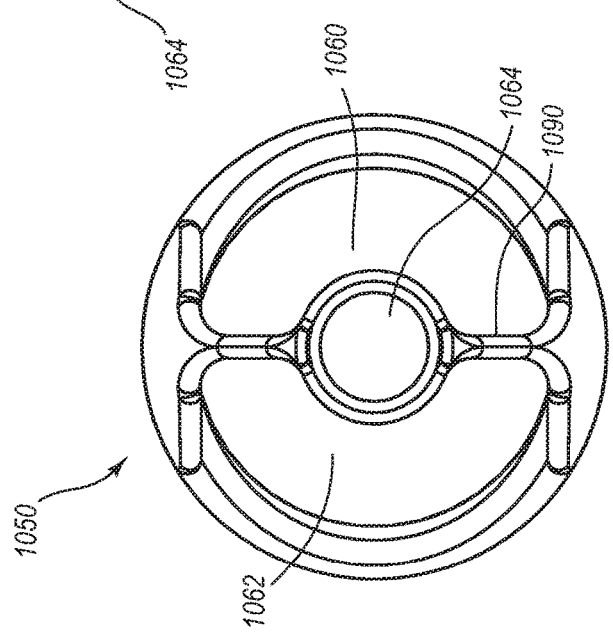

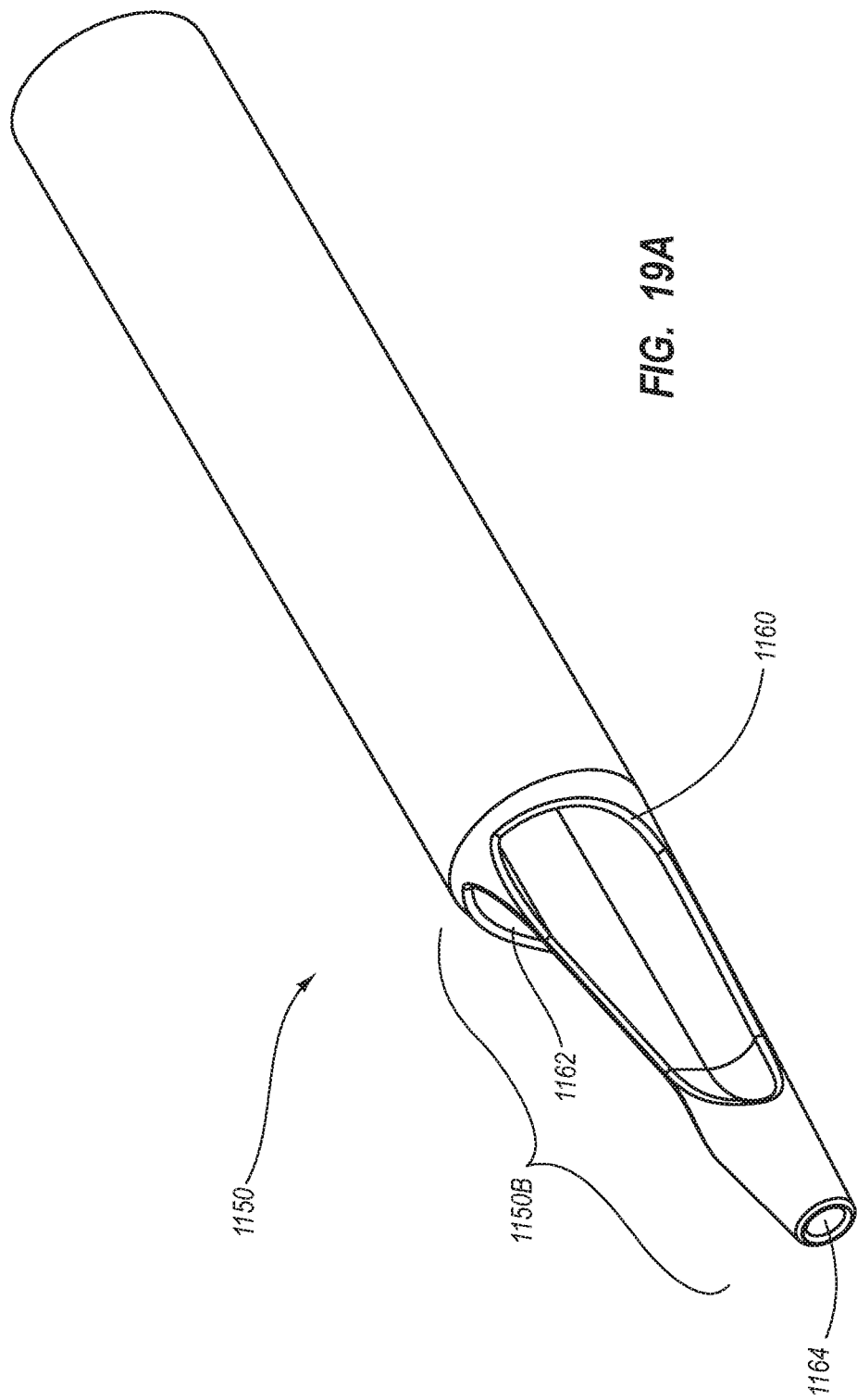

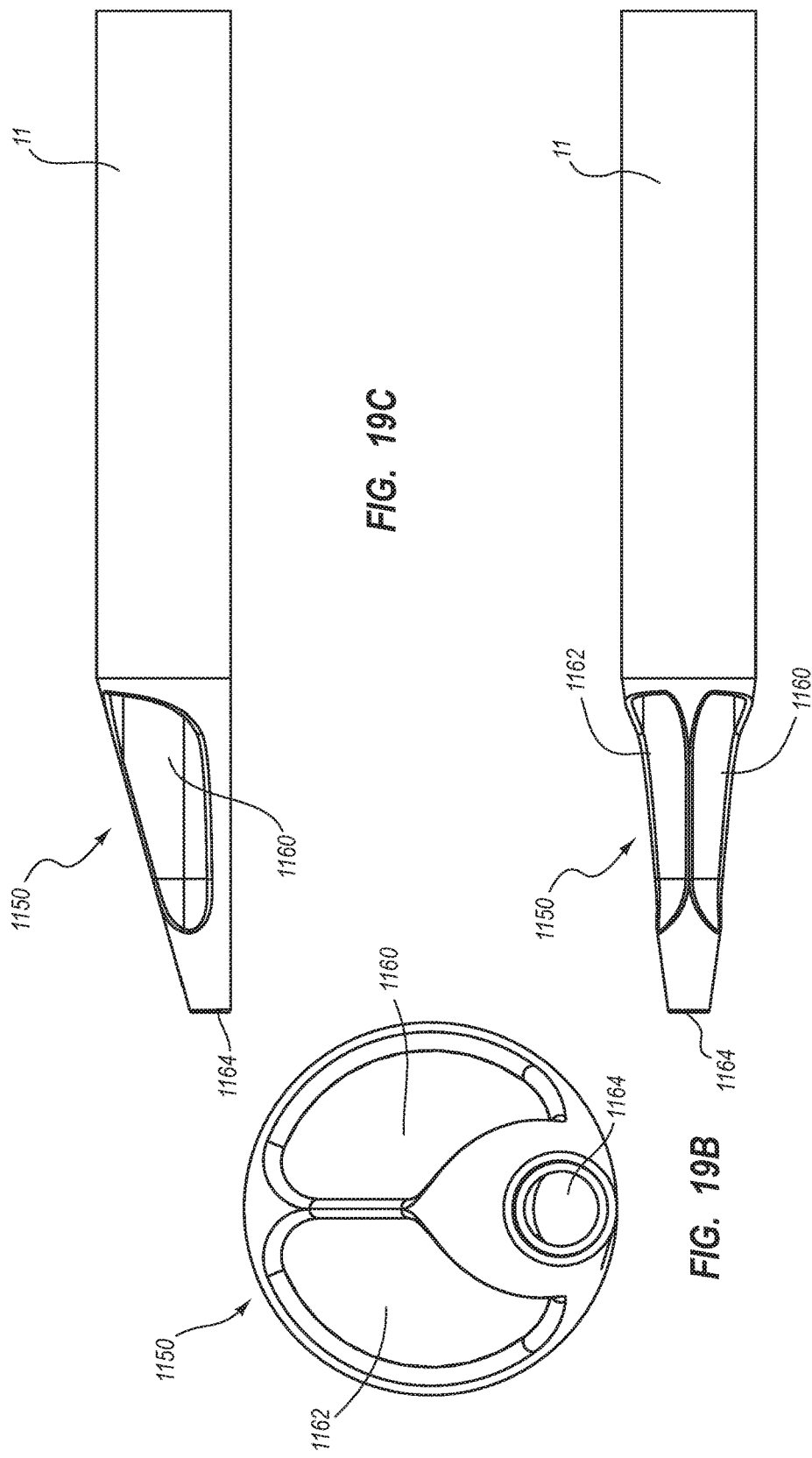

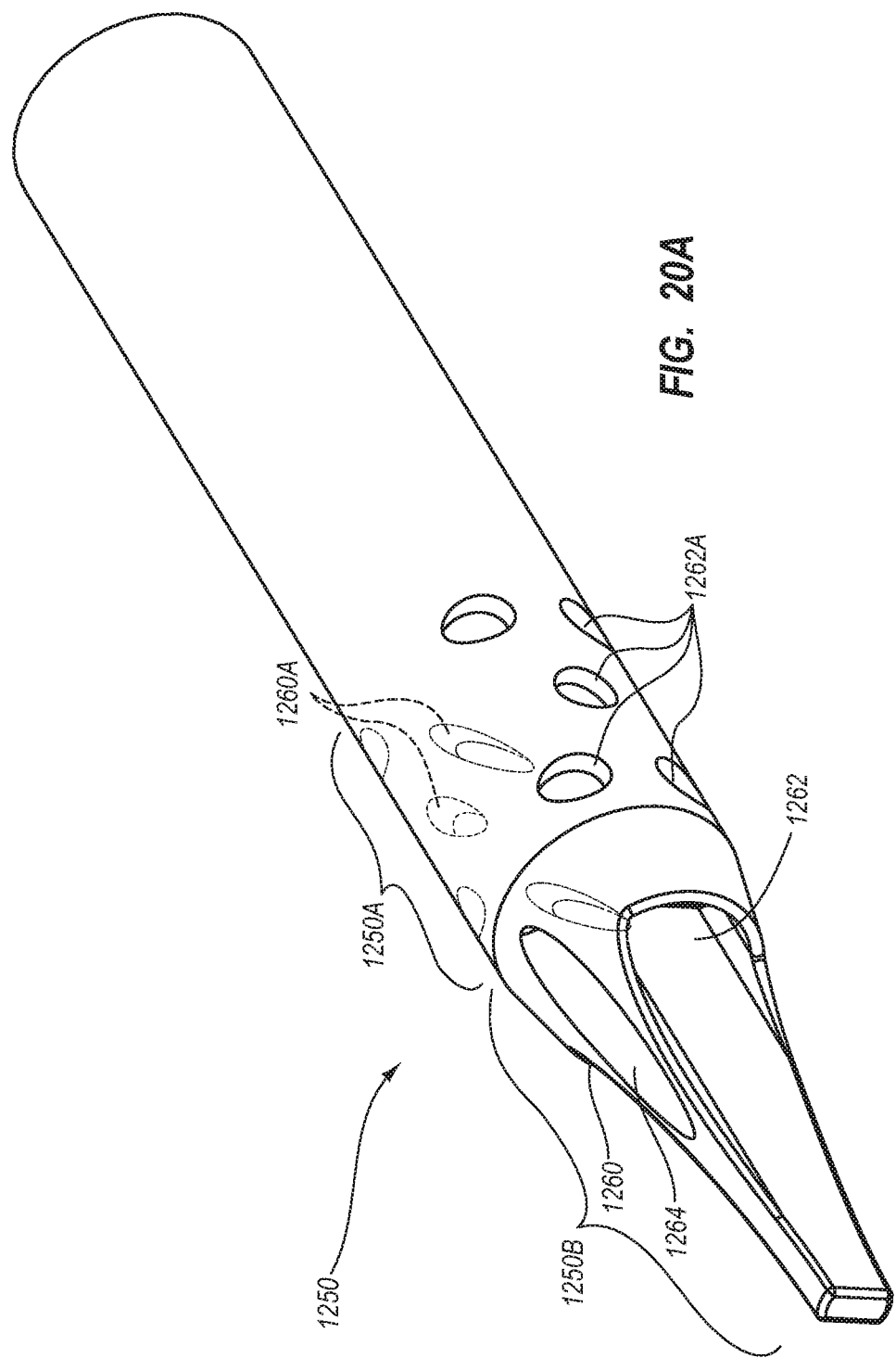

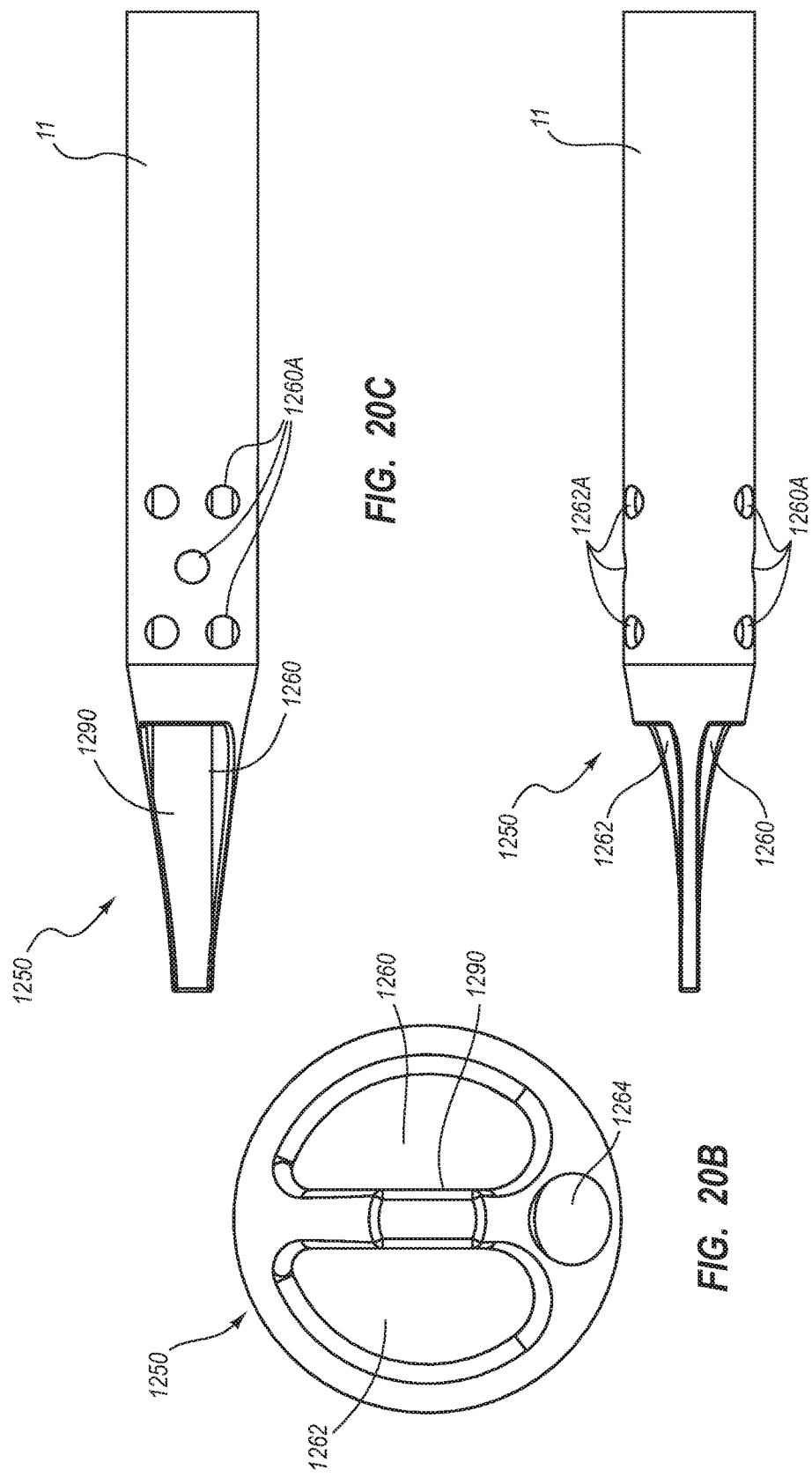

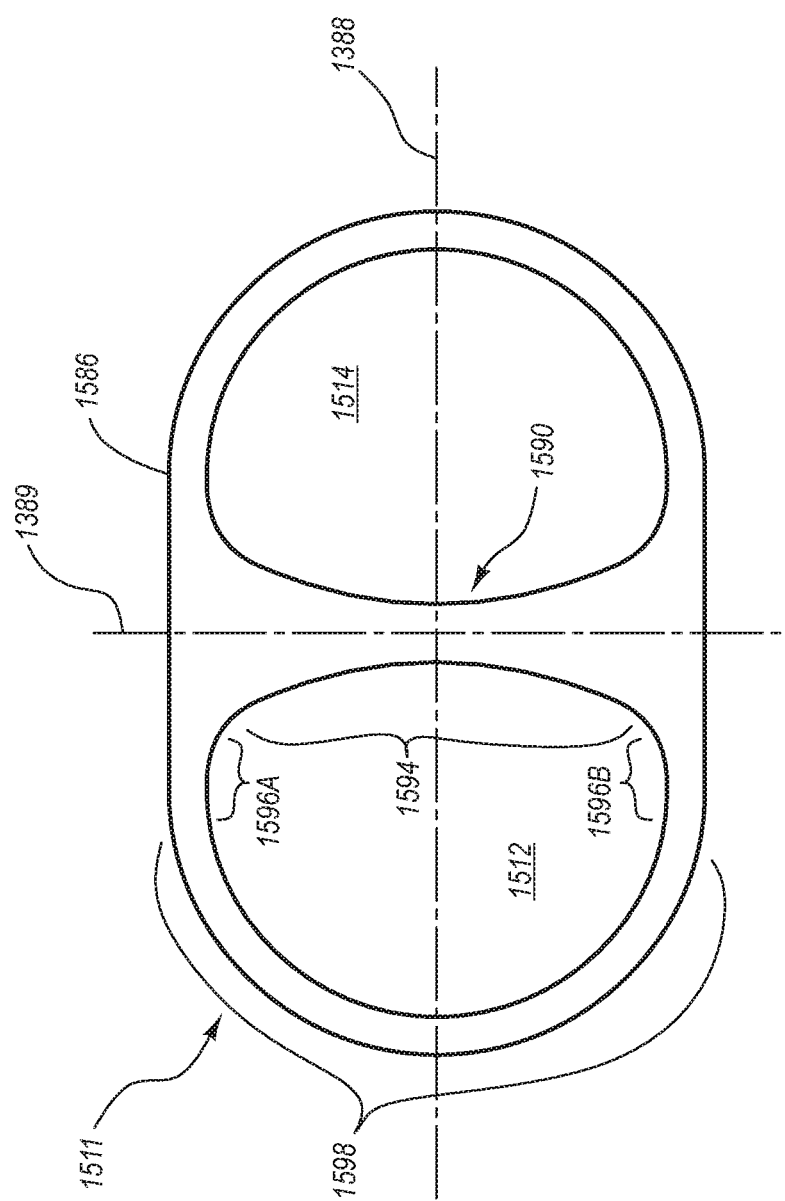

CATHETER ASSEMBLY INCLUDING A MULTI-LUMEN CONFIGURATION

CROSS-REFERENCE TO RELATED APPLICATIONS

This application is a divisional of U.S. patent application Ser. No. 14/549,941, filed Nov. 21, 2014, now U.S. Pat. No. 9,579,485, which claims the benefit of U.S. Provisional Application No. 61/907,344, filed Nov. 21, 2013, and titled "Catheter Including a Multi-Lumen Configuration," and which is a continuation-in-part of U.S. patent application Ser. No. 13/329,156, filed Dec. 16, 2011, and titled "Catheter Assembly Including Triple-Lumen Tip," now U.S. Pat. No. 8,894,601, which is a continuation of U.S. patent application Ser. No. 12/262,820, filed Oct. 31, 2008, and titled "Catheter Assembly Including Triple-Lumen Tip," now U.S. Pat. No. 8,092,415, which claims the benefit of U.S. Provisional Application No. 60/984,661, filed Nov. 1, 2007, and titled "Catheter Assembly Including Triple Lumen Tip." Each of the aforementioned applications is incorporated herein by reference in its entirety.

BRIEF SUMMARY

Briefly summarized, embodiments of the present invention are directed to a catheter assembly for use in accessing a vasculature or other vessel of a patient during renal replacement or other suitable therapies. In one embodiment, the catheter assembly includes a catheter body that defines at least first and second lumens. The catheter body defines a distal tip region that includes at least one venous lateral opening that is in fluid communication with the first lumen and includes a distal-facing portion, and at least one arterial lateral opening that is in fluid communication with the second lumen and includes a distal-facing portion. The at least one arterial lateral opening is opposingly positioned in a substantially un-staggered configuration with respect to the at least one venous lateral opening. A distal end opening is defined on the distal tip region and is sized to pass a fluid therethrough. In one embodiment, the distal end opening is in fluid communication with a third lumen of the catheter body that can withstand high fluid flow rates associated with power injection of contrast media, for instance.

In another embodiment, a catheter assembly including a catheter body defining a first lumen and a second lumen is disclosed. The catheter body includes a distal tip region, which in turn includes a nose portion that defines a distally converging outer surface. A venous lateral opening, in fluid communication with the first lumen, is partially defined on the distally converging outer diameter. An arterial lateral opening, in fluid communication with the second lumen, is also partially defined on the distally converging outer diameter. The venous and arterial lateral openings are symmetrically disposed in a substantially un-staggered position with respect to one another. The distal tip portion further includes a distal end opening in fluid communication with one of the venous and arterial lumens and is sized to pass a guidewire therethrough.

In yet another embodiment, the first and second lumens each generally include a reniform cross sectional shape, while the third lumen is substantially round, interposed between the first and second lumens, and is power injectable.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 5 is an end view of the catheter distal tip region of FIG. 2;

FIG. 6 is a perspective view of the catheter distal tip region of FIG. 2, depicting various details of lateral openings defined therein;

FIG. 8A is a cross sectional view of the catheter assembly, taken along the line 8A-8A in FIG. 4;

FIG. 8B is another cross sectional view of the catheter tip, taken along the line 8B-8B in FIG. 4;

FIG. 8C is yet another cross sectional view of the catheter tip, taken along the line 8C-8C in FIG. 4;

FIG. 8D is yet another cross sectional view of a distal tip region of the catheter assembly showing positioning of a third lumen thereof in accordance with one embodiment;

FIGS. 9A-9F depict various views of a catheter assembly including a distal tip region configured in accordance with one embodiment;

FIGS. 10A-10D are perspective, front, side, and top views, respectively, of a catheter including a distal tip region configured in accordance with one embodiment;

FIGS. 11A-11D are perspective, front, side, and top views, respectively, of a catheter including a distal tip region configured in accordance with one embodiment;

FIGS. 12A-12D are perspective, front, side, and top views, respectively, of a catheter including a distal tip region configured in accordance with one embodiment;

FIGS. 13A-13D are perspective, front, side, and top views, respectively, of a catheter including a distal tip region configured in accordance with one embodiment;

FIGS. 14A-14D are perspective, front, side, and top views, respectively, of a catheter including a distal tip region configured in accordance with one embodiment;

FIGS. 16A-16D are perspective, front, side, and top views, respectively, of a catheter including a distal tip region configured in accordance with one embodiment;

FIGS. 17A-17D are perspective, front, side, and top views, respectively, of a catheter including a distal tip region configured in accordance with one embodiment;

FIGS. 18A-18D are perspective, front, side, and top views, respectively, of a catheter including a distal tip region configured in accordance with one embodiment;

FIGS. 19A-19D are perspective, front, side, and top views, respectively, of a catheter including a distal tip region configured in accordance with one embodiment;

FIGS. 20A-20D are perspective, front, side, and top views, respectively, of a catheter including a distal tip region configured in accordance with one embodiment;

FIG. 28 is a cross-sectional view of the catheter assembly of FIG. 27.

DETAILED DESCRIPTION OF SELECTED EMBODIMENTS

Figure 1:
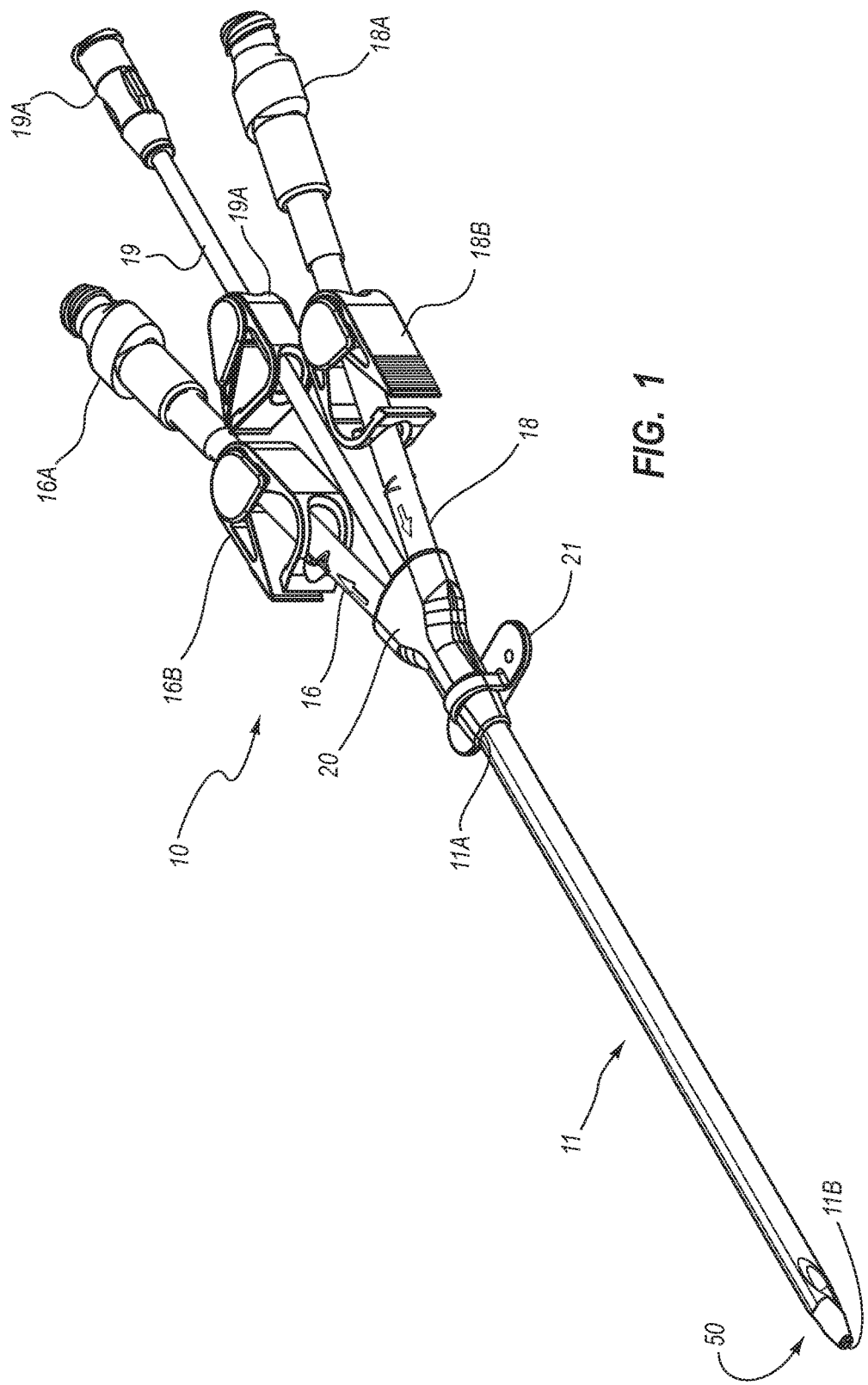
FIG. 1 is a perspective view of a catheter assembly incorporating various features of an embodiment of the present invention.
Figure 1A:
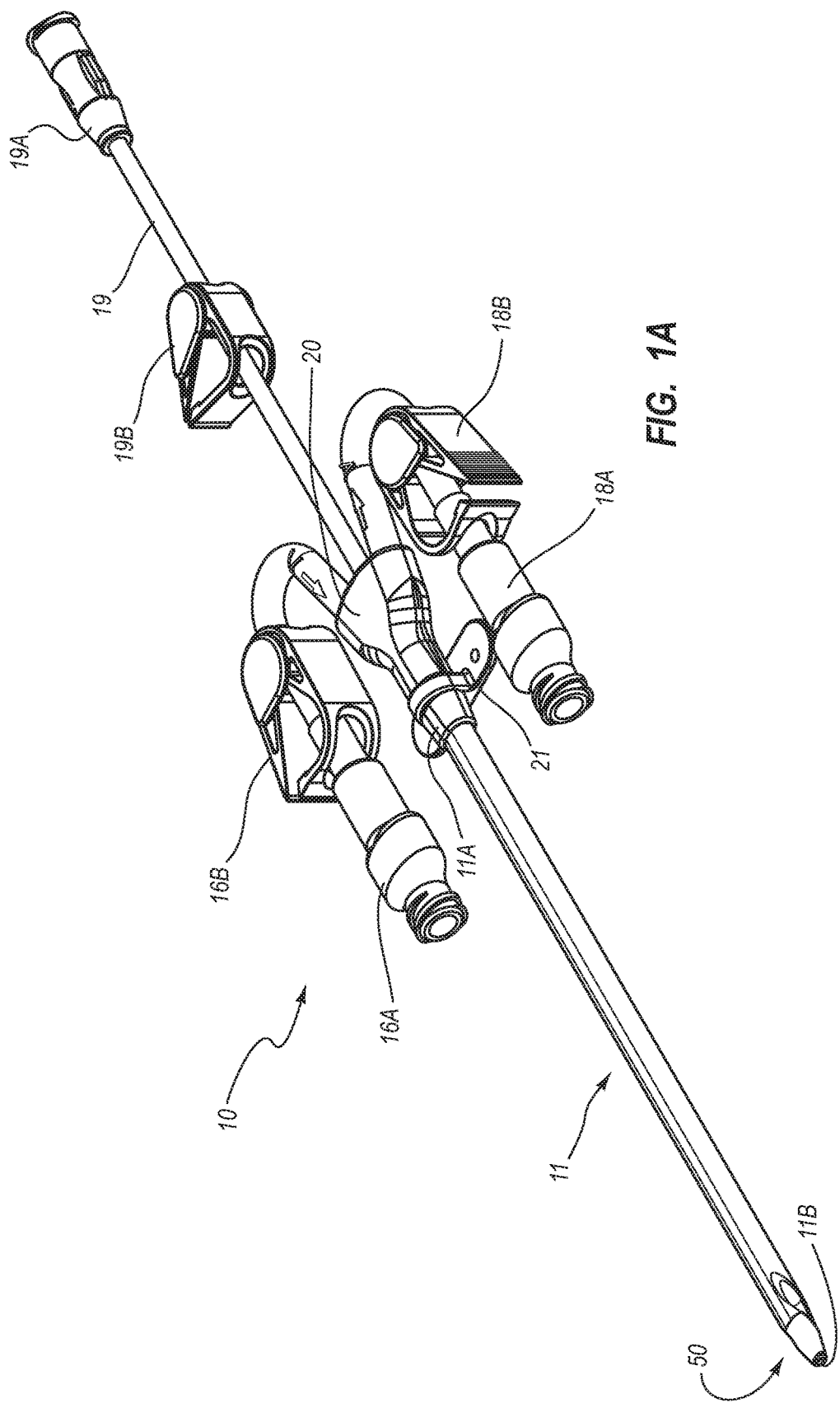
FIG. 1A is a perspective view of another example of a catheter assembly configured according to one embodiment.

Reference will now be made to figures wherein like structures will be provided with like reference designations. It is understood that the drawings are diagrammatic and schematic representations of example embodiments, and are not limiting of the embodiments nor are they necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

FIGS. 1-20D depict various features of embodiments of the present invention, which are generally directed to an acute catheter assembly for use in accessing a vasculature or other vessel of a patient during renal replacement therapies such as hemodialysis or blood purification, though the principles of the present invention may be extended to other catheters employed in other uses in addition to these. Such acute catheters are typically employed in short-term placement scenarios such as a placement of less than 30 days, though the principles to be described herein can also apply to mid-term and long term catheter placements as well.

In accordance with one example embodiment, the catheter assembly includes a distal tip region defining separate venous and arterial lateral openings, in fluid communication with corresponding venous and arterial lumens that are employed for simultaneously infusing and aspirating blood from a vein or other vessel of a patient's vasculature during hemodialysis treatments. The venous and arterial lateral openings are disposed in a substantially equivalent, non-staggered position with respect to one another so as to enable positioning thereof in a predetermined region of the vasculature. This notwithstanding, the lateral openings are configured to reduce the likelihood of recirculation by the arterial segment of treated blood just returned to the vessel by the venous segment, thus increasing catheter efficiency. Moreover, the lateral openings can be operated in a reverse flow configuration without significantly impacting catheter efficiency during hemodialysis.

Embodiments of the catheter assembly to be described herein further include a distal end opening in fluid communication with a lumen of the catheter configured to withstand relatively high pressure and flow rates typically associated with power injection. This enables aspiration or infusion of fluids to occur via this lumen independently of the venous and arterial lumens. "Power injection" is defined herein to include fluid infusion under relatively high flow rates and/or relatively high pressures. For instance, in one embodiment power injection includes fluid infusion through a catheter lumen at a flow rate of between about three and about eight milliliters per second, and/or at a pressure of between about 50 and about 250 psi.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Further, the words "including," "has," and "having," as used herein, including the claims, shall have the same meaning as the word "comprising."

Reference is first made to FIG. 1, which depicts various features of a hemodialysis catheter assembly, generally designated at 10, according to one example embodiment. As shown, the catheter 10 includes an elongate catheter body 11 including a proximal end 11A and a distal end 11B. The elongate catheter body 11 defines a first lumen 12, a second lumen 14, and a third lumen 15 (FIG. 7A) that longitudinally extend from the proximal end 11A to the distal end 11B thereof. The lumens 12, 14, and 15 can have one or more cross sectional shapes along their respective lengths, including round, oval, D-cross sectional shapes, or any combination thereof. In one embodiment, the first and second lumens 12, 14 are sized so as to accommodate fluid flow rates required for hemodialysis, i.e., about 300 milliliters/min. at about 250 millimeters Hg pressure. In one embodiment, the third lumen is sized with a diameter of about 0.035 to about 0.038 inch to accommodate blood draws and fluid aspiration/infusion therethrough.

A trifurcating hub 20 is included at the catheter body proximal end 11A, providing fluid communication between the first, second, and third lumens 12, 14, 15 and arterial extension leg 16, venous extension leg 18, and power extension leg 19, respectively. The extension legs 16, 18, 19 each include a luer connector 16A, 18A, 19A, and a clamp 16B, 18B, 19B. So configured, the extension legs 16, 18 provide fluid communication with the first and second lumens 12 and 14 so as to enable the infusion or aspiration of fluids from the central venous system of a patient. As such, fluid infusion or aspiration devices, such as a hemodialysis apparatus for example, may be connected to the catheter assembly 10 via the luer connectors 16A, 18A, thus providing intravascular access to the patient. Similarly, the extension leg 19 provides fluid communication with the third lumen 15 to enable fluid infusion/aspiration from the vein when a corresponding device is connected thereto via the connector 19A. Note that the respective positions and configurations of the extension legs detailed here can change according to a particular catheter assembly design and therefore not be viewed as limiting. The catheter body 11 further includes a suture wing 21 for providing securement of the catheter body to the patient.

Figure 2:
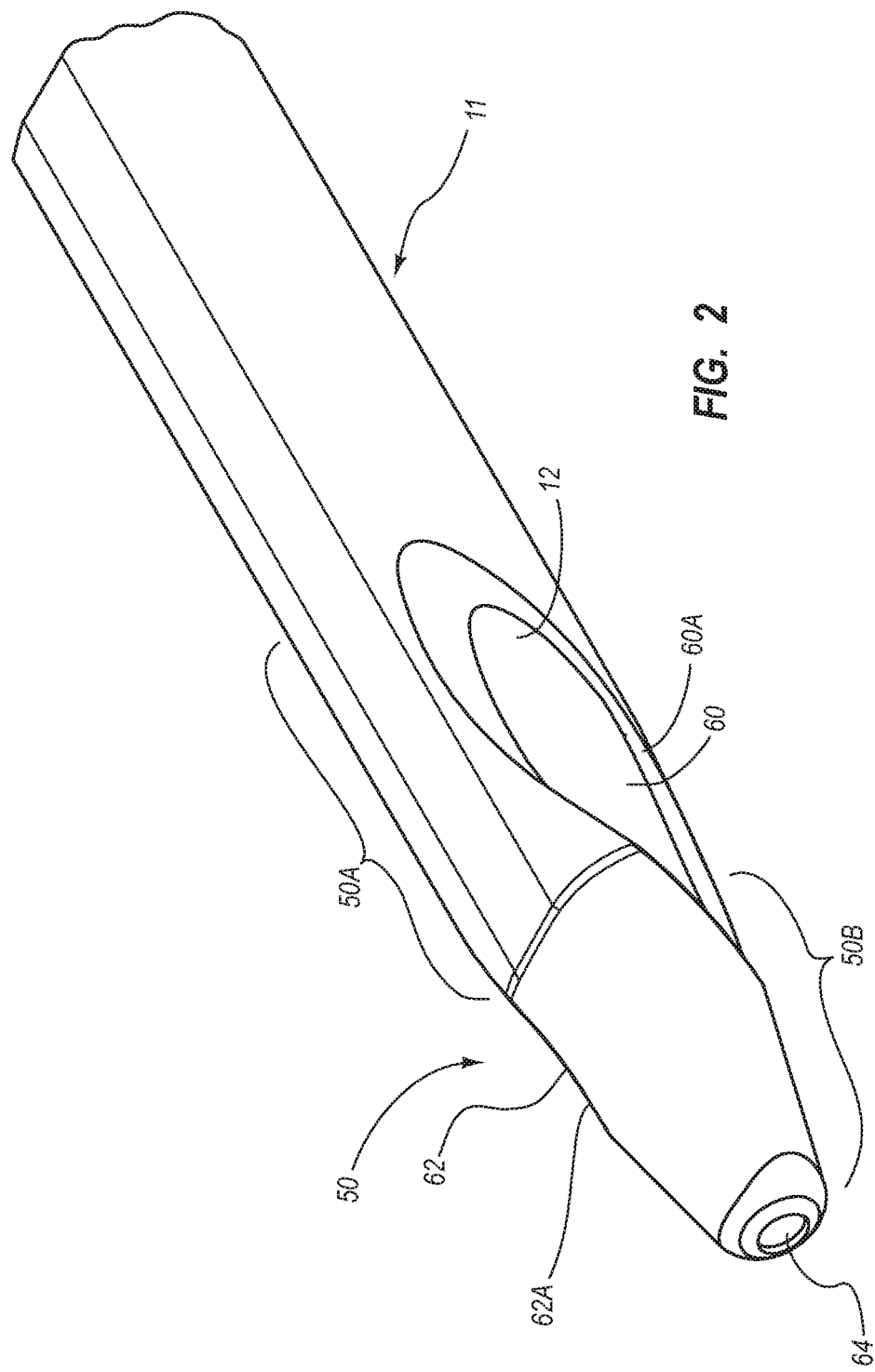
FIG. 2 is a perspective view of a distal tip region of the catheter assembly shown in FIG. 1, configured according to one embodiment.

FIG. 2 shows the catheter assembly 10 according to another example embodiment, wherein the extension legs 16, 18 each include a pre-curved portion 16C, 18C. The pre-curved portions 16C, 18C enable the extension legs 16, 18 of the catheter assembly 10 to extend downward against the patient's body once the distal portion of the catheter assembly has been placed in the vasculature to provide patient comfort.

In greater detail, the power extension leg 19 of FIGS. 1 and 2 fluidly connects to the third lumen 15 via the trifurcating hub 20. In particular, the power extension leg 19 is configured in one embodiment to enable rapid infusion, i.e., power injection, of contrast media, useful for contrast-enhanced CT scan imaging, or other fluids into the patient vessel via the third lumen 15. Specifically, in one embodiment, the power extension leg 19 and third lumen 15 are configured to infuse fluids at a rate of between about 3 milliliters and about 8 milliliters per second and at a fluid pressure of between about 50 and 250 psi, though other flow rates and fluid pressures may also be possible. The power extension leg 19 and third lumen 15 can also be used to remove blood or other fluids alone or during simultaneous use of the first and second lumens 12 and 14, and to monitor central venous pressure with the assistance of a transducer. The power extension leg 19 and third lumen 15 are also sufficiently sized to receive a guidewire therethrough to enable insertion of the catheter assembly over the guidewire. Note that the components of the power extension leg 19 are colored purple in one embodiment to indicate power injectability. Other colors could also be used.

Both FIGS. 1 and 2 further include a distal tip region, generally designated at 50, that is configured in accordance one example embodiment of the present invention, the details of which are given below. It should be appreciated that the distal tip region to be described below can be included with hemodialysis catheters, such as those shown in FIGS. 1 and 2, or with other catheters, such as central venous catheters, for example. Indeed, the catheter assembly according to embodiments of the present invention can be adapted for use in other applications, such as chronic dialysis treatment, or where access is desired to be gained to a vessel, such as the internal jugular, subclavian, or femoral vessels, or other body lumen of a patient. Examples of such other applications include apheresis, hemoperfusion, etc.

Reference is now made to FIGS. 2-6, which show various views of a distal tip region, generally designated at 50, of the catheter assembly 10 and configured according to one example embodiment. In detail, the distal tip region 50 generally includes a terminal catheter portion 50A and a nose portion 50B disposed distally of the terminal catheter portion to define a distal end of the catheter assembly 10. The terminal catheter portion 50A, as part of the more proximal portion of the catheter body 11, is composed of suitable material(s) that exhibit qualities, such as suitable softness to allow for ease of insertion without causing vessel trauma, and biocompatibility for enabling the catheter to operate as intended. In one embodiment, the catheter body 11 is composed of material(s) including a thermoplastic polyurethane-based resin material, specifically a polyether-based, aliphatic thermoplastic polyurethane sold under the trademark TECOFLEX, namely TECOFLEX EG-60D-B20, having a Shore D hardness of approximately 60, where "B20" refers to the radiopacifier loading, i.e., barium sulfate loading at 20%. Other suitable materials can also be employed.

In contrast, the nose portion 50B includes a material relatively softer than that of the terminal catheter portion 50A so as to prevent the tip portion from damaging the vessel or other vasculature during vessel entry or transit. In one embodiment, the nose portion 50B is composed of material(s) including TECOFLEX EG-85A-B20 having a Shore A hardness of approximately 85. Notwithstanding the above description, it should be appreciated that the terminal catheter portion and the nose portion can include other materials having the desired properties as described herein and as appreciated by one skilled in the art. One non-limiting example of material that can be used for the terminal catheter portion and nose portion is silicone.

Note that in the illustrated embodiment, the nose portion 50B is joined to the terminal catheter portion 50A via a molding process during manufacture of the catheter assembly 10. In other embodiments, however, other processes for joining the nose portion to the catheter body can be employed, including for instance RF fusion (RF tipping), bonding via adhesive, integrally forming the nose portion with the catheter body, etc.

Figure 3:
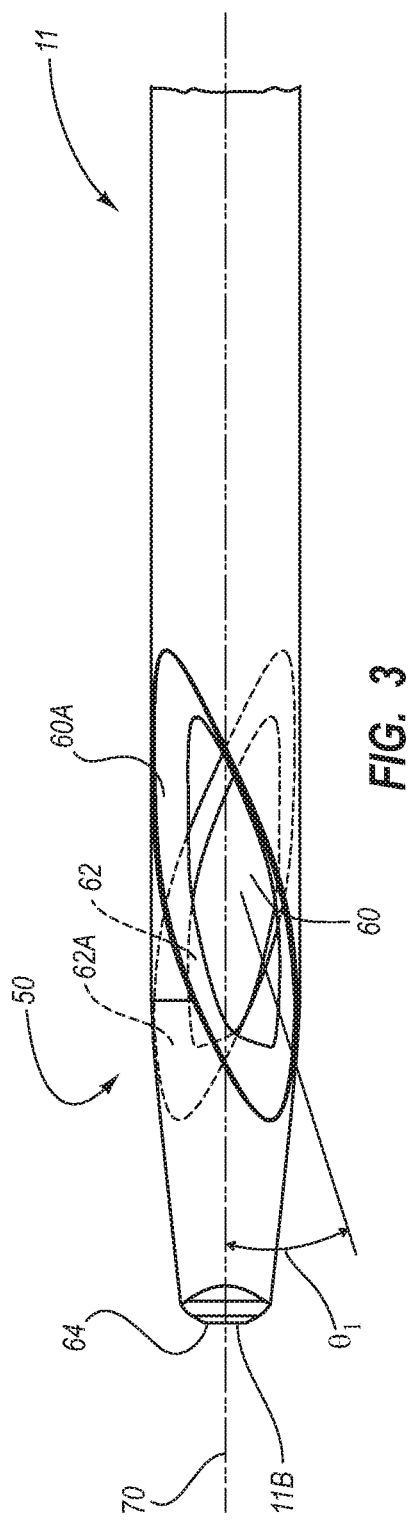
FIG. 3 is a side view of the catheter distal tip region of FIG. 2.
Figure 4:
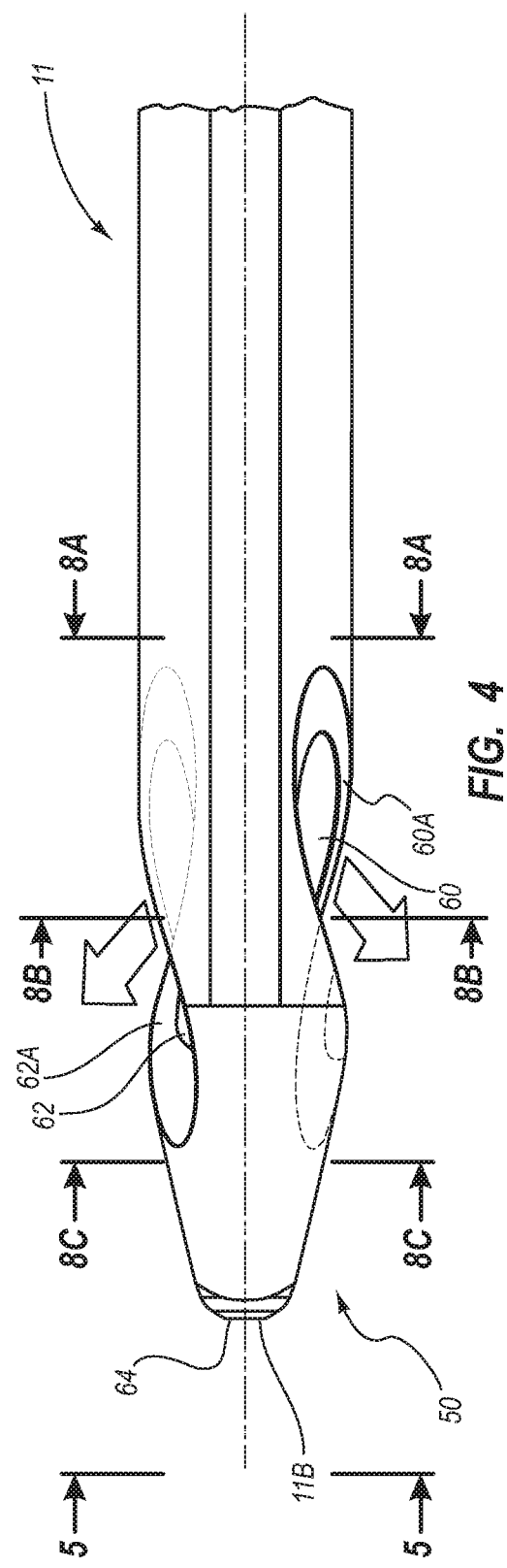
FIG. 4 is a top view of the catheter distal tip region of FIG. 2.

As best seen in FIGS. 3 and 4, the nose portion 50B is distally converging. In the present embodiment, the nose portion 50B is tapered so as to ease entry and passage of a distal portion of the catheter body 11 into the vasculature or other internal cavity of a patient. The nose portion 50B may be colored differently from the remainder of the catheter body 11 to indicate that the catheter assembly 10 can be employed for relatively rapid fluid aspiration and infusion via the third lumen 15 and corresponding power extension leg 19, as was described further above.

The distal tip region 50 includes various openings for enabling the infusion and aspiration of fluids while the catheter assembly 10 is placed for use within the patient vasculature. Specifically, and in accordance with one embodiment, the distal tip region includes a venous lateral opening 60, an arterial lateral opening 62, and a distal end opening 64.

In greater detail, the venous and arterial lateral openings 60 and 62 are positioned opposite one another proximate the catheter body distal end 11B and are defined in a lateral portion of an outer wall of the catheter body 11 so as to be in fluid communication with first lumen 12 and the second lumen 14, respectively, thus enabling blood or other fluids to flow via the openings to/from the lumens when the catheter assembly 10 is positioned within the patient's vasculature. The venous and arterial lateral openings 60 and 62 are defined by perimeters 60A and 62A, respectively, as best seen in FIG. 4 and described further below.

Note that each of the lateral openings 60 and 62 distally extends from the terminal catheter portion 50A into the nose portion 50B. Of course, the exact placement of the lateral openings 60 and 62 along the longitudinal length of the catheter body 11 can vary according the needs of a particular application.

FIG. 4 shows that in the present embodiment the venous and arterial lateral openings 60 and 62 are substantially un-staggered, i.e., equally placed with respect to one another along the longitudinal length of the catheter body 11 such that each is substantially disposed an equal distance from the distal catheter end 11B. Such un-staggered disposal of the lateral openings 60 and 62 enables both openings to be placed proximate a desired location within the vasculature and ensures that the recirculation rate of already treated blood through the catheter assembly 10 is held relatively constant regardless the respective directions of blood travel in/out of the lateral openings. This feature is useful should reversal of blood flow directions through the catheter be necessary. In one embodiment, the recirculation rate in either direction is less than or equal to about five percent. In another embodiment, the venous and lateral openings can be staggered.

FIGS. 2-6 further show the manner in which the venous and lateral openings 60 and 62 are defined in the distal tip region 50. The lateral openings 60 and 62 can take various shapes and configurations as will be shown further below, but in the present embodiment the lateral openings are defined by angled cross-drilled cuts through the outer wall of the catheter body 11 to establish communication with the respective first or second lumens 12, 14. In one embodiment, such cuts are referred to as "skive" cuts.

In one embodiment, a long axis of each cross-drilled cut of the lateral openings 60, 62 defines in one embodiment an angle $\theta_1$ of about 35 degrees with a longitudinal axis of the catheter body 11, though this angle can vary in one embodiment from about greater than zero to about 90 degrees. This angular character imparts both a lateral and distal directional component to fluid flow out of either lateral opening 60, 62, as represented by the flow arrows in FIG. 4, which assists in enabling low-recirculation fluid flow out of or into either lateral opening. Each lateral opening 60 and 62 in the present embodiment is defined by identical cross cuts having the same angle $\theta_1$ with respect to the longitudinal axis 70, though it is also possible to vary the angle generally, or to vary the angle differently for each opening.

In one embodiment, the lateral openings can be defined by a compound-angle cross cut, wherein the long axis of each lateral opening defines an angle with the catheter body longitudinal axis and with a plane dividing the first lumen and the second lumen, i.e., coplanar with the septum separating the first and second lumens proximal of the distal tip region.

An end view of the cross cut, depicted in FIG. 6, shows that the cross cut of each opening 60 and 62 in the illustrated embodiment is made so as to generally define a semicircular cavity through a peripheral portion of the distal tip region 50. This cavity is defined by a portion of a circle 72 having a radius "R," shown in FIG. 6. In the present embodiment, the cross cut that defines the lateral openings 60 or 62 is achieved via use of a cylindrical drill bit or coring tool having a radius equal to the radius R of the circle 72 and cutting through the distal tip region 50 set at the angle $\theta_1$. For instance, in one embodiment a drill bit having a radius of 1/16 inch is used to diagonally cross cut the venous and arterial lateral openings 60 and 62 through a catheter body defining an oblong cross section, wherein the average of the major and minor diameters is approximately 0.173 inches. Note that the catheter body size in one embodiment can vary from 7-16 Fr., though other French sizes are also possible. Though shown in connection with the venous lateral opening 60, the above description applies to the arterial opening 62 as well. Note here that, though identically sized and shaped in the present embodiment, the first and second openings could have respectively differing dimensions if desired or needed for a particular application.

As a result of defining the cross cuts as just described, the venous and arterial openings 60 and 62 are defined by their respective perimeters 60A and 62A discussed above. The angle at which the cross cuts are made, together with the shape of the catheter body 11 at the point of the cuts, results in the perimeters 60A and 62A shaped as seen in the accompanying figures. As best seen in FIG. 4, each perimeter 60A and 62A defines in the present embodiment a figure-eight shape, or analemma, when viewed in a two-dimensional perspective and an elongate saddle shape when viewed in a three-dimensional perspective. Further, because a distal portion of each opening 60 and 62 is defined on a portion of the tapered nose portion 50B (best seen in FIGS. 4 and 5), each opening has a distal-facing component, best seen in FIG. 5, wherein a portion each lateral opening is distally visible.

The configuration of the venous and arterial lateral openings 60 and 62 described above provides various aspects for the catheter assembly 10. First, because of their saddle shapes, the lateral openings 60 and 62 partially extend circumferentially about the outer perimeter of the catheter body 11. This helps to prevent undesired suctioning of the distal tip region 50 to the vessel wall when one of the openings is removing blood from the vessel as the negative flow pressure of the opening is distributed about a portion of the catheter body circumference. If vessel suck-up does occur, the lateral openings 60, 62 are shaped so as to nonetheless provide acceptable fluid flow in and out of the catheter assembly 10. The relatively large size of the lateral openings 60 and 62 also assists in the prevention of occlusion or sheath formation and provides a fanned-out or wide distribution of fluid flowing out therefrom. Recirculation efficiency rates are improved as a result.

Second, the distal-facing aspect of each lateral opening 60 and 62 assists in imparting a distal direction to fluids being ejected therefrom. This enables the ejected fluid to distally flow away from one respective lateral opening and distal-to-proximal flow into the other lateral opening even when the catheter body 11 is positioned against a vessel wall. In addition, the lateral openings 60, 62 are symmetrically opposed, in direction from one another, i.e., a 180-degree separation as best shown in FIG. 4, so as to ensure fluid entry and exit from the lateral openings occurs on opposite sides of catheter assembly 10, further reducing recirculation. Furthermore, this symmetric positioning produces a "criss-cross" relationship between the lateral openings 60 and 62, as best seen in FIG. 3, which assists in reducing recirculation. Moreover, similar fluid flow characteristics are realized even when fluid flow through the catheter assembly 10 is reversed, as discussed further below. In addition, the lateral opening configuration described herein minimizes radical redirection of the fluid upon exiting the catheter body 11 via either of the lateral openings 60 or 62, which in turn prevents fluid turbulence and possible clotting or hemolysis.

As shown in FIGS. 2-6, the distal end opening 64 is distally located at the distal end of the distal tip region nose portion 50 and is in fluid communication with the third lumen 15 so as to enable high flow rate infusion, i.e., power injection of contrast media or other fluids such as TPN nutritional fluid and medications into the vessel, as well as the removal of blood from the vessel during catheter use. In the case of infusion of contrast media or medications into the vessel, placement of the distal end opening 64 distally of the first and second openings 60 and 62 advantageously results in minimization of contrast media/medication intake into either of the first or second openings if the infusion takes place simultaneously with fluid passage through the venous and arterial openings 60 and 62, such as during hemodialysis or other treatments.

Note that, in one embodiment a guidewire can be inserted through the distal end opening 64, the third lumen 15, and the power extension leg 19 during initial or exchange catheter placement in the patient vasculature. Also note that the relatively proximate placement of the three openings 60, 62, and 64 in the distal portion of the catheter body 11 enables each opening to be placed near desired location within the vasculature, such as the superior vena cava ("SVC").

Figure 7A:
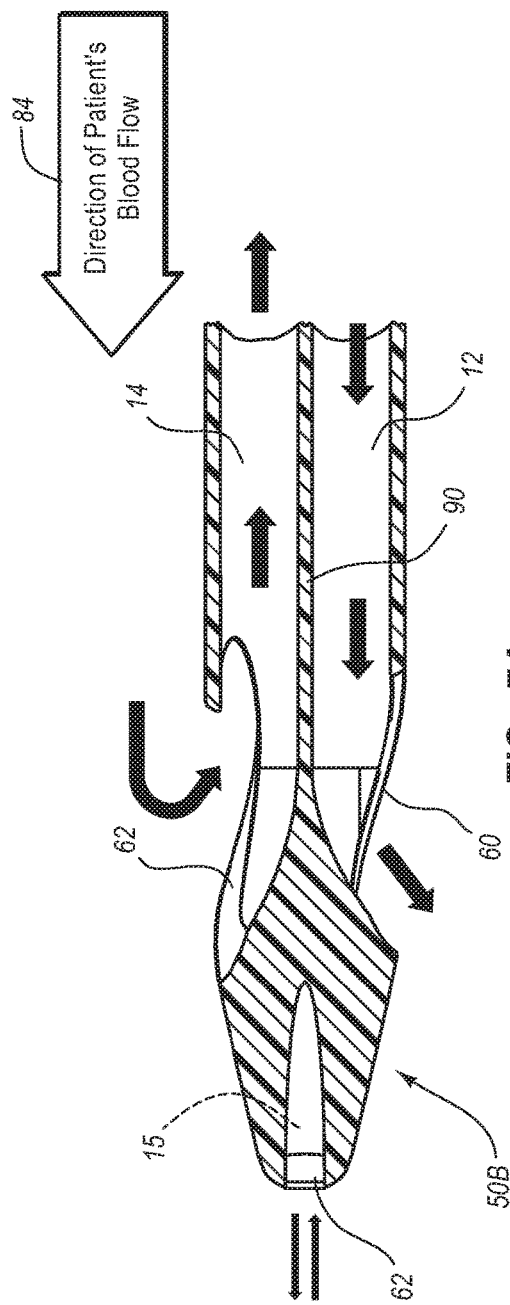
FIG. 7A is a cross sectional view of the catheter assembly and distal tip region of FIG. 2, showing the flow of blood therethrough in a "forward" flow configuration.
Figure 7B:
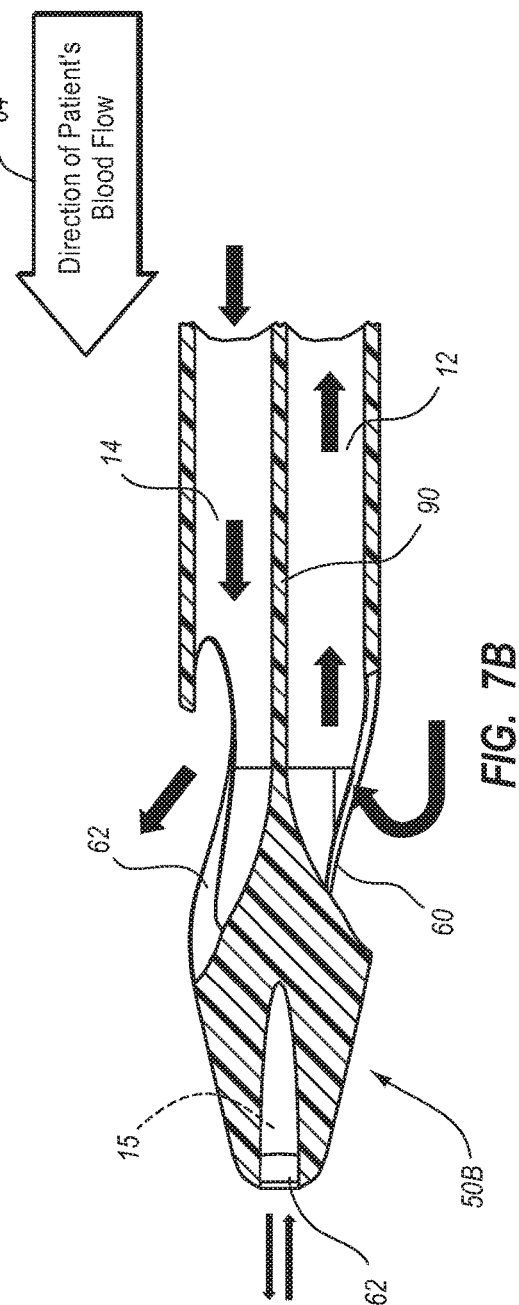
FIG. 7B is a cross sectional view of the catheter assembly and distal tip region of FIG. 2, showing the flow of blood therethrough in a "reverse" flow configuration.

Reference is now made to FIGS. 7A and 7B in describing flow characteristics with respect to the configuration of the distal tip region 50 of the catheter assembly 10 according to the present embodiment. FIGS. 7A and 7B show the distal tip region 50 after the catheter assembly 10 has properly positioned within a vessel of a patient. Arrow 84 shows the direction of blood flow past the distal tip region 50 within the patient's vessel.

In greater detail, FIG. 7A shows fluid flow through the distal tip region 50 in a "forward" direction, wherein blood is aspirated by the second lumen 14, or "uptake" lumen, for removal from the body and treatment by a hemodialysis apparatus or for some other suitable purpose. Aspirated blood enters the second lumen 14 via the arterial lateral opening 62 of the distal tip region 50. Similarly, blood is infused, or returned, to the vessel by the first lumen 12, or "return" lumen, after treatment by a hemodialysis apparatus or some other suitable purpose. Infused blood exits the first lumen 12 from the venous lateral opening 60. Note that the lateral orientation of the venous and arterial lateral openings 60, 62 provides for low recirculation of already-treated blood within the vessel, recirculation being defined as already-treated blood that is returned to the bloodstream via the venous lumen being immediately aspirated by the arterial lumen to be re-treated. Such recirculation is undesirable as it results in lower treatment efficiency, resulting in longer treatment time.

During hemodialysis procedures, it is sometimes necessary to reverse the blood flow through the catheter assembly 10. FIG. 7B shows fluid flow through the distal tip region 50 during such a "reverse" flow situation. In contrast to the forward flow conditions of FIG. 7A, the second lumen 14 in FIG. 7B is employed to infuse blood into the vessel while the first lumen 12 aspirates blood from the vessel. In this configuration, the infused blood enters the vessel via the arterial lateral opening 62, while the aspirated blood is removed via the venous lateral opening 60. Again, the lateral orientation of the venous and arterial lateral openings 60, 62 provides for low recirculation of already-treated blood within the vessel. Thus, it is seen that low recirculation results regardless of the direction in which the catheter is operating.

FIGS. 7A and 7B further show that fluid can be aspirated or infused via the distal end opening 64 in fluid communication with the third lumen 15 before, after, or during infusion/aspiration by the venous and arterial lateral openings 60, 62. As mentioned, the third lumen 15 and distal end opening 64 are configured so as to withstand relatively high pressurized fluid flow infusion into the vessel. It is appreciated that in other embodiments, more than one of the catheter lumens can be configured for high pressurized fluid flow infusion, if desired.

It should be appreciated that the labels "venous" and "arterial" as used above in describing the various components of the present catheter assembly are employed for sake of convenience in describing aspects of present embodiments. Indeed and as just described, though the arterial lateral opening is normally employed in hemodialysis procedures for aspirating blood from the blood vessel in which the catheter is disposed and the venous lateral opening for returning already treated blood to the vessel, this can be reversed such that blood is returned via the arterial lateral opening and aspirated by the venous lateral opening. As such, embodiments of the present invention should not be considered limited by the use of this and other descriptive terminology herein.

Reference is now made to FIGS. 8A-8C, which depict various details regarding the catheter body 11. In detail, FIG. 8A shows a cross sectional view of the catheter body 11 at a point proximal to the distal tip region 50, showing the first lumen 12, the second lumen 14, and the third lumen 15. The three lumens 12, 14, 15 are defined along the longitudinal length of the catheter body 11 and bounded by an outer perimeter or wall 86. The outer wall 86 of the catheter body 11 in the present embodiment defines an oblong shape and includes a transverse axis 88 that intersects the first and second lumens 12, 14 and spans the width of the catheter body. Placement of the first and second lumens 12, 14 adjacent one another, with the third lumen 15 positioned therebelow, provides a robust lumen configuration that resists inadvertent closure of lumens via kinking of the catheter body 11. In addition, the oblong cross sectional configuration of the catheter body 11 enables circular cross sectional shapes to be employed for the lumens 12, 14, and 15, which are relatively more efficient than "D"-shaped or other shaped lumens in terms of fluid flow.

As seen in FIG. 8B and as previously described, the venous lateral opening 60 is defined so that it intercepts the first lumen 12, while the arterial lateral opening is defined so that it intercepts the second lumen 14. As such, the first lumen 12 establishes fluid communication between the venous extension leg 18 and the venous lateral opening 60, while the second lumen 14 establishes fluid communication between the arterial extension leg 16 and the arterial lateral opening 62. In one embodiment, the angled cross cuts that define the venous and arterial openings 60 and 62 are made tangentially with respect to a septum 90 separating the first and second lumens 12, 14 such that the septum wall remains intact as a barrier between the two lumens.

FIGS. 8A-8C successively depict the manner in which the third lumen is raised from a bottom-central location along the length of the catheter body 11 to a central position upon its exit at the distal end opening 64, as shown in FIG. 5. Of course, other lumen position configurations are also possible.

It is appreciated that various modifications may be made to the catheter assembly configurations described above. It is noted that for purposes of clarity, only selected differences between the foregoing and following embodiments are described. For instance, FIGS. 9A-9F depict a distal tip region 150 including a terminal catheter portion 150A integrally formed with the catheter body 11 and a nose portion 150B including a relatively low hardness, e.g., soft, material and joined to the terminal catheter portion 150A in a manner similar to that already described above in connection with FIGS. 2-6.

Figure 9F:
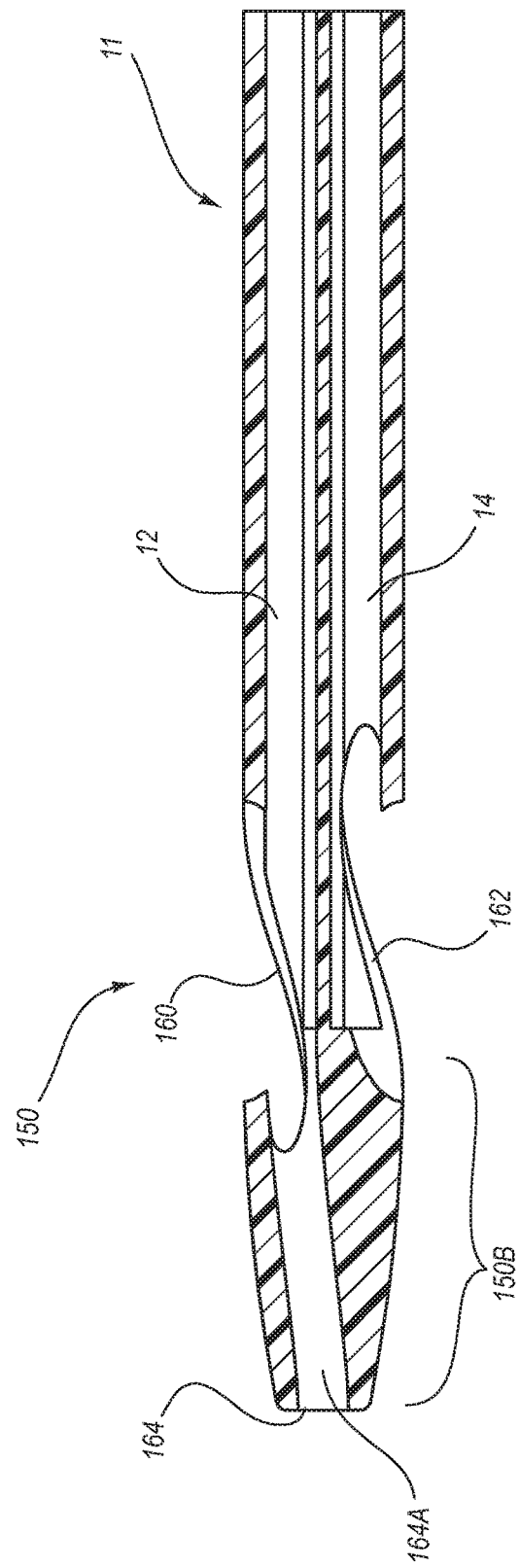

The distal tip region 150 defines a venous lateral opening 160 in fluid communication with the first lumen 12 and an arterial lateral opening 162 in fluid communication with the second lumen 14. A distal end opening 164 is also defined at a distal end of the nose portion 150B. The catheter assembly as configured in FIGS. 9A-9F is a dual lumen device in that it includes only two lumens 12 and 14 (FIG. 9E). As best seen in FIG. 9F, therefore, the distal end opening 164 does not communicate with a third lumen, but rather with a guidewire channel 164A defined by the nose portion 150B, which in turn communicates with the first lumen 12. In this way, a guidewire pathway is established through the catheter body 11 and distal tip region 150 to enable the catheter assembly to be inserted over a guidewire during initial placement and catheter exchange procedures.

FIG. 9E depicts a cross sectional view of the catheter body proximal of the distal tip region 150. As shown, top and bottom portions of an outer wall 186 of the catheter body 11 include thickened regions 186A, which provide added kink resistance to the catheter body.

By virtue of its communication with the first lumen 12, the guidewire channel 164A provides an added fluid outlet/inlet for the first lumen via the distal end opening 164, thus providing an additional fluid pathway that further reduces recirculation during operation of the catheter. This fluid communication also maintains the guidewire channel 164A patent via the flow of blood therethrough so as to prevent occlusion thereof. Further note that, though it is centrally located at the distal end of the nose portion 150B, the venous lateral opening 164 can be positioned such that it and the corresponding guidewire channel 164A are in longitudinal linear alignment with the first lumen 12. Further, the venous lateral opening and the corresponding guidewire channel can be configured as to be in communication with the second lumen or both the first and second lumens, if desired.

Figure 10C:
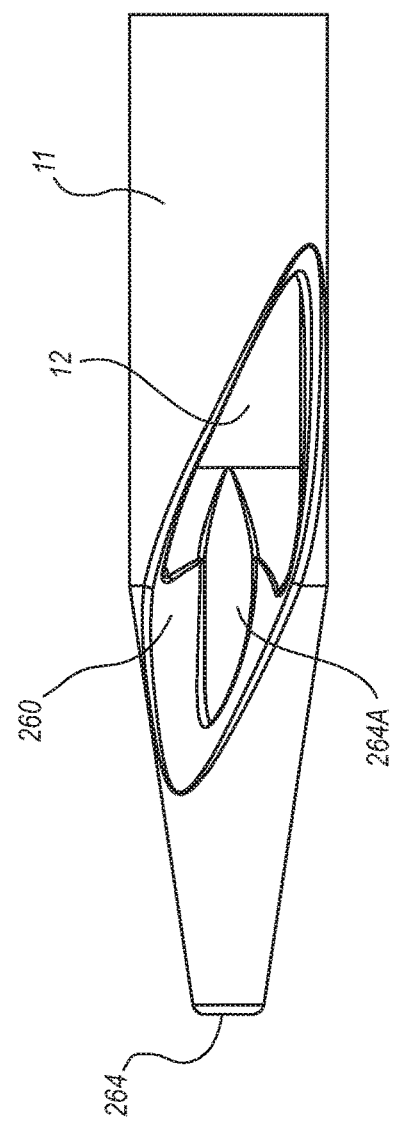
Figure 10D:
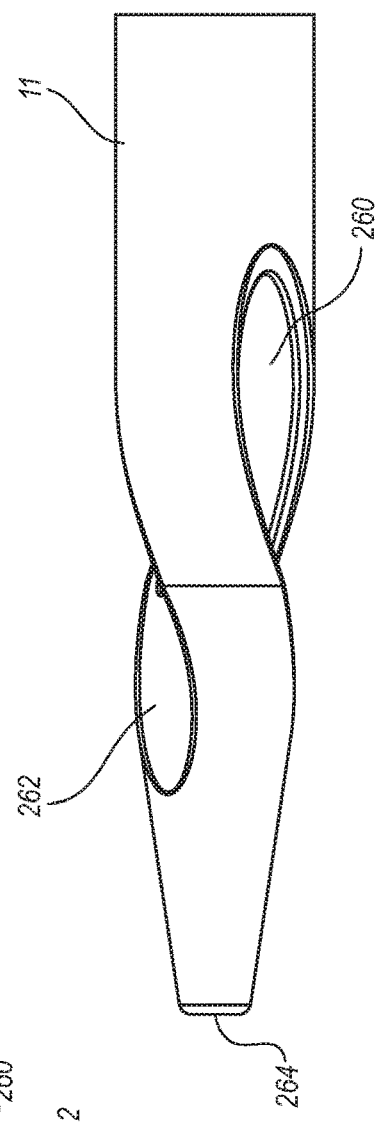
Figure 10B:
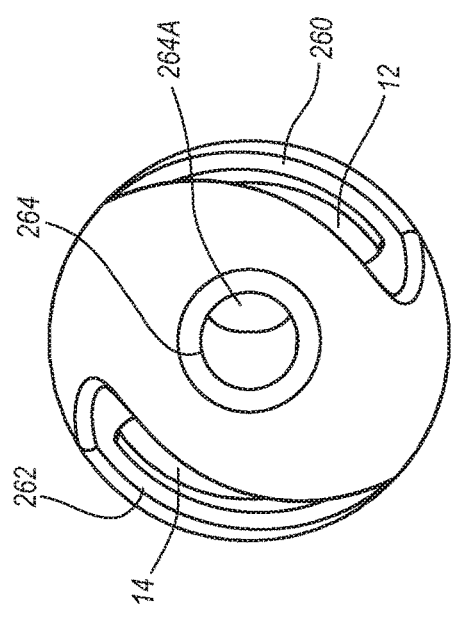
Figure 11C:
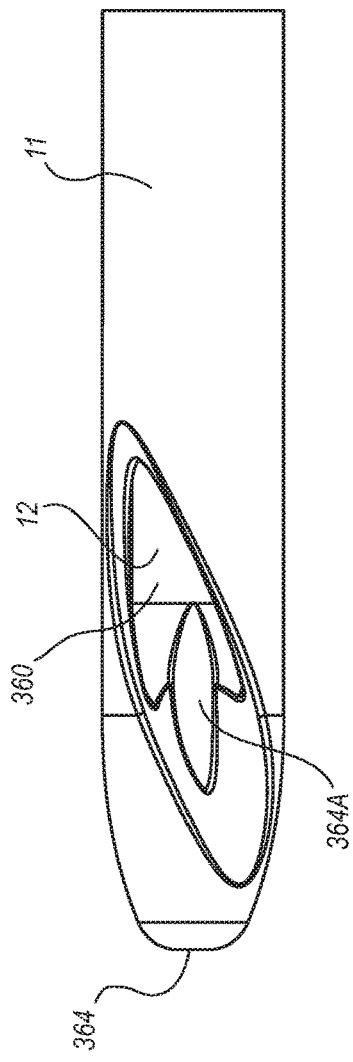
Figure 11D:
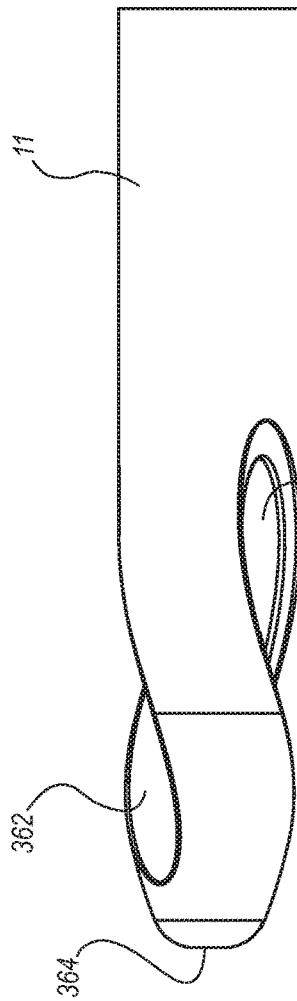
Figure 11B:
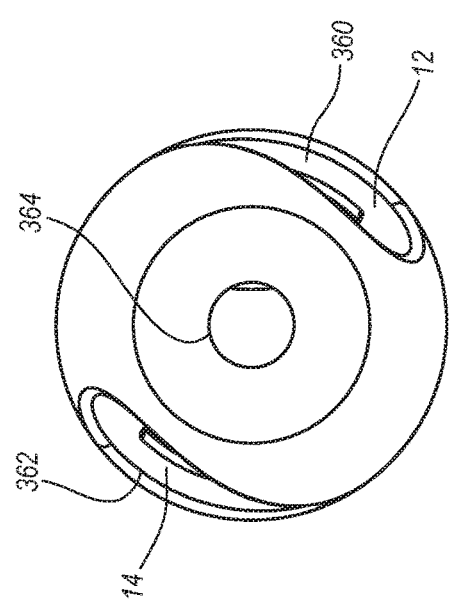

FIGS. 10A-10D and 11A-11D are further examples of a dual lumen catheter assembly configuration, in accordance with example embodiments thereof. The distal tip regions 250/350 each include a terminal catheter portion 250A/350A and a nose portion 250B/350B at which are defined a venous lateral opening 260/360, an arterial lateral opening 262/362, and a distal end opening 264/364. A guidewire channel 264A/364A is defined between the distal end opening 264/364 to the first lumen 12 so as to be in communication therewith. As can be seen in comparison, the lateral openings 260, 262 of FIGS. 10A-10D are differently shaped from corresponding lateral openings 360, 362 of FIGS. 11A-11D. Further, the nose portion 250B (FIG. 10A) is distally converging in a tapered configuration, whereas the nose portion 350B (FIG. 11A) distally converges in a rounded configuration to define a bullet-shape. Note also that the venous and arterial lateral openings of the dual lumen embodiments describe herein include distal-facing portions, as best seen in FIGS. 10B and 11B, offering characteristics similar to those outlined above in connection with the discussion relating to FIGS. 2-6.

FIGS. 12A-20D depict possible configurations of a catheter assembly distal tip region including three lumens, according to additional example embodiments. As they share aspects with the embodiment described above in connection with FIGS. 2-7B, only selected aspects of the embodiments to follow will be discussed below.

FIGS. 12A-12D depicts a catheter assembly distal tip region 450, including a terminal catheter portion 450A and a nose portion 450B. The distal tip region 450 further includes a venous lateral opening 460 in fluid communication with the first lumen 12 and an arterial lateral opening 462 in fluid communication with the second lumen 14. A distal end opening 464 is also defined at a distal end of the nose portion 450B. In the present embodiment, the lateral openings 460 and 462 each define a trapezoidal perimeter when viewed from the perspective of FIG. 12D, and are symmetrically opposed from one another.

FIGS. 13A-13D depicts a catheter assembly distal tip region 550, including a terminal catheter portion 550A and a nose portion 550B. The distal tip region 550 further includes a venous lateral opening 560 in fluid communication with the first lumen 12 and an arterial lateral opening 562 in fluid communication with the second lumen 14. A distal end opening 564 is also defined at a distal end of the nose portion 550B. In the present embodiment, the lateral openings 460 and 462 each define a stepped perimeter when viewed from the perspective of FIG. 13D, and are symmetrically opposed from one another.

Figure 14C:
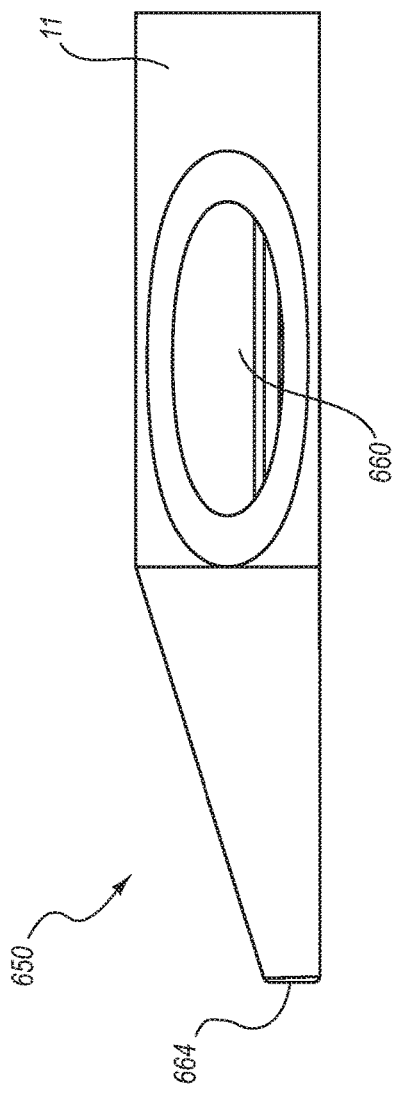
Figure 14D:
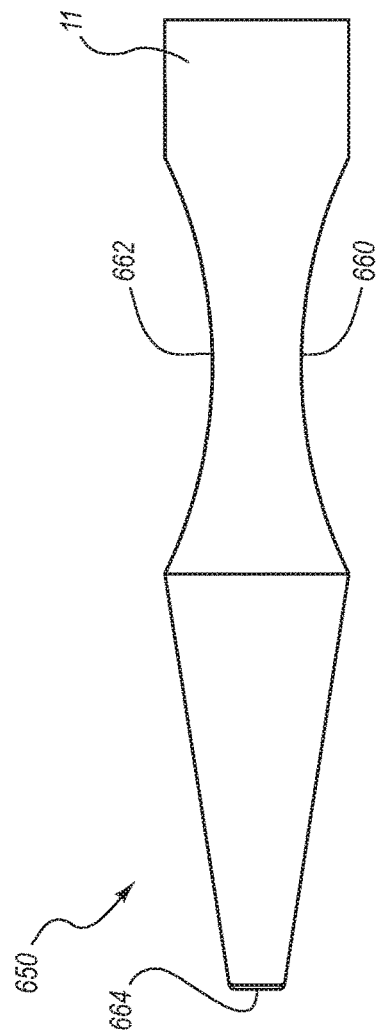
Figure 14B:
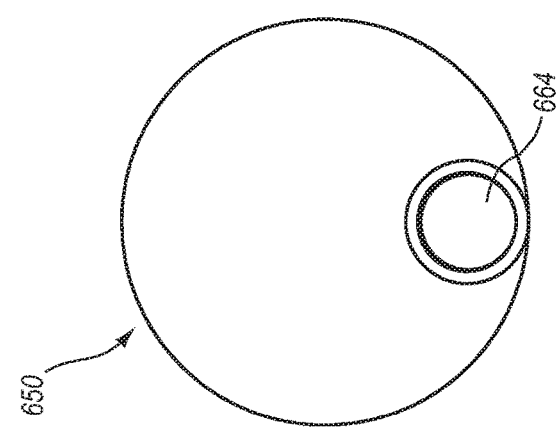

FIGS. 14A-14D depict a catheter assembly distal tip region 650, including a terminal catheter portion 650A and a nose portion 650B. The distal tip region 650 further includes a venous lateral opening 660 in fluid communication with the first lumen 12 and an arterial lateral opening 662 in fluid communication with the second lumen 14. A distal end opening 664 is also defined at a distal end of the nose portion 650B and is axially offset from a central axis of the catheter body 11. In the present embodiment, the lateral openings 660 and 662 each define an oval perimeter when viewed from the perspective of FIG. 12C, and are symmetrically opposed from one another, as best seen in FIG. 14D.

Figure 15A:
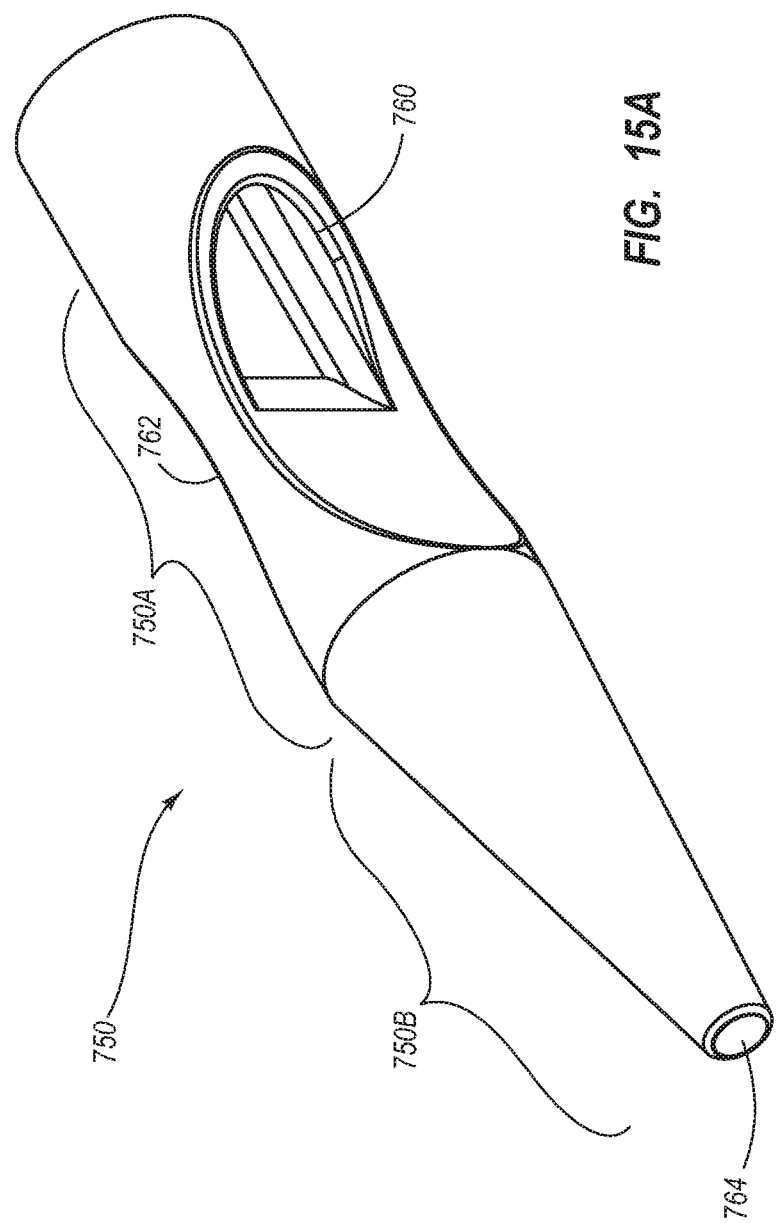
FIGS. 15A-15D are perspective, front, side, and top views, respectively, of a catheter including a distal tip region configured in accordance with one embodiment.
Figure 15C:
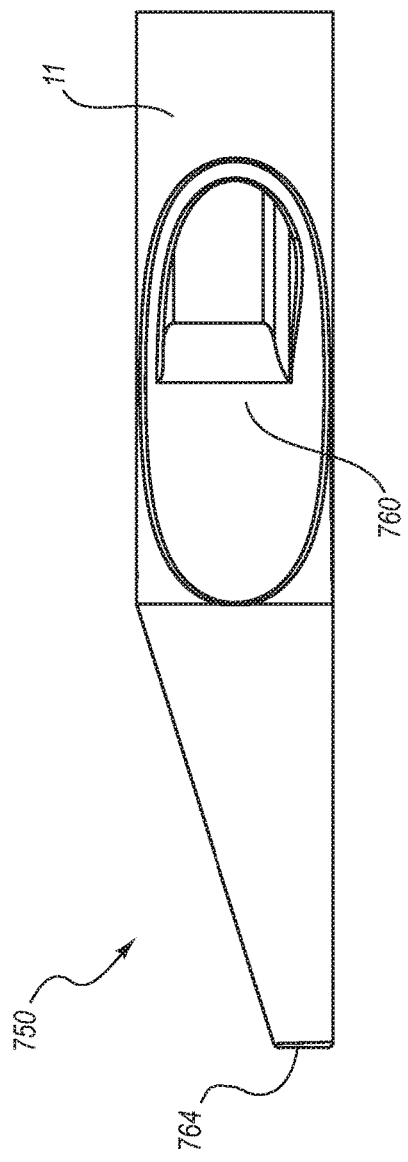
Figure 15D:
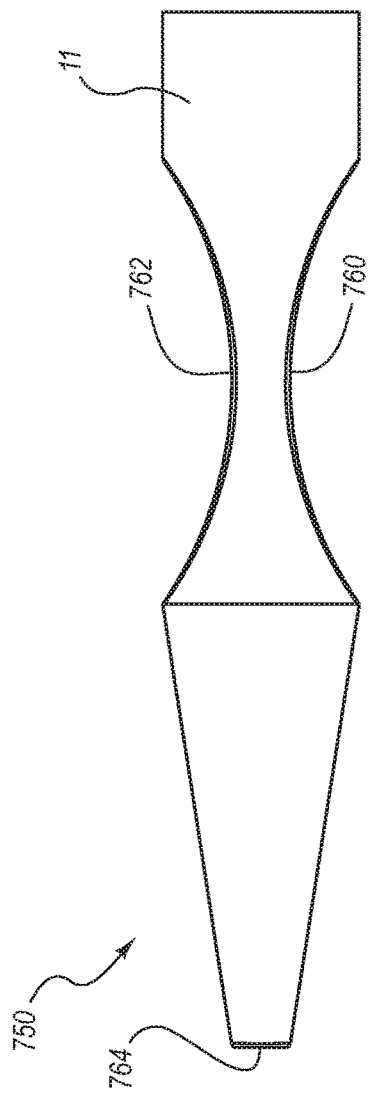
Figure 15B:
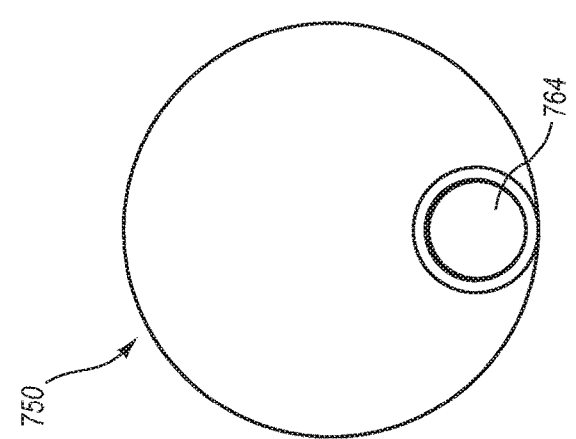

FIGS. 15A-15D depict a catheter assembly distal tip region 750, including a terminal catheter portion 750A and a nose portion 750B. The distal tip region 750 further includes a venous lateral opening 760 in fluid communication with the first lumen 12 and an arterial lateral opening 762 in fluid communication with the second lumen 14. A distal end opening 764 is also defined at a distal end of the nose portion 750B and is axially offset from a central axis of the catheter body 11. In the present embodiment, the lateral openings 760 and 762 each define an oval perimeter when viewed from the perspective of FIG. 15C, and are symmetrically opposed from one another, as best seen in FIG. 15D.

FIGS. 16A-16D depict a catheter assembly distal tip region 850, including a venous lateral opening 860 in fluid communication with the first lumen 12 and an arterial lateral opening 862 in fluid communication with the second lumen 14. A distal end opening 864 is also defined at a distal end of the distal tip region 850 and is axially offset from a central axis of the catheter body 11. In the present embodiment, the lateral openings 860 and 862 are separated by a septum 890, and each defines a partial oval perimeter when viewed from the perspective of FIG. 16C, and are symmetrically opposed from one another, as best seen in FIG. 16D.

FIGS. 17A-17D depict a catheter assembly distal tip region 950, including a venous lateral opening 960 in fluid communication with the first lumen 12 and an arterial lateral opening 962 in fluid communication with the second lumen 14. A distal end opening 964 is also defined at a distal end of the distal tip region 850 and is axially offset from a central axis of the catheter body 11. In the present embodiment, the lateral openings 960 and 962 are separated by a septum 990, and each defines an acute angle-shaped perimeter together with a portion of an outer catheter body wall 986 when viewed from the perspective of FIG. 16C. As before, the lateral openings 960, 962 are symmetrically opposed from one another, as best seen in FIG. 17D.

Figure 18A:
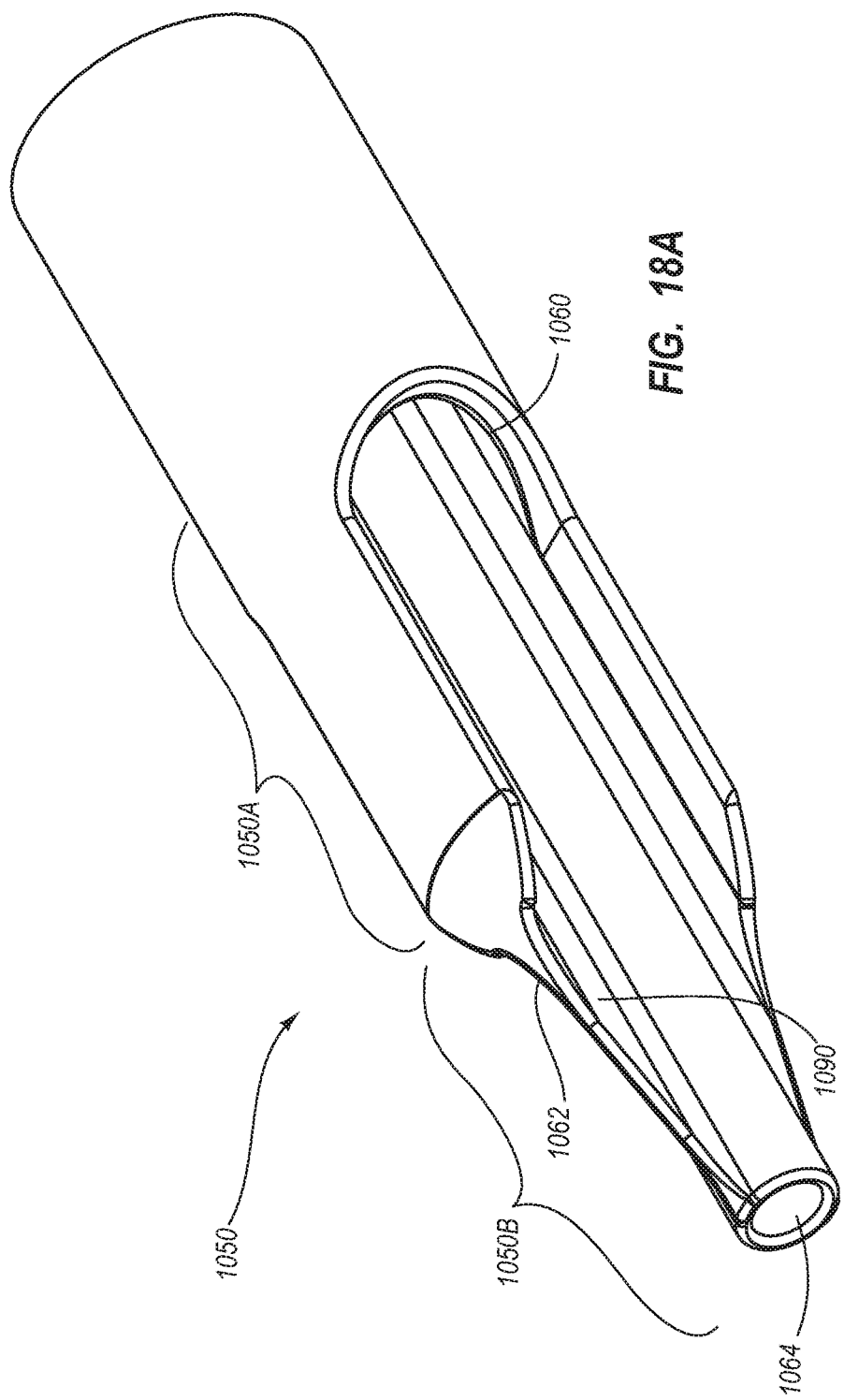

FIGS. 18A-18D depict a catheter assembly distal tip region 1050, including a terminal catheter portion 1050A and a nose portion 1050B. The distal tip region 1050 further includes a venous lateral opening 1060 in fluid communication with the first lumen 12 and an arterial lateral opening 1062 in fluid communication with the second lumen 14. A distal end opening 1064 is also defined at a distal end of the distal tip region nose portion 1050B and is centrally disposed with respect to a central axis of the catheter body 11. In the present embodiment, the lateral openings 1060 and 1062 are separated by a septum 1090, and each defines a partial oval perimeter when viewed from the perspective of FIG. 18C. As before, the lateral openings 1060, 1062 are symmetrically opposed from one another, as best seen in FIG. 18D.

FIGS. 19A-19D depicts a catheter assembly distal tip region 1150, including a nose portion 1150B. The distal tip region 1150 further includes a venous lateral opening 1160 in fluid communication with the first lumen 12 and an arterial lateral opening 1162 in fluid communication with the second lumen 14. A distal end opening 1164 is also defined at a distal end of the distal tip region 1150 and is axially offset from a central axis of the catheter body 11. In the present embodiment, the lateral openings 1160 and 1162 each define a triangular perimeter when viewed from the perspective of FIG. 19D, and are symmetrically opposed from one another as best seen in FIG. 19D.

FIGS. 20A-20D depict a catheter assembly distal tip region 1250, including a terminal catheter portion 1250A and a nose portion 1250B. The distal tip region 1250 further includes a venous lateral opening 1260 in fluid communication with the first lumen 12 and an arterial lateral opening 1262 in fluid communication with the second lumen 14. A distal opening 1264 is also defined on the nose portion 1250B and is axially offset from a central axis of the catheter body 11. In the present embodiment, the lateral openings 1260 and 1262 are separated by a septum 1290, and each defines a frustoconical perimeter when viewed from the perspective of FIG. 20C. As before, the lateral openings 1260, 1262 are symmetrically opposed from one another, as best seen in FIG. 20D. In addition to the lateral openings 1260, 1262, the terminal catheter portion 1250A further includes a plurality of venous openings 1260A and a plurality of arterial openings 1262A. The openings 1260A, 1262A are relatively smaller than the lateral openings 1260, 1262, and are distributed about the perimeter of the catheter body so as to further reduce the possibility of vessel wall suck-up.

FIGS. 21-24 depict various details of a catheter assembly 1310 according to one embodiment. Note that the embodiments described below include various similarities to the embodiments described above; as such, only selected aspects will be discussed below.

As shown, the catheter assembly 1310 includes an elongate catheter tube, or catheter body 1311, which defines a plurality of lumens extending from a proximal end 1311A to a distal end 1311B. The proximal end 1311A of the catheter body 1311 is operably attached to a bifurcation 1320, which in turn is operably attached to extension legs, namely an arterial extension leg 1316, a venous extension leg 1318, and a power extension leg 1319 suitable for power injection of a fluid therethrough. The number of catheter body lumens, extension legs, and their respective configurations can vary from what is shown and described herein. For instance, though shown in FIG. 21 as straight, the arterial and venous extension legs 1316, 1318 can each be curved in a U-shaped configuration, in one embodiment. These and other modifications are contemplated. Note also that "bifurcation" is understood to include a hub that provide two or more fluid pathways.

Figure 21:
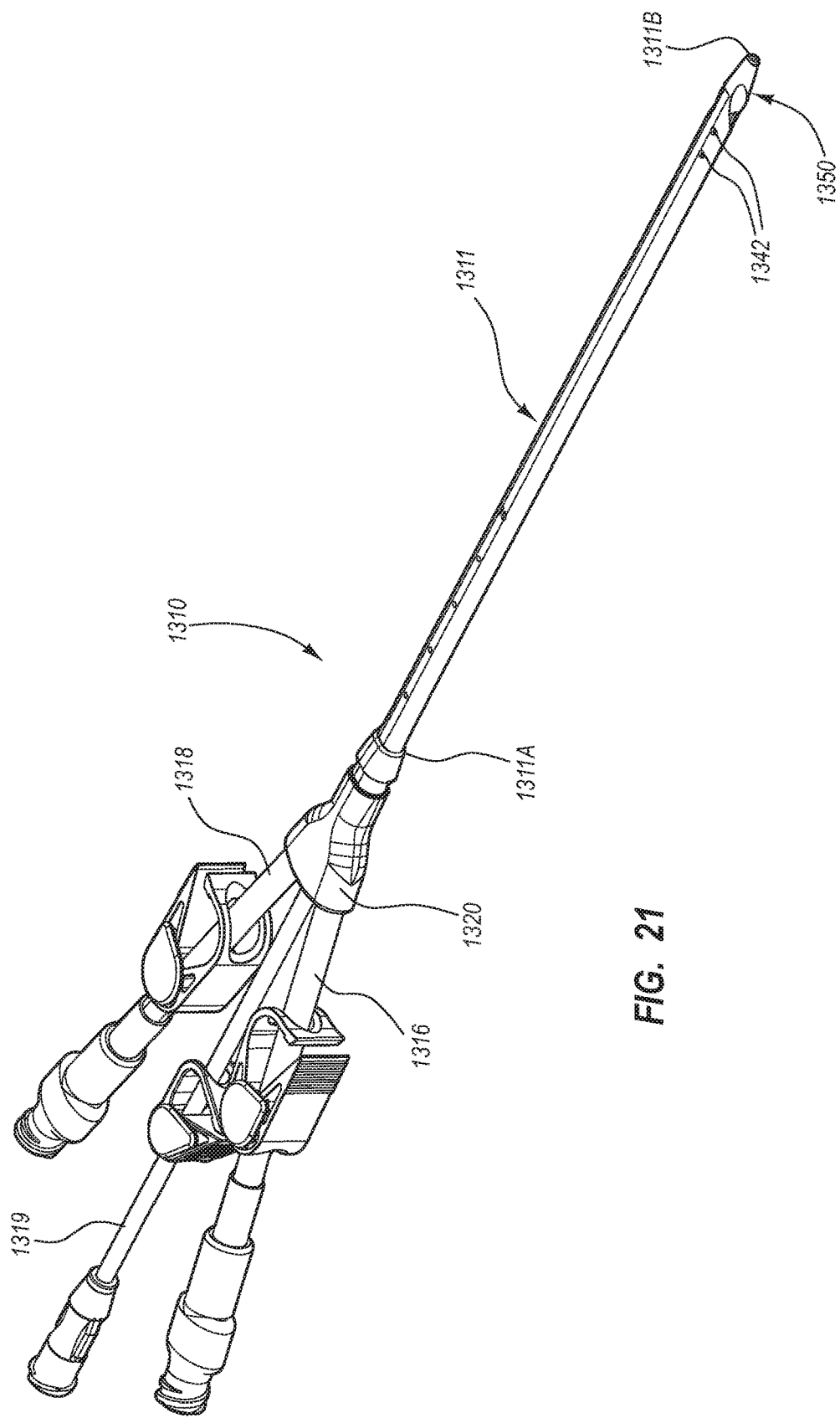
FIG. 21 is a perspective view of a catheter assembly according to one embodiment.
Figure 22A:
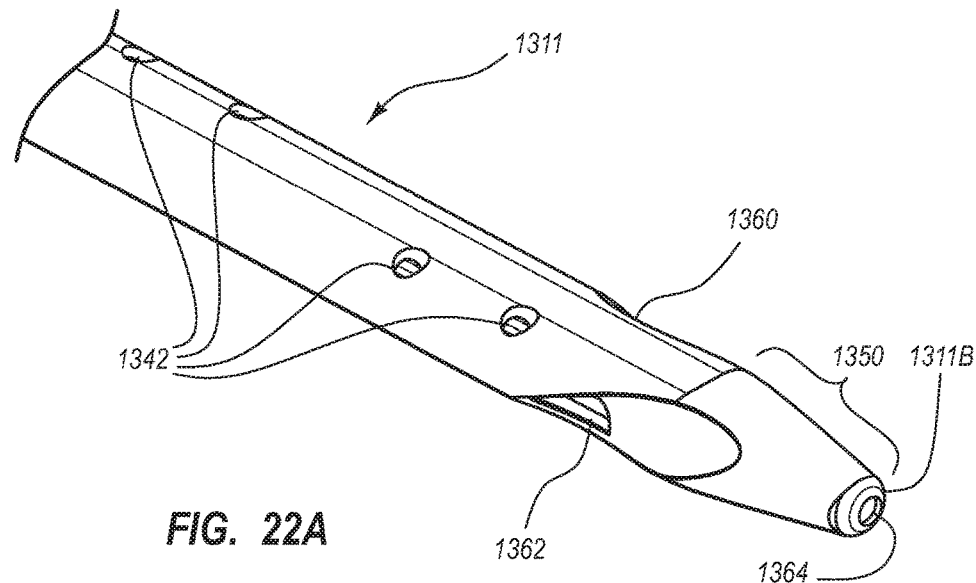
FIGS. 22A and 22B are various perspective views of a distal portion of the catheter assembly of FIG. 21.
Figure 22B:
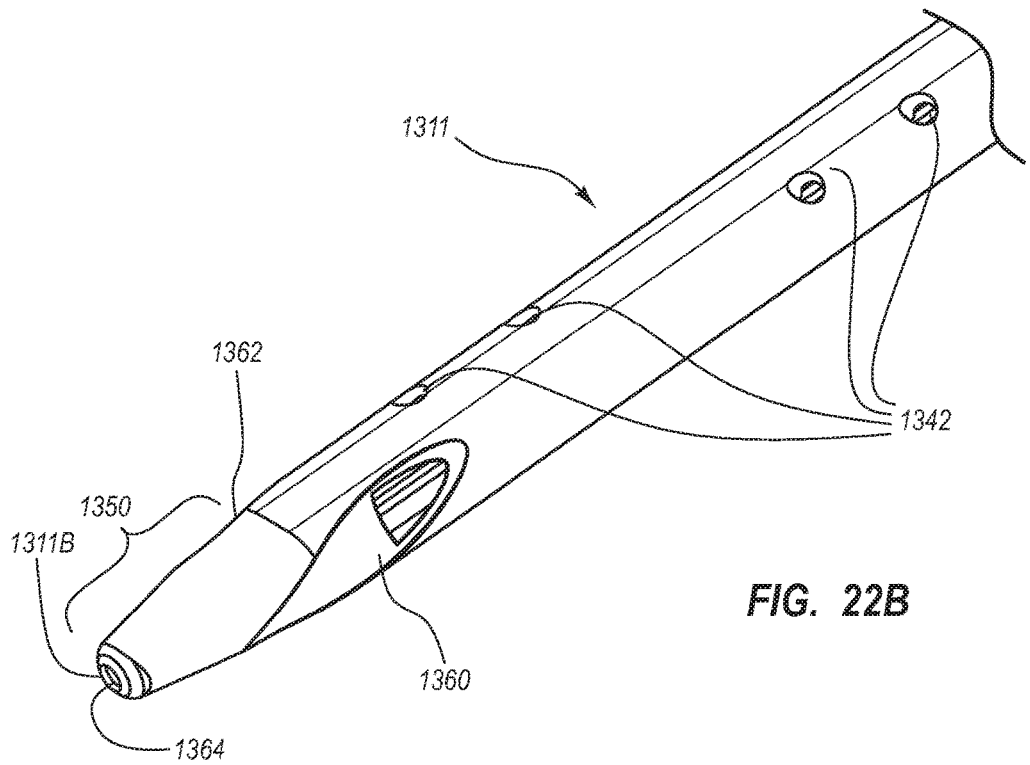

With continuing reference to FIG. 21, reference is made to FIGS. 22A and 22B, which depict distal portions of the catheter assembly 1310 and its elongate catheter body tube 1311, according to the present embodiment. As shown, the distal portion of the catheter body 1311 includes features similar to those shown in FIGS. 1-5 (discussed further above), including a tapered distal tip region 1350, in contrast to the cylindrically flattened oval-shaped outer surface of the more proximal portion of the catheter body, a venous lateral opening 1360, and an arterial lateral opening 1362. The arterial and venous and arterial lateral openings 1360 and 1362 are in fluid communication with respective arterial and venous lumens, which are referenced below and defined by the catheter body 1311. Each of the venous and arterial lateral openings 1360 and 1362 is defined by an angled skive cut so as to impart an angular direction component, with respect to the longitudinal axis of the catheter tube 1311, to fluid entering (via the arterial distal opening) or exiting (via the venous distal opening) the catheter tube, as before.

A third lumen distal end opening 1364 is included at the distal end of the distal tip region 1350 and is in fluid communication with a third lumen defined by the catheter body 1311, as discussed below. In addition, side holes 1342 are included in the catheter body 1311 proximal to the distal tip region 1350, which are in fluid communication with one of the arterial and venous lumens. Such side holes provide an alternate fluid path in addition to the venous and arterial lateral openings 1360, 1362. Note that the particular configuration of the various lateral and side hole openings can vary from what is shown and described herein.

Figure 23A:
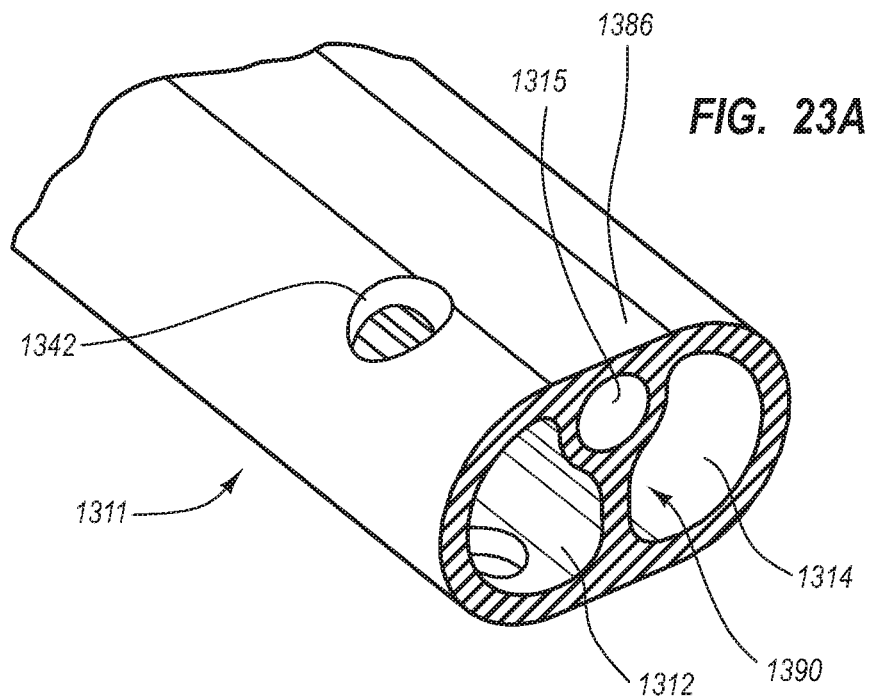
FIGS. 23A-23C are various cross-sectional views of the distal portion of the catheter assembly of FIG. 21.
Figure 23B:
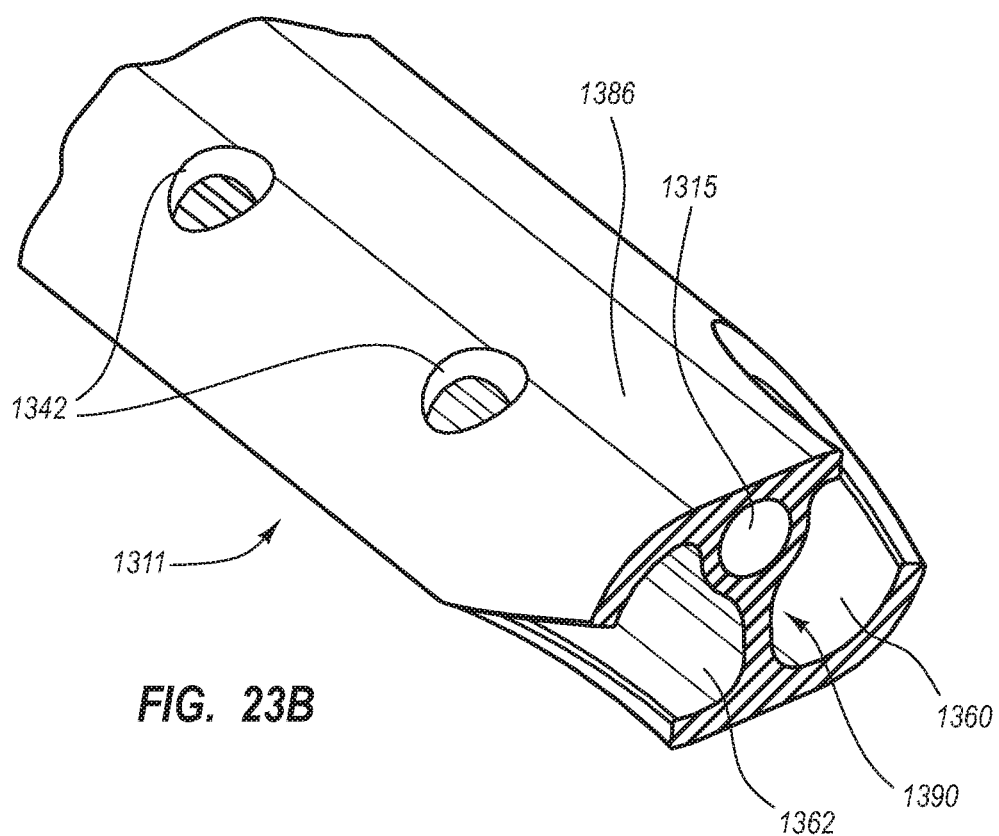
Figure 23C:
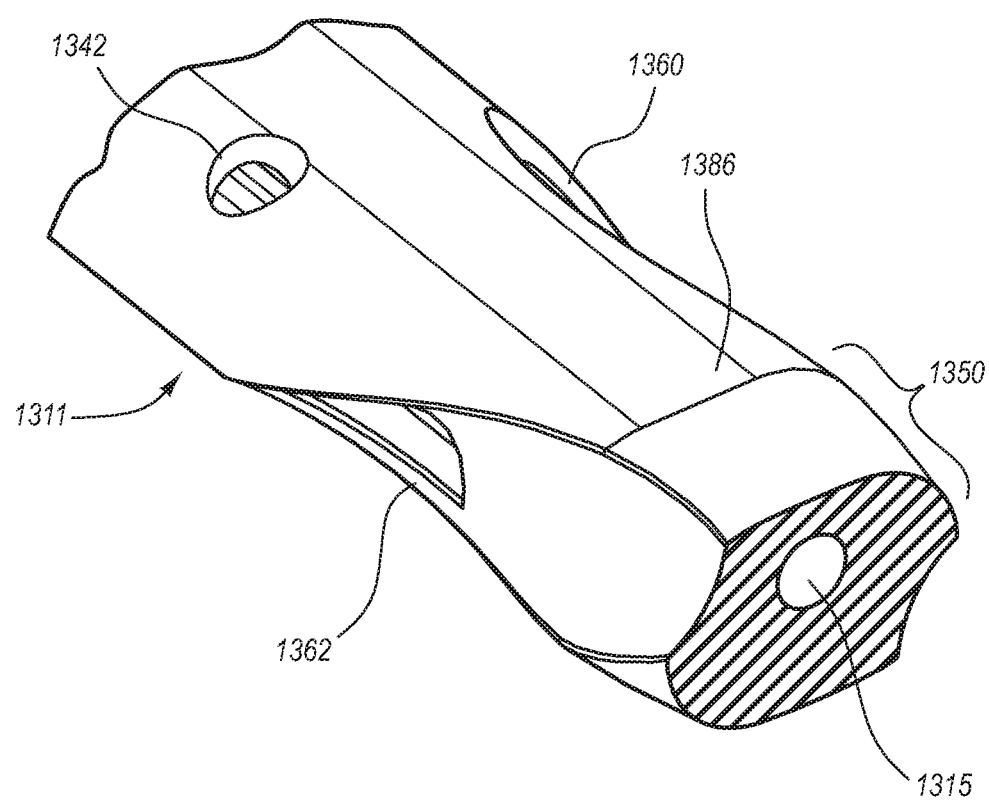

FIGS. 23A-23C depict the lumen configuration of the catheter body 1311 according to the present embodiment. As shown, an outer perimeter, or outer wall 1386 having a substantially flattened oval cross-sectional configuration defines the external portion of the catheter 1311. Indeed, the outer wall 1386 bounds a first, arterial lumen 1312, a second, venous lumen 1314, and a third lumen 1315, as mentioned above. A septum 1390 cooperates with the outer wall 1386 to define the particular shape configurations of the three lumens 1312, 1314, and 1315, which each substantially extend the longitudinal length of the catheter body 1311. FIG. 23B shows the manner in which the arterial lumen 1312 and venous lumen 1314 communicate with the arterial lateral opening 1362 and the venous lateral opening 1360, while FIG. 23C shows the manner in which the third lumen 1315 extends distally toward the distal end opening 1364 on the distal tip region 1350.

Figure 24:
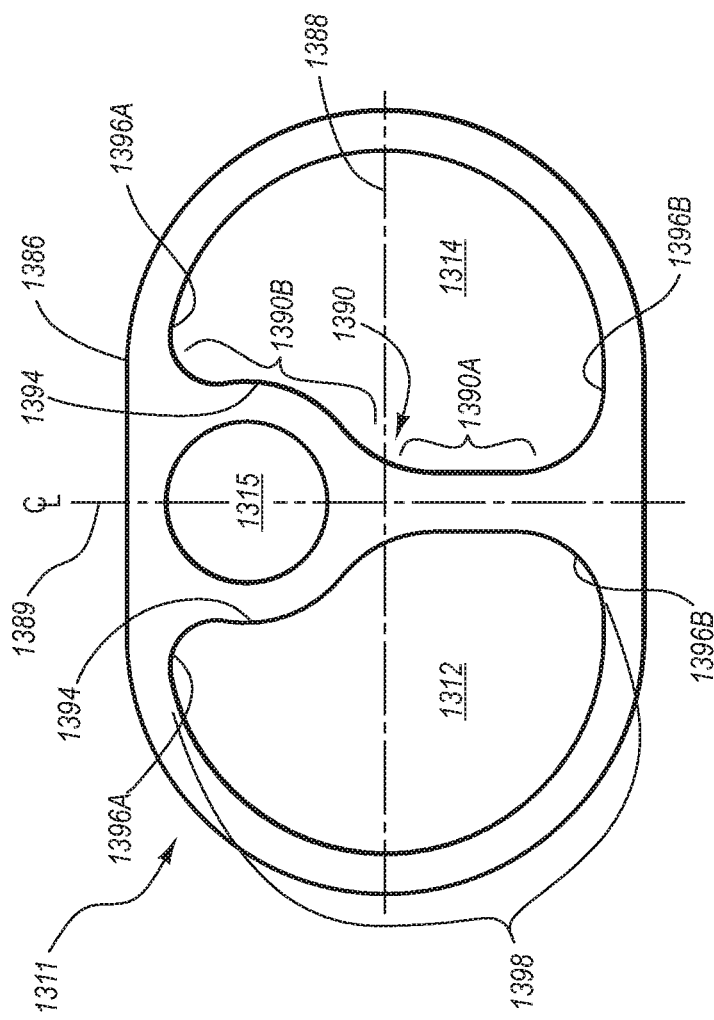
FIG. 24 is a cross-sectional view of the catheter assembly of FIG. 21.

FIG. 24 depicts further details regarding the cross-sectional lumen configuration of the catheter body 1311, according to the present embodiment. As shown, the flattened oval outer wall 1386 and the septum 1390 of the catheter body 1311 define the arterial lumen 1312, the venous lumen 1314, and the third lumen 1315, as mentioned above. FIG. 24 shows that the third lumen 1315 has a cross-sectional shape that is substantially round and is configured in one embodiment to withstand fluid pressures typically associated with power injection, e.g., about 300 psi in one example.

The cross-sectional configurations of the arterial and venous lumens 1312, 1314 are mirror projections of each other as taken across the center line ("CL") indicated at 1389 in FIG. 24. In particular, both the arterial and venous lumens 1312, 1314 cross-sectionally define a deformed kidney bean-shaped cross-sectional lumen profile, also referred to herein as a modified reniform shape. In greater detail, each of the arterial and venous lumens 1312, 1314 cross-sectionally defines a concavely-shaped portion, or concavity 1394, which contributes to the reniform lumen shape. The concavity 1394 for each lumen 1312, 1314 is disposed above a transverse axis 1388 of the catheter body 1311 as shown in and from the perspective of FIG. 24. Disposal of the concavity 1394 of each lumen 1312, 1314 above the transverse axis 1388, as opposed to the concavity being centered on the transverse axis results in a modified reniform configuration, though it is appreciated that the size and location of the concavity can vary from what is shown and described herein. Indeed, in one embodiment the concavity can be positioned so as to define a general reniform (un-deformed kidney bean) shape.

Each lumen 1312, 1314 further includes an arcuate portion, or major arc 1398, opposite the respective concavity 1394 that defines an outer portion of each lumen adjacent the outer wall 1386. The major arc 1398 of each lumen 1312, 1314 is bounded on either end by a top corner 1396A and a bottom corner 1396B. This configuration interposes the top corner 1396A between the major arc 1398 and the concavity 1394. The top and bottom corners 1396A and 1396B are substantially rounded to ensure a laminar flow of fluids through the arterial and venous lumens 1312, 1314, thus desirably preventing areas of fluid flow stagnation.

As shown in FIG. 24, the septum 1390 is included to separate the arterial lumen, 1312, the venous lumen 1314, and the third lumen 1315. Centered on the center line 1389, the septum 1390 includes a unified portion 1390A that generally extends downward from the transverse axis 1388 (from the perspective shown in FIG. 24) and a bifurcated portion 1390B that generally extends upward from the transverse axis. Particularly, the septum 1390 helps define the aformentioned shapes of the lumens. For example, the unified portion 1390A of the septum 1390 generally defines an hourglass-like cross-sectional shape to help define the rounded bottom corners 1396B and the inner portions of both the arterial lumen 1312 and venous lumen 1314, while the bifurcated portion 1390B of the septum cooperates with the outer wall 1386 to define the cross-sectional shape of the third lumen 1315 and the concavities 1394 of the arterial and venous lumens. Note also that the general hourglass configuration of the septum 1390 adds structural strength to the septum.

The cross-sectional configuration shown in FIG. 24 in the present embodiment extends from the proximal end 1311A of the catheter body 1311 distally to the arterial and venous lateral openings 1362, 1360, though this can be modified in other embodiments. It is noted that the various cross-sectional features of the catheter body 1311 described immediately above can vary in size, shape, and position from what is shown and described herein.

According to one embodiment, the various features described above include the following cross-sectional dimensions: the perimeter of the outer wall 1386 includes a width of about 0.195 inch and a height of about 0.128 inch; the diameter of the third lumen is about 0.040 inch; the thickness of the unified portion 1390A of the septum 1390 is about 0.015 inch; the thickness of each branch of the bifurcated portion 1390B of the septum 1390 at the midpoint of the respective concavity 1394 is about 0.010 inch; the distance between the outer surface of the outer wall and the nearest point of the third lumen is about 0.010 inch; the thickness of the outer wall at about the midpoint of the major arc 1398 is about 0.015 inch; the radius of each concavity of the identical arterial and venous lumens 1312, 1314 as measured from a center point of the third lumen is about 0.030 inch; the radius of each top corner 1396A is about 0.012 inch; the radius of each bottom corner 1396B is about 0.020 inch; the radius of each major arc is about 0.052 inch; the radius at the end of the concavity opposite the top corner (at about the transverse axis 1388) is about 0.030 inch; and the distance between the outer surface of the outer wall and the nearest point of arterial or venous lumen proximate the bottom corner thereof is about 0.010 inch. Note that the lumen configuration of the present embodiment enables fluid flow therethrough equal to a known 13 French-sized catheter while occupying the size of only a 12 French catheter. Of course, the size of the catheter body and its respective lumens can be scaled as needed/desired.

The catheter body 1311 in one embodiment includes a suitable thermoplastic such as polyurethane, for instance. In some embodiments, polyurethane thermoplastics sold under the marks TECOFLEX®, CARBOTHANE®, CHRONOFLEX®, and QUADRIFLEX® can be used to form the catheter tube. Note that other suitable, biocompatible materials can also be used. In one embodiment, the catheter tube 12 includes a polyurethane with a 60 D Shore hardness, which assists in preventing kinking, enabling power injection therethrough, and improving insertability into the body of a patient in an acute dialysis scenario, for instance. In other non-limiting embodiments, the hardness of the catheter tube can vary from about 55D to about 65D. Desired characteristics for the material from which the catheter body is formed in one embodiment include thermosensitivity such that the material softens after insertion into the patient body, and suitable polymer strength to withstand power injection pressures to which the catheter assembly may be subjected.

In one embodiment, the atraumatic tip of the distal tip region 1350 includes a polyurethane with an 85A Shore hardness. In one non-limiting example, the atraumatic tip can range from 85A to 75A Shore hardness. In one embodiment, the material of the catheter body 1311 and atraumatic tip can include a radiopaque material, such as barium or tungsten, to enable visibility of the catheter assembly under x-ray imaging.

Figure 25:
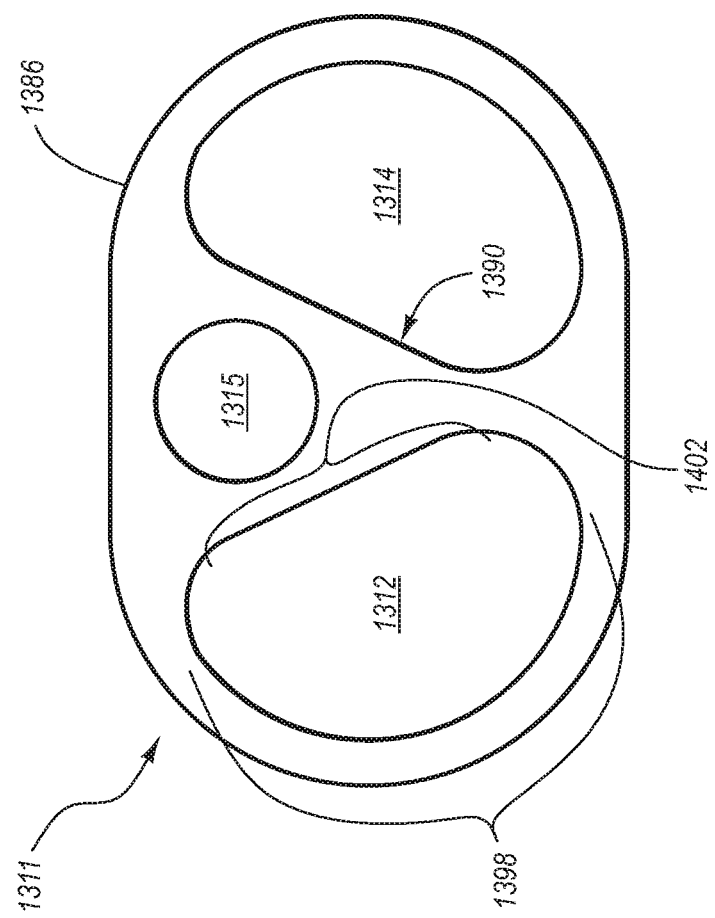
FIG. 25 is a cross-sectional view of a catheter assembly according to one embodiment.

FIG. 25 depicts the catheter body 1311 according to another embodiment, wherein the arterial and venous lumens 1312, 1314 include a differing cross-sectional configuration from that shown in FIG. 24. As shown, the substantially identical arterial and venous lumens 1312, 1314 each cross-sectionally define the major arc 1398 and opposite thereto a flattened side 1402, defined by the septum 1390.

Figure 26:
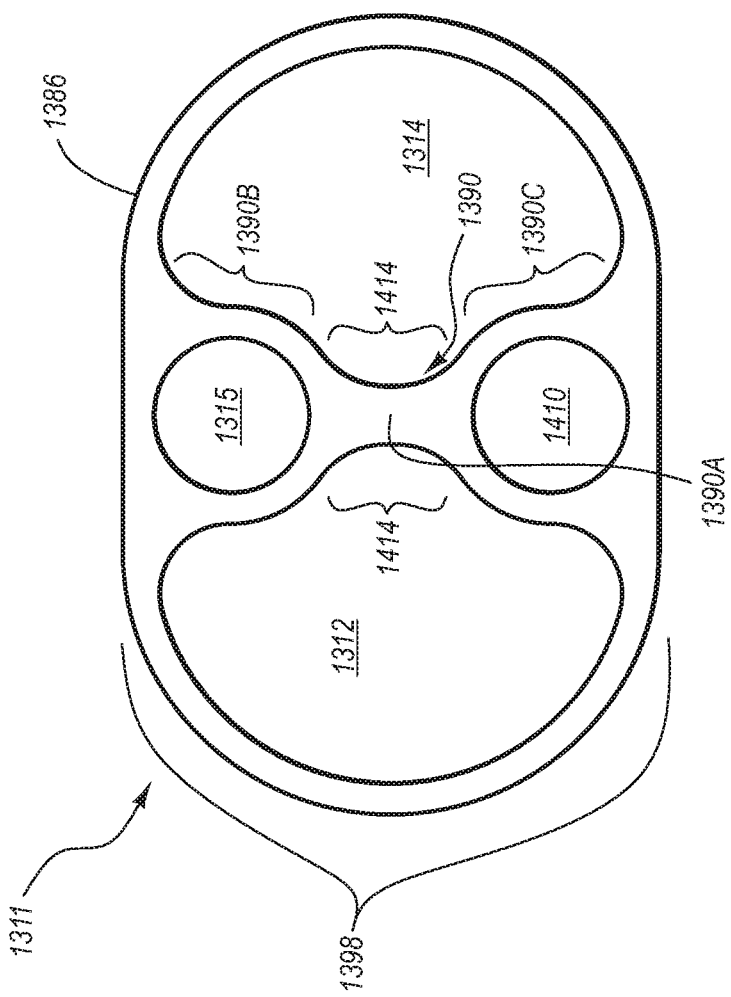
FIG. 26 is a cross-sectional view of a catheter assembly according to one embodiment.

FIG. 26 depicts the catheter body 1311 according to another embodiment, wherein the arterial and venous lumens 1312, 1314 include a differing cross-sectional configuration from that shown in FIG. 24. As shown, a fourth lumen 1410, substantially round in cross-sectional shape, is included. Further, the substantially identical arterial and venous lumens 1312, 1314 each cross-sectionally define the major arc 1398 and opposite thereto a convex portion 1414, defined by the septum 1390. In particular, the septum 1390 includes a centrally disposed unified portion 1390A and a first and second bifurcated portion 1390B, 1390C that are disposed on either side of the unified portion and largely define the third lumen 1315 and fourth lumen 1410.

Figure 27:
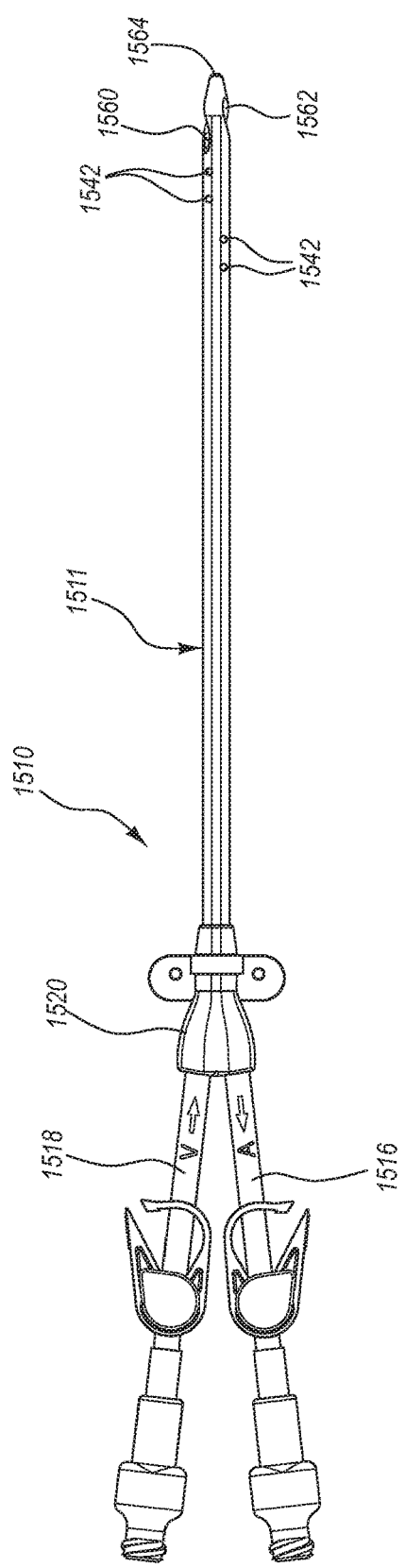
FIG. 27 is a perspective view of a catheter assembly according to one embodiment.

FIGS. 27 and 28 depict various details of a catheter assembly 1510 according to one embodiment. Note that the embodiments described below include various similarities to the embodiments described above; as such, only selected aspects will be discussed below.

As shown, the catheter assembly 1510 includes an elongate catheter tube, or catheter body 1511, which defines a plurality of lumens extending from a proximal end to a distal end thereof. The proximal end of the catheter body 1511 is operably attached to a bifurcation 1520, which in turn is operably attached to extension legs, namely an arterial extension leg 1516 and a venous extension leg 1518. The number of catheter body lumens, extension legs, and their respective configurations can vary from what is shown and described herein. For instance, though shown in FIG. 27 as straight, the arterial and venous extension legs 1316, 1318 can each be curved in a U-shaped configuration, in one embodiment. These and other modifications are contemplated.

The distal portion of the catheter body 1511 includes features similar to those shown in FIGS. 1-5 (discussed further above), including a tapered distal tip region in contrast to the cylindrically flattened oval-shaped outer surface of the more proximal portion of the catheter body, a venous lateral opening 1560, and an arterial lateral opening 1562. The venous and arterial lateral openings 1560 and 1562 are in fluid communication with respective venous and arterial lumens, which are referenced below and defined by the catheter body 1511. Each of the venous and arterial lateral openings 1560 and 1562 is defined by an angled skive cut so as to impart an angular direction component, with respect to the longitudinal axis of the catheter tube 1511, to fluid entering (via the arterial distal opening) or exiting (via the venous distal opening) the catheter tube, as before.

A distal end opening 1564 is included at the distal end of the distal tip region and is in fluid communication with the venous lumen, described below, though the distal end opening could be in communication with the arterial lumen in another embodiment. In addition, side holes 1542 are included in the catheter body 1511 proximal to the distal tip region, which are in fluid communication with one of the arterial and venous lumens. Such side holes provide an alternate fluid path in addition to the venous and arterial lateral openings 1560, 1562. Note that the particular configuration of the various lateral and side hole openings can vary from what is shown and described herein.

FIG. 28 depicts further details regarding the cross-sectional lumen configuration of the catheter body 1511, according to the present embodiment. As shown, an outer perimeter, or outer wall 1586 having a substantially flattened oval cross-sectional configuration defines the external portion of the catheter 1511. Indeed, the outer wall 1586 bounds a first, arterial lumen 1512 and a second, venous lumen 1514, as mentioned above. A septum 1590 cooperates with the outer wall 1586 to define the particular shape configurations of the two lumens 1512 and 1514, which each substantially extend the longitudinal length of the catheter body 1511. As discussed, the arterial lumen 1512 and the venous lumen 1514 communicate with the arterial lateral opening 1562 and the venous lateral opening 1560, respectively.

FIG. 28 depicts further details regarding the cross-sectional lumen configuration of the catheter body 1511, according to the present embodiment. As shown, the flattened oval outer wall 1586 and the hourglass-shaped septum 1590 of the catheter body 1511 define the arterial lumen 1512 and the venous lumen 1514, as mentioned above. The cross-sectional configurations of the arterial and venous lumens 1512, 1514 are mirror projections of each other as taken across the center line ("CL") indicated at 1389 in FIG. 28. In particular, both the arterial and venous lumens 1512, 1514 cross-sectionally define a modified ellipse cross-sectional lumen profile. In greater detail, each of the arterial and venous lumens 1512, 1514 cross-sectionally defines a first, minor arc 1594 adjacent and defined by the hourglass-shaped septum 1590, bounded by two corners: a top corner 1596A and a bottom corner 1596B. A second, major arc 1598 extends from each of the corners 1596A, 1596B on a side opposite the septum 1590 and adjacent the outer wall 1586 to define the rest of each lumen 1512, 1514. This configuration interposes both the top corner 1596A and the bottom corner 1596B between the major arc 1598 and the minor arc 1594. The top and bottom corners 1596A and 1596B are substantially rounded to ensure a laminar flow of fluids through the arterial and venous lumens 1512, 1514, thus desirably preventing areas of fluid flow stagnation.

As shown in FIG. 28, the septum 1590 separates the arterial lumen 1512 and the venous lumen 1514. Centered on the center line 1389, the septum 1590 defines an hourgalss cross-sectional shape equally distributed about the transverse axis 1388 and helps define the aforementioned shapes of the lumens. Note that the general hourglass configuration of the septum 1590 adds structural strength to the septum.

The cross-sectional configuration shown in FIG. 28 in the present embodiment extends from the proximal end of the catheter body 1511 distally to the arterial and venous lateral openings 1562, 1560, though this can be modified in other embodiments. It is noted that the various cross-sectional features of the catheter body 1511 described immediately above can vary in size, shape, and position from what is shown and described herein.

According to one embodiment, the various features described above include the following cross-sectional dimensions: the perimeter of the outer wall 1386 includes a width of about 0.173 inch and a height of about 0.115 inch; the thickness of the septum 1390 at the transverse axis 1388 is about 0.015 inch; the thickness of outer wall along the major arc 1598 is about 0.010 inch; the radius of the minor arc 1594 is about 0.100 inch; the radius of the major arc 1598 is about 0.050 inch; the width of each lumen 1512, 1514 at the transverse axis 1388 is about 0.072 inch; and the radius of each corner 1596A, 1596B is about 0.016 inch. Note that the above dimensions pertain to a catheter assembly 1510 having an 11 French size; of course, the size of the catheter body and its respective lumens can be scaled as needed/desired. The catheter body 1511 and its atraumatic tip can include suitable materials as have been described further above.

Embodiments of the present invention may be embodied in other specific forms without departing from its spirit or essential characteristics. The described embodiments are to be considered in all respects only as illustrative, not restrictive. The scope of the embodiments of the present invention is, therefore, indicated by the appended claims rather than by the foregoing description. All changes that come within the meaning and range of equivalency of the claims are to be embraced within their scope.

What is claimed is:

1. A method for making an elongate catheter tube, the method comprising:
    extruding an extrusion material to define:
        an outer surface having a flattened oval cross-sectional shape with opposing flat sides;
        a first lumen and a second lumen separated by a septum; and
        a third lumen between the first lumen and the second lumen, the third lumen configured to withstand pressures associated with power injection of a fluid therethrough.

2. The method for making according to claim 1, wherein the extruding further comprises defining the first lumen and the second lumen to each have a cross-sectional shape including:
    a minor arc portion adjacent the septum;
    a major arc portion adjacent an outer wall of the catheter tube; and rounded first and second corners interposed between the minor arc portion and the major arc portion.

3. The method for making according to claim 2, wherein the extruding comprises defining the third lumen to be positioned adjacent the minor arc portion of each of the first lumen and the second lumen.

4. The method for making according to claim 1, wherein the extruding comprises defining a wall thickness adjacent the major arc portion to be substantially constant.

5. The method for making according to claim 1, wherein the extruding further comprises defining:
   a first lateral opening in fluid communication with the first lumen, the first lateral opening defined by a first angled cross cut; and
   a second lateral opening in fluid communication with the second lumen, the second lateral opening defined by a second angled cross cut.

6. The method for making according to claim 5, wherein the extruding comprises defining the first angled cross cut to include a first cut and a second cut opposite of the first cut, each of the first cut and the second cut having a long axis at an oblique angle with a longitudinal axis of the elongate catheter tube.

7. The method for making according to claim 1, wherein the extruding further comprises defining the first lumen and the second lumen to each have a cross-sectional shape including:
   an arcuate portion;
   rounded first and second corners disposed at either end of the arcuate portion; and
   a concavity opposite the arcuate portion and interposed between the rounded first and second corners.

8. The method for making according to claim 7, wherein the extruding comprises defining the concavity in an offset configuration with respect to the rounded first and second corners.

9. The method for making according to claim 1, wherein the extruding comprises defining the septum to include a unified portion and a bifurcated portion, the third lumen bounded by the bifurcated portion.

10. The method for making according to claim 1, wherein the extruding comprises defining the septum on a center line of the catheter tube such that the first lumen and the second lumen are disposed in a mirror-image configuration about the center line.

11. The method for making according to claim 1, wherein the extruding comprises defining the first lumen and the second lumen to have substantially identical cross-sectional shapes disposed in a mirror image configuration about the septum.

12. The method for making according to claim 1, wherein the extruding comprises defining the first lumen and the second lumen to each have a cross-sectional shape including:
   a major arc portion adjacent an outer wall of the catheter tube; and
   flattened side opposite of the major arc portion.

13. The method for making according to claim 1, wherein the extruding comprises defining a tapered atraumatic distal tip region.

* * * * *